US010082506B2

(12) United States Patent
Kiessling et al.

(10) Patent No.: US 10,082,506 B2
(45) Date of Patent: Sep. 25, 2018

(54) MICROBIAL GLYCANS AS A TARGET OF HUMAN INTELECTIN

(71) Applicant: Wisconsin Alumni Research Foundation, Madison, WI (US)

(72) Inventors: Laura L. Kiessling, Madison, WI (US); Darryl A. Wesener, Madison, WI (US); Kittikhun Wangkanont, Bangkok (TH)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/933,891

(22) Filed: Nov. 5, 2015

(65) Prior Publication Data

US 2016/0131649 A1 May 12, 2016

Related U.S. Application Data

(60) Provisional application No. 62/075,369, filed on Nov. 5, 2014.

(51) Int. Cl.

| | |
|---|---|
| ***G01N 33/53*** | (2006.01) |
| ***C12Q 1/68*** | (2018.01) |
| ***G01N 33/554*** | (2006.01) |
| ***G01N 33/569*** | (2006.01) |
| ***C07K 14/705*** | (2006.01) |
| ***C07K 14/47*** | (2006.01) |
| ***C07K 7/64*** | (2006.01) |
| *A61K 38/00* | (2006.01) |
| *C12Q 1/689* | (2018.01) |

(52) U.S. Cl.

CPC .......... *G01N 33/56911* (2013.01); *C07K 7/64* (2013.01); *C07K 14/4726* (2013.01); *C07K 14/7056* (2013.01); *G01N 33/56961* (2013.01); *A61K 38/00* (2013.01); *C07K 2319/00* (2013.01); *C12Q 1/689* (2013.01); *G01N 33/56944* (2013.01); *G01N 2333/705* (2013.01)

(58) Field of Classification Search

None

See application file for complete search history.

(56) References Cited

U.S. PATENT DOCUMENTS 7,312,197 B2 * 12/2007 Gong .................. C07K 14/575 514/15.7

OTHER PUBLICATIONS

Tsuji et al., The Journal of Biological Chemistry, 2001; 276(26): 23456-23463.*

Wesener et al., Nature Structural and Molecular Biology, 2015; 22(8): 603-610.*

Blixt et al., "Printed covalent glycan array for ligand profiling of diverse glycan binding proteins," *Proc Natl Acad Sci USA*, 101(49):17033-17038, 2004.

Datta et al., "Identification of novel genes in intestinal tissue that are regulated after infection with an intestinal nematode parasite," *Infect. Immun.*, 73(7):4025-4033, 2005.

French et al., "Up-regulation of intelectin in sheep after infection with Teladorsagia circumcincta," *Int. J. Parasitol.*, 38(3-4):467-475, 2008.

Kincaid et al., "Virtual screening for UDP-galactopyranose mutase ligands identifies a new class of antimycobacterial agents," *ACS Chem. Biol.*, 10:2209-2218, 2015.

Nassau et al., "Galactofuranose biosynthesis in *Escherichia coli* K-12: identification and cloning of UDP-galactopyranose mutase ," *J Bacteriol*, 178(4):1047-1052, 1996.

Pedersen and Turco, "Galactofuranose metabolism: a potential target for antimicrobial chemotherapy ," *Cell Mol Life Sci*, 60(2):259-266, 2003.

Pemberton et al., "Proteomic analysis of mouse jejunal epithelium and its response to infection with the intestinal nematode, Trichinella spiralis," *Proteomics*, 4(4):1101-1108, 2004.

Tefsen et al., "Galactofuranose in eukaryotes: aspects of biosynthesis and functional impact," *Glycobiology*, 22:456-469, 2012.

Voehringer et al., "Nippostrongylus brasiliensis: identification of intelectin-1 and -2 as Stat6-dependent genes expressed in lung and intestine during infection," *Exp Parasitol*, 116:458-466, 2007.

Wesener et al., "Recognition of microbial glycans by human intelectin-1," Nature Structural & Molecular Biology, 22(8):603-613, and Supplementary Information, 2015.

Wesener et al., "UDP-galactopyranose mutase in nematodes ," *Biochemistry*, 52:4391-4398, 2013.

* cited by examiner

*Primary Examiner* — Gary B Nickol
*Assistant Examiner* — Lakia J Jackson-Tongue
(74) *Attorney, Agent, or Firm* — Parker Highlander, PLLC

(57) ABSTRACT

The present disclosure provides for methods of diagnosing and treating bacterial infections. Human Intelectin 1 (hIntL-1) has been shown to bind selectively to glycan components on bacteria including *Streptococcus pneumonia, Proteus mirabilis, Proteus vulgaris, Klebsiella pneumonia* and *Yersinia pestis*. This interaction can be targeted to identify, purify and therapeutically target such organisms.

10 Claims, 35 Drawing Sheets
(30 of 35 Drawing Sheet(s) Filed in Color)
Specification includes a Sequence Listing.

Intelectin Protein Primary Sequence Percentage Identity

| 1 | 2 | 3 | 4 | 5 | 6 | | |
|---|---|---|---|---|---|---|---|
| | 84.0 | 81.6 | 79.7 | 79.2 | 64.2 | 1 hIntL-1 | Human IntL-1 |
| | | 80.2 | 77.6 | 77.5 | 62.9 | 2 hIntL-2 | Human IntL-2 |
| | | | 91.4 | 76.9 | 64.9 | 3 mIntL-1 | Mouse IntL-1 |
| | | | | 75.0 | 63.6 | 4 mIntL-2 | Mouse IntL-2 |
| | | | | | 60.8 | 5 sIntL-1 | Sheep IntL-1 |
| | | | | | | 6 XIntL | *Xenopus laevis* IntL |

Clustal W Alignment of Intelectin and Ficolin Proteins

B

Intelectin and Ficolin Protein Primary Sequence Percentage Identity

| 1 | 2 | 3 | 4 | 5 | 6 | | |
|---|---|---|---|---|---|---|---|
| | 81.2 | 65.5 | 12.1 | 12.3 | 12.6 | 1 hIntL-1 | Human IntL-1 |
| | | 84.9 | 11.3 | 11.9 | 12.3 | 2 mIntL-1 | Mouse IntL-1 |
| | | | 14.7 | 12.5 | 12.4 | 3 XIntL | *Xenopus laevis* IntL |
| | | | | 50.3 | 48.8 | 4 h H-Ficolin | Human H-Ficolin |
| | | | | | 80.2 | 5 h L-Ficolin | Human L-Ficolin |
| | | | | | | 6 h M-Ficolin | Human M-Ficolin |

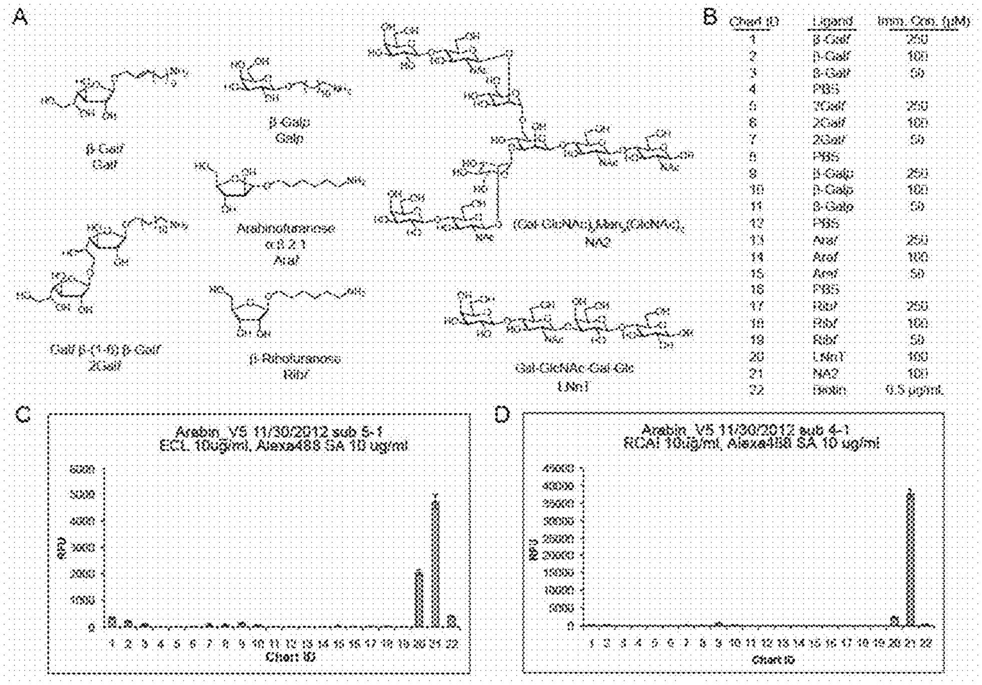
| Chart ID | Ligand | Imm. Con. (μM) |
|---|---|---|
| 1 | β-Galf | 250 |
| 2 | β-Galf | 100 |
| 3 | β-Galf | 50 |
| 4 | PBS | |
| 5 | 2Galf | 250 |
| 6 | 2Galf | 100 |
| 7 | 2Galf | 50 |
| 8 | PBS | |
| 9 | β-Galp | 250 |
| 10 | β-Galp | 100 |
| 11 | β-Galp | 50 |
| 12 | PBS | |
| 13 | Araf | 250 |
| 14 | Araf | 100 |
| 15 | Araf | 50 |
| 16 | PBS | |
| 17 | Ribf | 250 |
| 18 | Ribf | 100 |
| 19 | Ribf | 50 |
| 20 | LNnT | 100 |
| 21 | NA2 | 100 |
| 22 | Biotin | 0.5 μg/mL |
FIGS. 10A-D

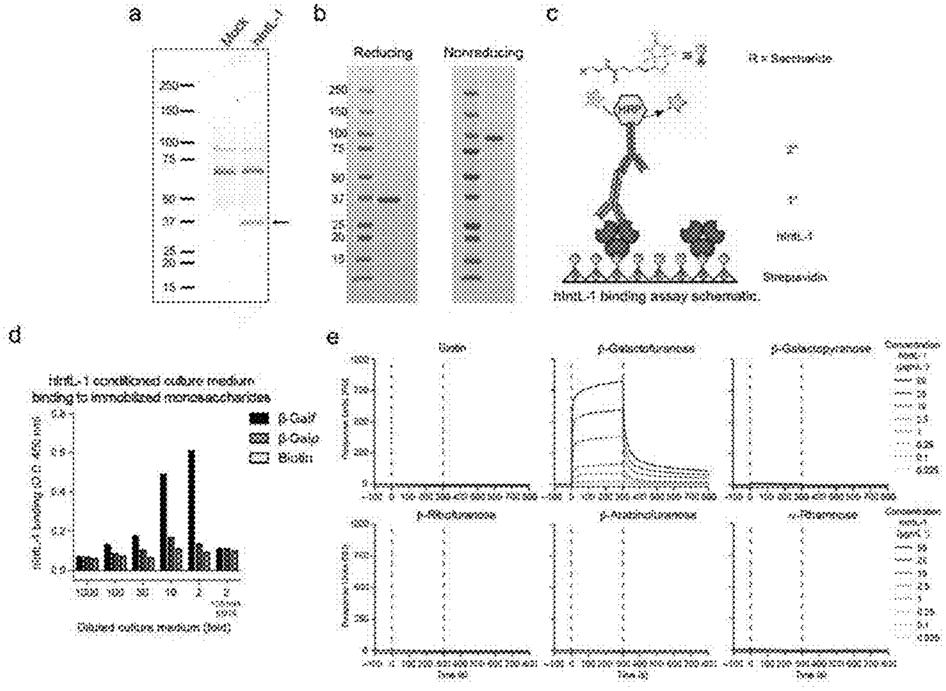
FIGS. 11A-E

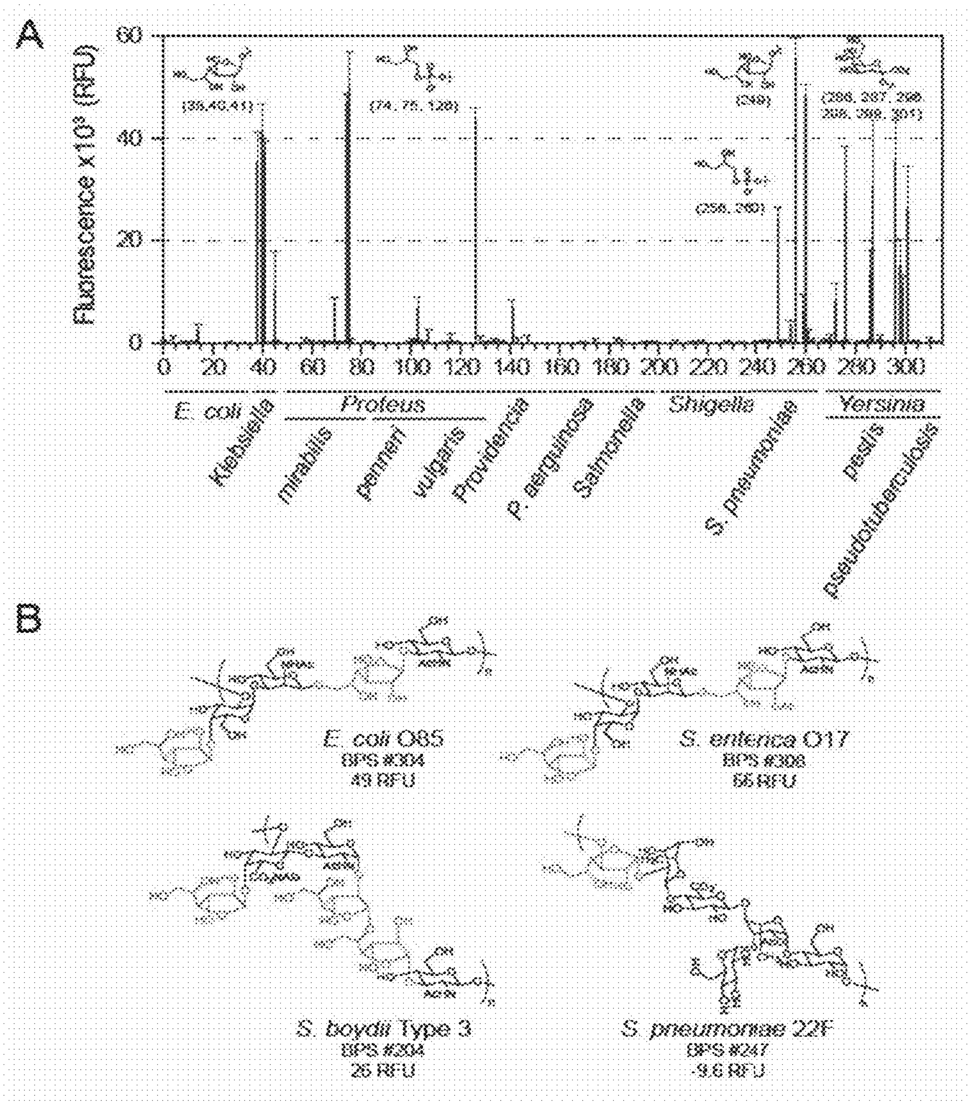
FIGS. 12A-B

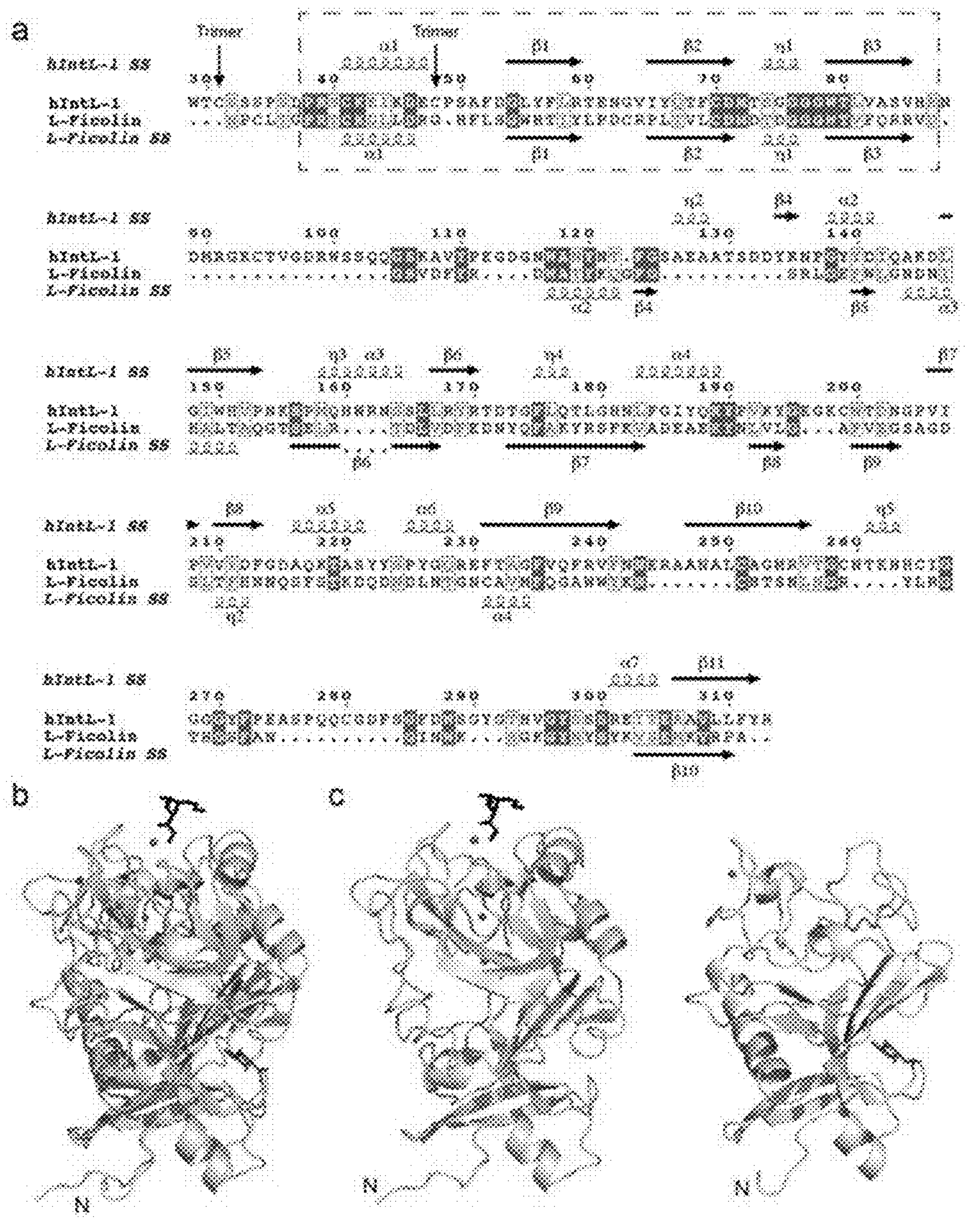
FIGS. 13A-C

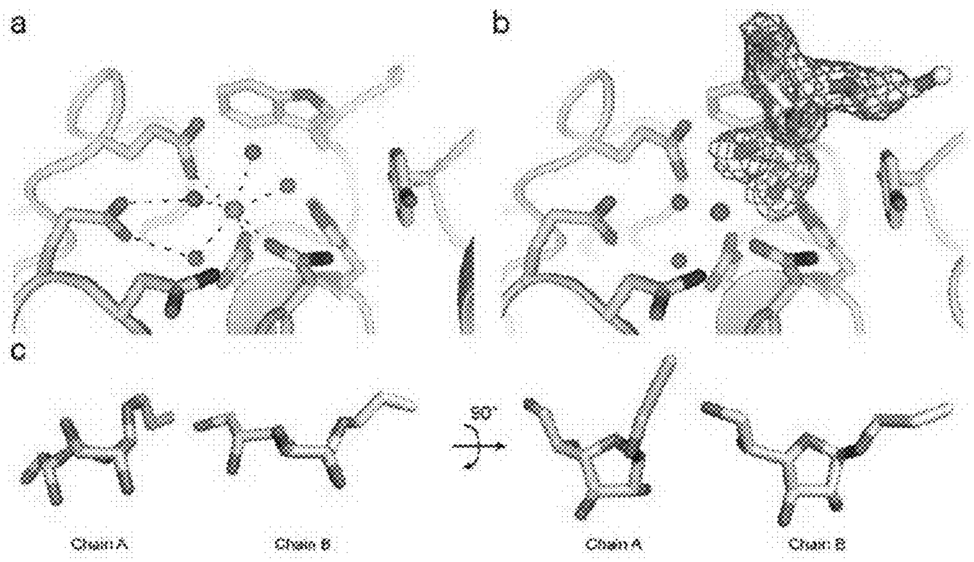

d

| | Chain A | Chain B |
|---|---|---|
| Chain in 4WMY | A | B |
| N-Termini | Intermolecular disulfide bond and connecting peptide visible | Three residues prior to intermolecular disulfide visible, interconnecting peptide not visible |
| Figures used | 3a, Supplementary Figure 3b, 3c, 4c | 3b, Supplementary Figure 4b, 4c, 5a, 5b, 5c |
| Furanoside conformation | $^{4}T_{3}$, Calculated P = 105° | $^{4}E$, Calculated P = 57° |
| Exocyclic diol dihedral | 45° | 51° |
| Galf conformation | $^{4}T_{3}$-gg-gt | $^{4}E$-gg-gt |

FIG. 14A-D

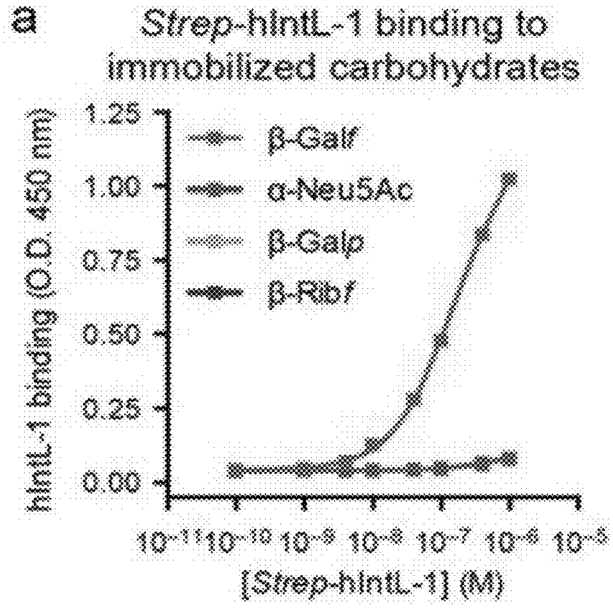
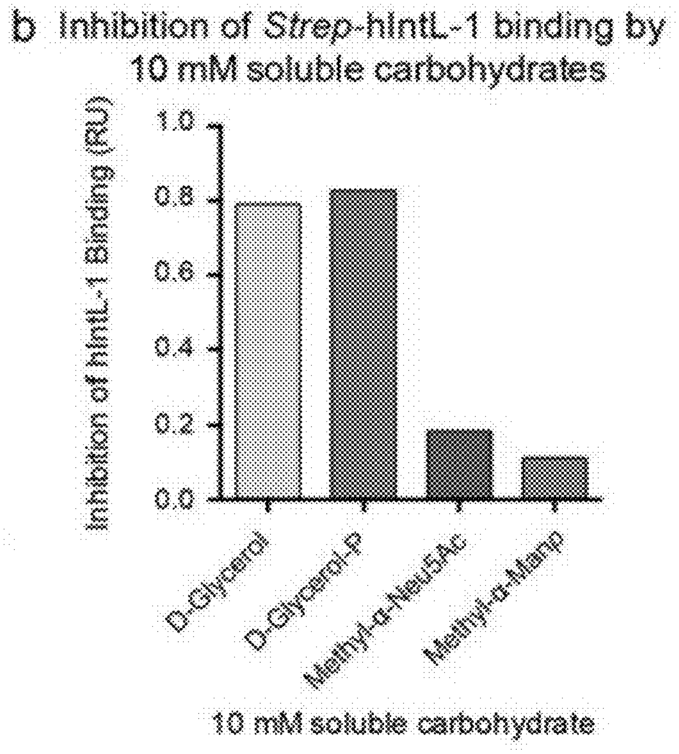
FIG. 15A-B hIntL-1

Blue = Structural Ca site

Magenta = Ligand binding site

Blue = Structural Ca site

Magenta = Ligand binding site

XEEL

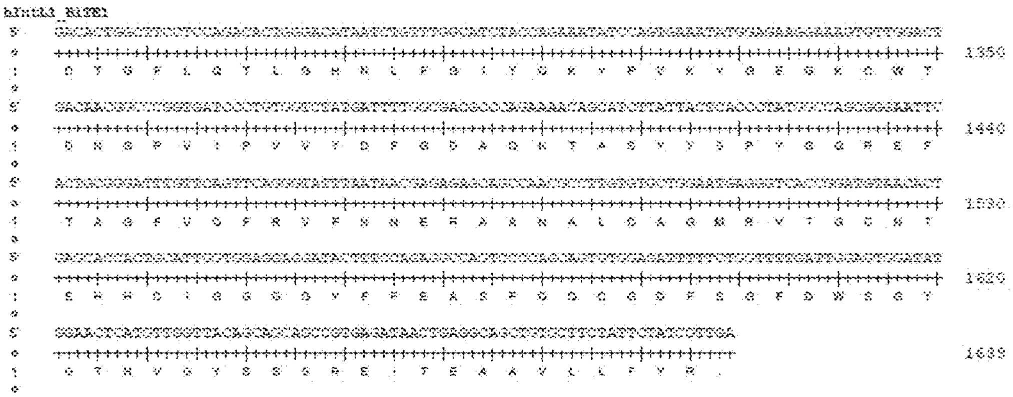
FIG. 19, cont'd

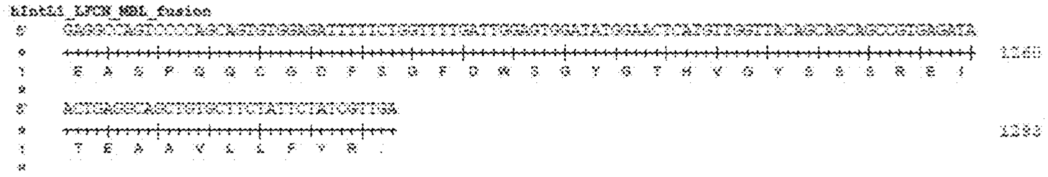
FIG. 21, cont'd

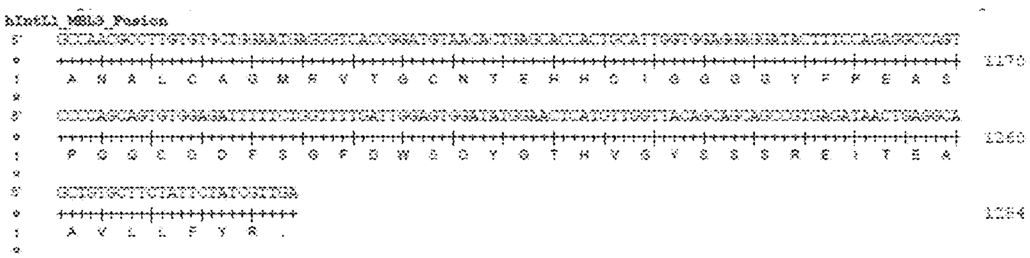
FIG. 24, cont'd

MICROBIAL GLYCANS AS A TARGET OF HUMAN INTELECTIN

This application claims benefit of priority to U.S. Provisional Application 62/075,369, filed Nov. 5, 2014, the entire contents of which are hereby incorporated by reference.

This invention was made with government support under AI063596 awarded by the National Institutes of Health. The government has certain rights in the invention.

BACKGROUND

1. Field

The present disclosure relates generally to the fields of biology and medicine. More particularly, it concerns molecular interactions between human intelectins and microbial glycans. Specifically, the disclosure relates to the use of intelectins to identify and inhibit microbes.

2. Description of Related Art

Mammals place glycans on their cell surfaces that differ markedly from many of those present on microbes. Lectins that selectively recognize microbial glycans would be useful to distinguish between host and microbe, but the human lectins described to date can interact with human glycans. All cells are covered with a coat of glycans. Differences in the glycan coat can serve as markers of a cell's identity—its developmental state, its tissue type, or whether it is self- or non-self. To specifically recognize differences in glycosylation, humans use carbohydrate binding proteins, or lectins. The importance of glycosylation to human health is highlighted by the fact that 1-2% of the genes of any organism encode for enzymes predicted to be involved in glycosylation. Indeed, glycans are key biomolecules of molecular recognition.

Intelectins are a newly discovered class of animal lectins not similar to known C-type lectins (Drickamer, 1993), but nevertheless in many cases having been shown to bind carbohydrates in a calcium-dependent manner. The first intelectin protein was identified in *Xenopus laevis* oocytes and assigned the name XL-35 (Lee et al., 1997). Since then, homologs have been identified in a wide variety of animals; notable examples include lamprey, trout, sheep, mice and humans. Homologs of hIntL-1 are found in all mammals, suggesting that hIntL-1 is used by the hosts to identify microbial guests. Although intelectin family members share a high degree of sequence identity (FIGS. 5A-B), only a small 45 residue (residues 37-82 in hIntL-1 (Tsuji et al., 2001)) fibrinogen-like domain (FBD) shares sequence similarity to other proteins (Thomsen et al., 2011). In addition to intelectins, the FBD is found in other lectins, the best studied being innate immune lectins from the ficolin family. However, the predicted domain architecture and primary sequence differ significantly between intelectins and ficolins (FIGS. 6A-B).

SUMMARY

Thus, in accordance with the present disclosure, there is provided a method for detecting the presence of a microorganism comprising (i) contacting a sample or an environment suspected of containing the microorganism with a human intelectin molecule, and (ii) detecting binding of the human intelectin molecule to the microorganism. The microorganism may be a bacterium or a fungus. The bacterium may be *Streptococcus pneumonia, Proteus mirabilis, Proteus vulgaris, Klebsiella pneumonia* or *Yersinia pestis*. The fungus may be *Cryptococcus neoformans* or *Aspergillus fumigatus*. The microorganism may express a glycan molecule containing a vicinal 1,2-diol.

The human intelectin may bind to a β-linked D-galactofuranose residue, a glycan containing a heptose, D-glycero-D-talo-oct-2-ulosonic acid (KO) and/or 3-deoxy-D-manno-oct-2-ulosonic acid (KDO) residue, and/or a saccharide residue modified with a phospho-glycerol (Gro-P) substituent. The human intelectin, or a variant thereof, may be conjugated to a label or reporter. The sample or environment may contain human glycans. The sample may comprise a human tissue or body fluid, such as blood or serum. The sample may comprise a water or waste sample. The human intelectin molecule may be immobilized on a support, such as a dipstick, bead, chip, microwell, filter, resin, membrane, or quantum dot. The human intelectin molecule may be a truncated version of wild-type hIntL-1 that retains glycan-binding function. The human intelectin molecule may be a substitution mutant version of wild-type hIntL-1 that retains glycan-binding function. The human intelectin may be hIntL-1 or hIntL-2.

In another embodiment, there is provided a method of inhibiting the growth of a microorganism comprising contacting the microorganism or an environment containing the microorganism with a human intelectin molecule conjugated to an antimicrobial, an antibiotic or an immune beacon. The microorganism may be a bacterium, such as *Streptococcus pneumonia, Proteus mirabilis, Proteus vulgaris, Klebsiella pneumonia* or *Yersinia pestis*. The microorganism may be fungus, such as *Cryptococcus neoformans* or *Aspergillus fumigatus*. The microorganism may express a glycan molecule containing a vicinal 1,2-diol. The microorganism may be located in or on a living subject.

The antimicrobial, antibiotic or immune beacon may be located in or on a microsphere to which the human intelectin molecule is conjugated. The immune beacon may be a peptide sequence that that activates complement or that is targeted by T-cells. The human intelectin may bind to a β-linked D-galactofuranose, a glycan containing a heptose, D-glycero-D-talo-oct-2-ulosonic acid (KO) and/or 3-deoxy-D-manno-oct-2-ulosonic acid (KDO) residue, and/or a saccharide residue modified with a phospho-glycerol (Gro-P) substituent. The human intelectin may be hIntL-1 or hIntL-2. The human intelectin may be mannosoylated to direct it, when bound to a microorganism, to other innate immune cells such as dendritic cells.

In still another embodiment, there is provide a fusion protein comprising (a) at least that portion of a human intelectin that binds to microbial glycan and (b) a peptide sequence that activates complement or that is targeted by T-cells. The microbial glycan may contain a vicinal 1,2-diol. The fusion protein may further comprise a linker disposed between (a) and (b). The at least a portion of human intelectin may comprise hIntL-1 sequences. The fusion protein may further comprise a purification tag. The peptide sequence may be all or part of a ficolin, such as L-ficolin or mannan-binding lectin.

Another embodiment comprises a nucleic acid construct encoding a fusion protein as set forth above, an expression vector containing such a construct, or a host cell containing such a vector.

Also provided is method of purifying a human intelectin comprising (a) contacting a sample containing the human intelectin with a support comprising a linear carbohydrate or carbohydrate comprising an exocyclic diol under conditions permitting binding of the human intelectin to said linear carbohydrate; and (b) eluting the human intelectin from said support. The eluting may comprise treating said support with EDTA or an excess of a exocyclic diol containing compound such a glycerol or sorbitol. The support may be a resin column. The carbohydrate may be galactofuranose or sorbitol. The binding in step (a) may be calcium dependent. The resin column may be a sepharose resin comprising sorbitol linked through a divinyl sulfone group.

Another embodiment comprises method of detecting a bacterium or mixture of bacteria in a sample comprising (a) contacting said sample with an intelectin; and (b) detecting the binding of said intelectin to a bacterium or mixture of bacteria in said sample. The sample may be a fecal sample, a blood sample, a saliva sample, a mucousal fluid sample, a lung aspirate sample, an eye wash sample, or a urine sample. The intelectin may be human intelectin-1, human intelectin-2 or mouse intelectin-1. Step (b) comprises flow cytometry, wherein a label associated with said intelectin is detected. The result of step (b) may be compared to a standard, such as a comparable result from a healthy subject, or a comparable result from a diseased subject. The diseased subject may have an infection. Step (b) may further comprise quantitation of said bacterium or bacterial mixture, and/or taxonomic identification of said bacterium or bacterial mixture. The sample may be a probiotic sample.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Structure of ligands used for characterization of hIntL-1 by ELISA and SPR. (FIG. 1B) The specificity of hIntL-1 for β-Galf, β-ribofuranose and β-galactopyranose was tested in an ELISA. Error bars represent the s.d. of the mean (n=3). (FIG. 1C) Affinity of hIntL-1 for carbohydrate ligands as measured in the ELISA. Affinities are reported as apparent Kd as they are calculated for the hIntL-1 disulfide-linked trimer, which can engage in multivalent binding (below). (FIG. 1D) SPR sensorgrams of hIntL-1 binding to immobilized carbohydrates. Complete data set is available in FIG. 9.

(FIG. 2A) Recombinant hIntL-1 binding to mammalian glycan microarray CFG v5.1 and a custom furanoside array. Error bars represent the standard deviation of the mean (n=4). (FIG. 2B) Recombinant IntL-1 ligands were identified using the microbial glycan array. The glycan array data are organized by genus in FIGS. 12A-B. Error bars represent the standard deviation of the mean (n=4). (FIG. 2C) Top 15 ligands identified in the microbial array. Species are designated to provide a sense of the breadth of hIntL-1 recognition. Of the top 15, *Y. pestis* KM260(11)-Δ0187 and KM260 (11)-6C are the only uncharacterized glycans. (FIG. 2D) Structural representation of the proposed ligands of hIntL-1 and which microbial glycans they are present in in FIG. 2C. All of the ligands identified here have an exocyclic vicinal diol. L,D-α-heptose has an epimer, D,D-α-heptose with opposite sterochemisty at C(6). N-Acetylneuraminic acid (Neu5Ac) is included to depict its acyclic vicinal diol.

(FIG. 3A) Structure of the hIntL-1 disulfide-linked trimer complexed with allyl-β-D-Galf. Each monomer unit is depicted in a different color, while the β-Galf ligand is in black, calcium ions in green, and ordered water molecules in red. Two orientations are shown to indicate the relative positioning of the ligand-binding sites within the trimer. (FIG. 3B) Close-up of the ligand binding site. Residues involved in calcium coordination and ligand binding are highlighted using the three letter amino acid code.

(FIG. 5A) Graphic representation of intelectin protein primary sequences aligned using Clustal W (hIntl-1=SEQ ID NO: 1; hIntl-2=SEQ ID NO: 2; mIntl-1=SEQ ID NO: 3; mIntl-2=SEQ ID NO: 4; sIntl-1=SEQ ID NO: 5; XIntl-1=SEQ ID NO: 6). The consensus sequence is represented on the top (SEQ ID NO: 7). Resides identical in every sequence are denoted with a red box. (FIG. 5B) Percentage sequence identity between intelectin proteins depicted in FIG. 5A.

(FIG. 6A) Graphic representation of intelectin and ficolin protein primary sequences aligned using Clustal W (hIntl-1=SEQ ID NO: 1; mIntl-1=SEQ ID NO: 3; XIntl-1=SEQ ID NO: 6; h H-Ficolin =SEQ ID NO: 8; h L-Ficolin =SEQ ID NO: 9; h M-Ficolin=SEQ ID NO: 10). The consensus sequence is represented on the top (SEQ ID NO: 11). Resides identical in every sequence are denoted with a red box. Ficolin proteins contain a collagen-like domain near the N-terminus that is not present in intelectins, this region is highlighted with a box. (FIG. 6B) Percentage sequence identity between intelectin and ficolin proteins depicted in FIG. 6A. While both families of proteins are similar internally, intelectins and ficolins are divergent.

(FIG. 7A) Silver staining of a reducing SDS-PAGE analysis of hIntL-1 transfected conditioned culture media. These samples were taken 48 hours post transfection. hIntL-1 is indicated by the arrow. (FIG. 7B) Coomassie stained reducing and nonreducing SDS-PAGE analysis of hIntL-1 purified on an immobilized β-Galf column. The molecular weight of hIntL-1 when analyzed under nonreducing conditions is indicative of a disulfide-linked homotrimer.

(FIG. 8A) Schematic of streptavidin based ELISA-like carbohydrate binding assay developed for assessing hIntL-1 ligand specificity. Any biotin functionalized carbohydrate can be immobilized and assayed. (FIG. 8B) hIntL-1 conditioned HEK culture media dose dependently binds β-Galf. Addition of 25 mM EDTA completely abolished binding. Error bars represent the standard deviation (n=2) of a technical replicate.

FIGS. 10A-D. Construction of a Furanoside Glycan Array. (FIGS. 10A-B) Chemical structure of amine functionalized carbohydrates used in the furanoside glycan array. Carbohydrates were immobilized at varying density on an NHS-ester activated glass coverslip according to standard protocols. NA2 and LNnT served as positive controls for immobilization. (FIG. 10B) The identity and ligand density of each spot on the furanoside array is shown for ease of analysis. (FIGS. 10C-D) Specific recognition of LNnT and NA2 by *Erythrina cristagalli* lectin (ECL; FIG. 10C) and *Ricinus communis* agglutinin I lectin (RCAI; FIG. 10D) confirm the printing efficiency of the array.

FIGS. 11A-E. Expression, purification and carbohydrate binding activity of hIntL-1. (FIG. 11A) Reducing SDS-PAGE analysis of HEK 293T culture medium from hIntL-1 transfected cells. Samples were analyzed by silver stain 48 hours post transfection. An arrow indicates the band corresponding to the molecular weight of a hIntL-1 reduced monomer. (FIG. 11B) Coomassie stained gels of samples subjected to reducing and nonreducing SDS-PAGE analysis of hIntL-1 purified on an immobilized β-Galf column. The molecular weight of the sample analyzed under non-reducing conditions corresponds to that of a disulfide-linked hIntL-1 homotrimer. (FIG. 11C) Schematic of streptavidin-based, ELISA-like carbohydrate binding assay developed for assessing hIntL-1 ligand specificity. Biotinfunctionalized carbohydrate is immobilized. Bound hIntL-1 is detected the enzyme horseradish peroxidase (HRP) conjugated to an antibody (either a secondary or directly conjugated primary), and a chromogenic HRP substrate. (FIG. 11D) Carbohydrate-binding activity of HEK 293T cell conditioned culture medium following transfection with hIntL-1 expression plasmid. The calcium ion dependence was tested by the addition of 25 mM EDTA. Data are presented as the mean (n=2 of a technical replicate and is representative of >3 independent experiments). (FIG. 11E) Complete data set of hIntL-1 SPR analysis presented in FIG. 1C. β-Ribofuranose and β-arabinofuranose were included as they were reported to be ligands of hIntL-1 (Tsuji et al., 2001). α-Rhamnose was included as a non-human monosaccharide.

FIGS. 12A-B. hIntL-1 Ligand Specificity Revealed by Microbial Glycan Array. (FIG. 12A) Results of the Microbial Glycan Microarray organized by genus and species, alphabetically. The fluorescence values are identical to those presented in FIG. 2B. The chemical epitope that is proposed to be a hIntL-1 ligand is depicted. The chart identification number from this graph is provided in parenthesis below the graphically depicted ligand. Data are presented as the mean±s.d. (n=4 of a technical replicate for each immobilized glycan). The complete data for this experiment are available in Supplementary Table 3. (FIG. 12B) Chemical structures of terminal α-Galf containing glycans that failed to bind hIntL-1. The Galf residues in each glycan are depicted in red. The BPS number (BPS #) that references each glycan (Stowell et al., 2014), and the hIntL-1 signal (from FIG. 2B) are shown.

FIGS. 13A-C. Structural alignment of hIntL-1 and human L-ficolin (PDB 2J3U). (FIG. 13A) Primary protein sequence and secondary structure comparison of hIntL-1 (SEQ ID NO: 12) and L-ficolin (SEQ ID NO: 13)(PDB: 2J3U; Garlatti et al., 2007) generated using ESPript 3.0 (Robert & Gouet, 2014). The figure was produced from a Clustal W alignment of hIntL-1 (residues 29-313) and L-ficolin (Residues 96-313). The residues depicted correspond to those that were resolvable in each protein structure. This alignment omits the collagen-like domain of L-ficolin. The box denotes the proposed fibrinogen-like domain (FBD) of each molecule. A red box highlights identical residues. The cysteine residues from hIntL-1 that are involved in intermolecular trimerization are identified with an arrow. (FIG. 13B) A hIntL-1 monomer (wheat) aligned to a L-ficolin monomer (PDB: 2J3U) (grey) using Gesamt v6.4 (Krissinel, E., 2012). Reported RMSD=3.6 Å for 165 superimposable Cα atoms between the two structures. After the first 165 Cα atoms, the structures are too divergent to assign Cα atoms as superimposable, and they are not included in this calculation. The co-crystallized carbohydrate ligands are depicted to highlight differences in ligand binding sites. The hIntL-1 ligand is shown in black and the L-ficolin ligand is shown in red. Calcium ions are shown in green. Human IntL-1 binds three calcium ions, while L-ficolin binds one. The N-termini are highlighted with an N. (FIG. 12C) The alignment shown in FIG. 13B, except that L-ficolin is translated by 45 Å for clarity. The N-terminus of each monomer is denoted with an N.

FIGS. 14A-D. hIntL-1 bound to allyl-β-D-Galf. (FIG. 14A) Structure of the ligand-binding site in Apo-hIntL-1 (4WMQ). Calcium ions are shown in green, and ordered water molecules in red. Dashed lines highlight functional groups important for the heptavalent coordination of the ligand binding site calcium ion. (FIG. 14B) Close-up view of the ligand-binding site of the β-GalfβhIntL-1 protein structure (4WMY). This image is the same as depicted in FIG. 3B, although surface mesh is depicted around the β-Galf ligand to highlight the ligand electron density. Mesh represents a difference density map (mFo-DFc, 3σ). Calcium ions are depicted in green and ordered waters are shown in red. The ligand O(5) and O(6) hydroxyl groups coordinate to the calcium ion and displace two ordered water molecules. (FIG. 14C) Structural comparison of the crystallized allyl-β-D-Galf ligands. The molecule from Chain A is shown in wheat, while the molecule shown in Chain B is shown in grey. The furanosides were overlaid using the C(2)-C(3) bond and translated apart by 8 Å. (FIG. 14D) Table summarizing Chain A and Chain B in the β-Galf-hIntL-1 protein structure (4WMY).

FIG. 15A-B. hIntL-1 exhibits specificity for microbial glycan epitopes bearing terminal 1,2-diols. (FIG. 15A) hIntL-1 does not bind to immobilized α-Neu5Ac assayed by the ELISA-like carbohydrate-binding assay (FIG. 11C). Data are fit to a one site binding equation (solid lines). Data are presented as the mean (n=2 of a technical replicate and is representative of three independent experiments). (FIG. 15B) Inhibition of hIntL-1 binding to immobilized β-Galf. Four compounds (glycerol, 1-phosphoglycerol, the methyl-α-glycoside of Neu5Ac, and the methyl-α-D-mannopyranoside) were dissolved in binding buffer and included during the hIntL-1 incubation. Binding data shown are relative to a control where no competitor was added to the binding buffer.

Data are presented as the mean (n=2 of a technical replicate and is representative of three independent experiments).

Figure 16A:
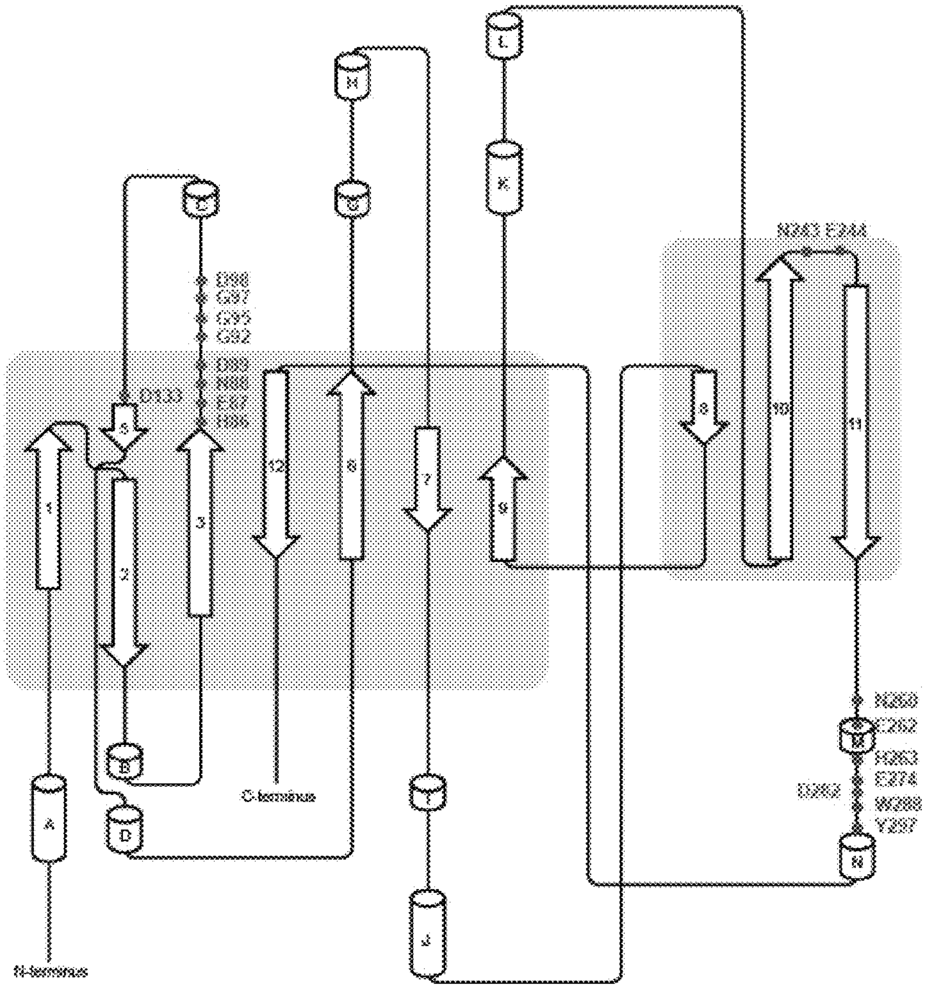
Figure 16B:
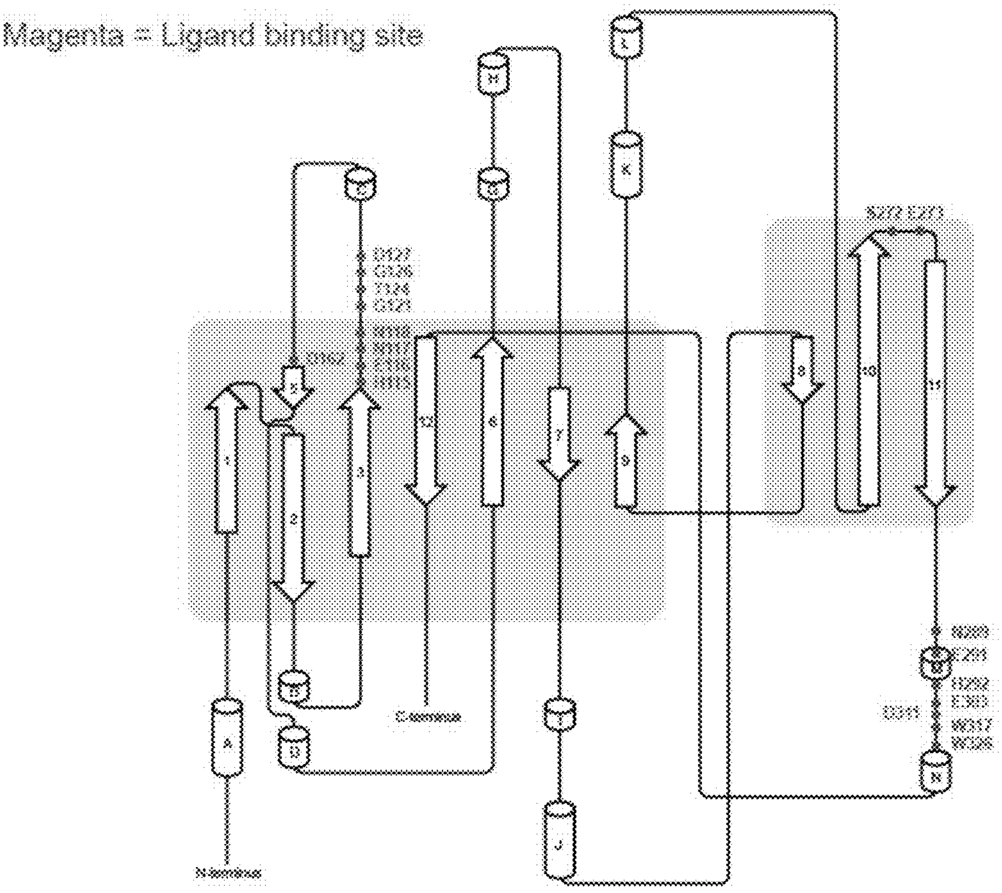

FIGS. 16A-B. Topology diagrams of intelectin proteins. (FIG. 16A) Human intelectin-1 topology diagram. Amino acid residues important for calcium ion coordination and ligand binding are highlighted in blue, and magenta, respectively. (FIG. 16B) *Xenopus laevis* Intelectin-1 (XIntL-1 or XEEL) topology diagram. Amino acid residues important for calcium ion coordination and ligand binding are highlighted in blue, and magenta, respectively.

Figure 17:
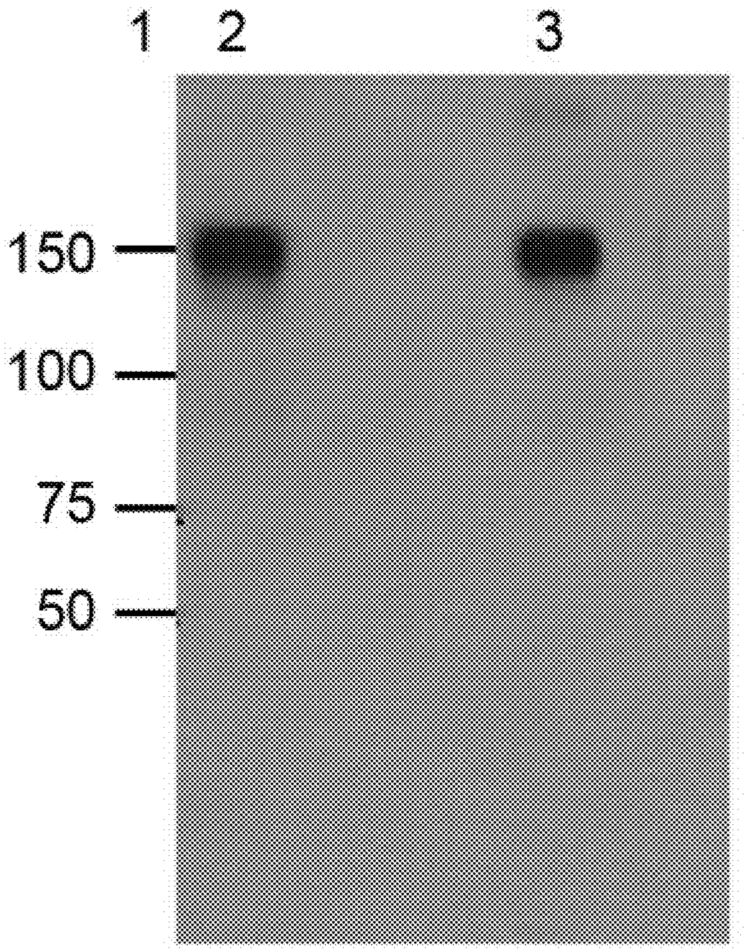

FIG. 17. Expression of MBL/Ficolin hIntL-1 Fusion Constructs. Proteins detected using primary using a sheep IgG anti-hIntL-1 (R&D Systems) primary antibody, and a donkey anti-sheep IgG::HRP (Jackson Immunoresearch) secondary antibody. Lane 1=ladder; Lane 2=hIntL-1_LFCN_MBL_Fusion Conditioned Medium; Lane 3=hIntL-1_MBL3_Fusion Conditioned Medium.

Figure 18:
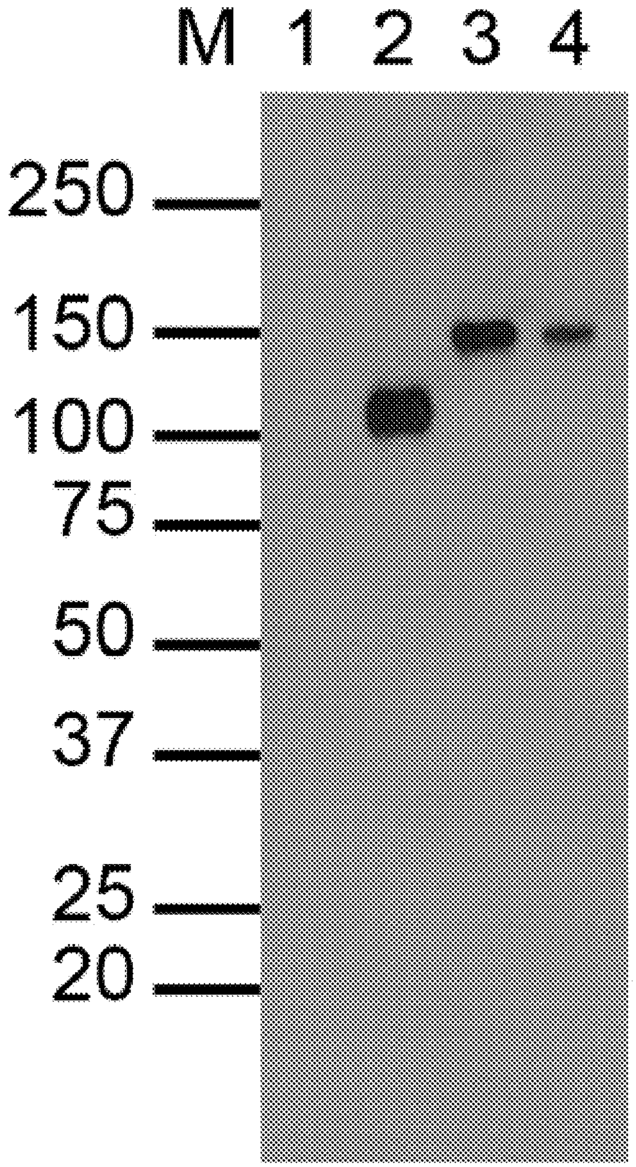

FIG. 18. Non-reducing SDS-PAGE Analysis of Expression Trial Western Blot. Primary anti-Strep-tag::HRP Conjugate. M=protein molecule weight ladder (kDa); 1=no transfection; 2=Strep-hIntL-1; 3=Strep-hIntL-1_LFicolin fusion; 4=Strep-hIntL-1_MFicolin fusion.

Figure 19:
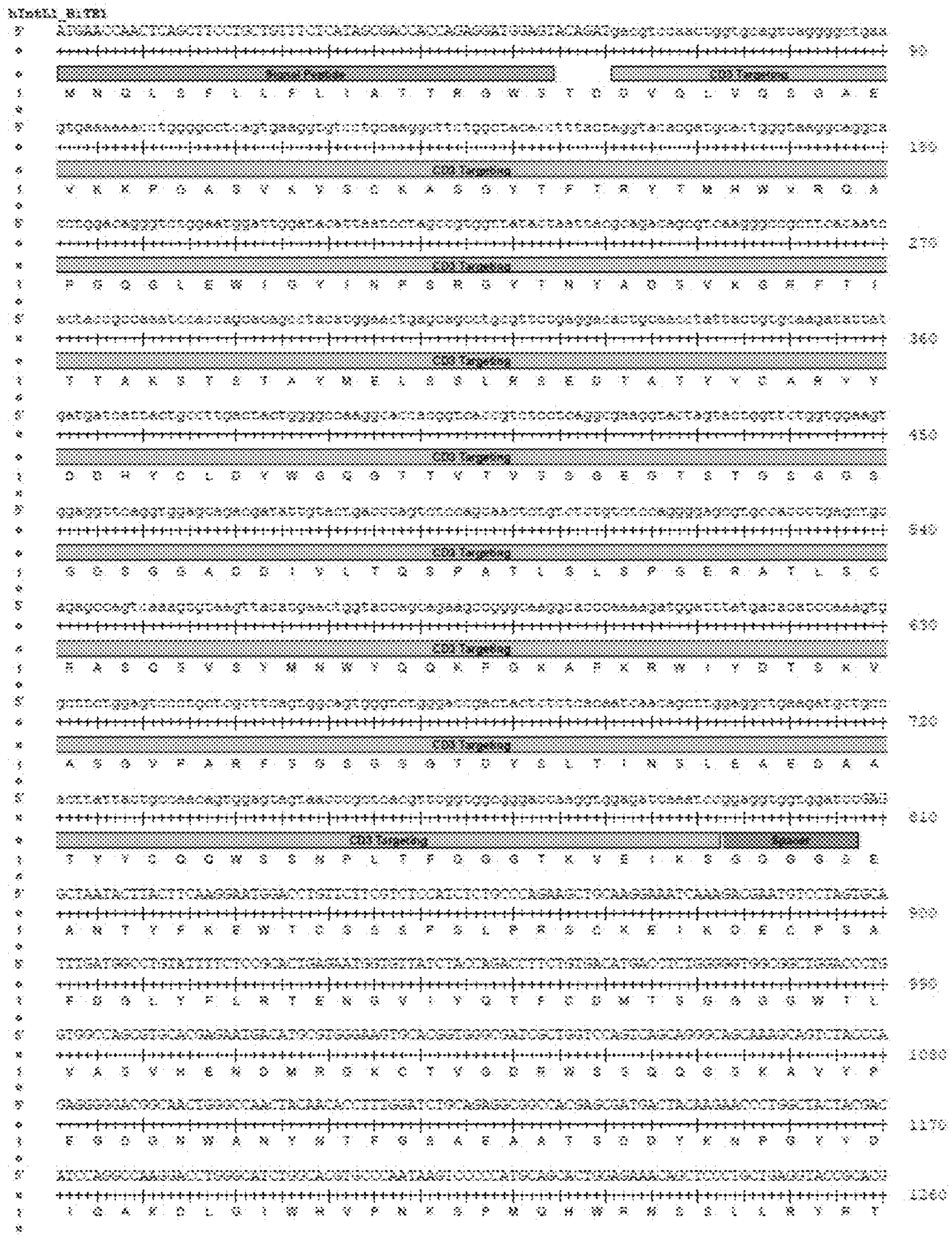

FIG. 19. hIntL1_BiTE_Construct5 (nucleic acid=SEQ ID NO: 14; protein =SEQ ID NO 15).

Figure 20:
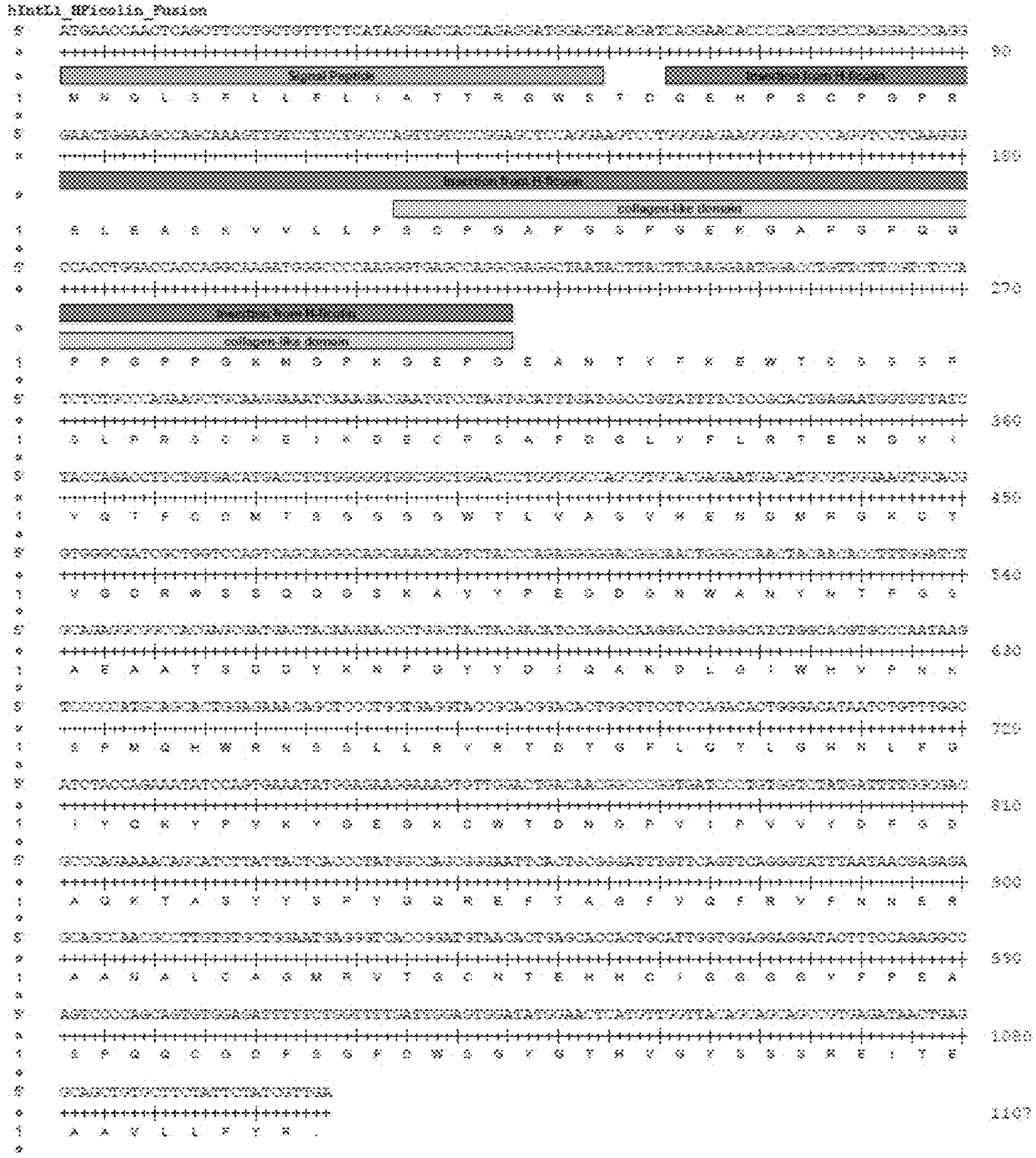

FIG. 20. hIntL1_HFicolin_Construct1 (nucleic acid=SEQ ID NO: 16; protein =SEQ ID NO 17).

Figure 21:
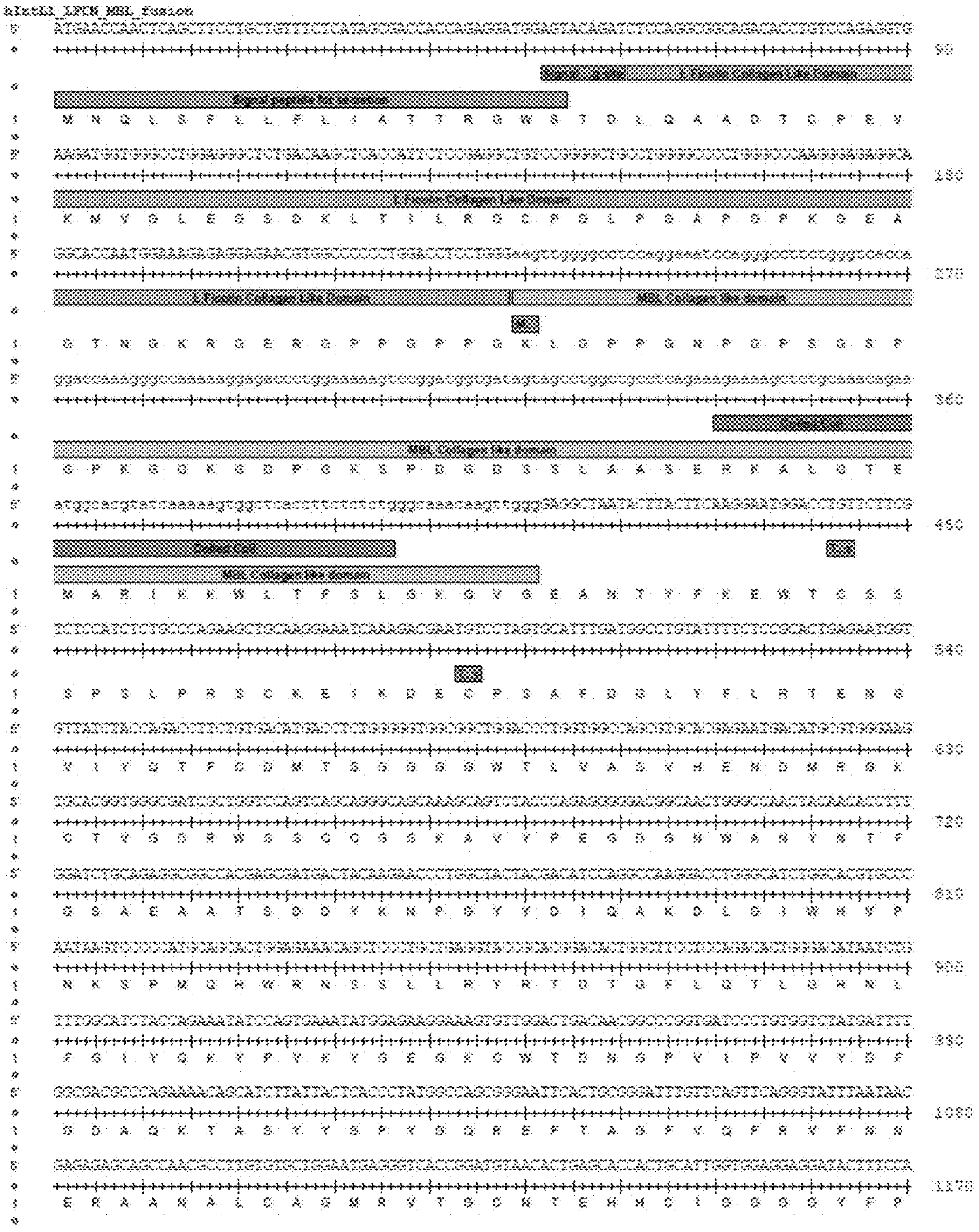

FIG. 21. hIntL1_LFCN_MBL_Fusion(nucleic acid=SEQ ID NO: 18; protein =SEQ ID NO 19).

Figure 22:
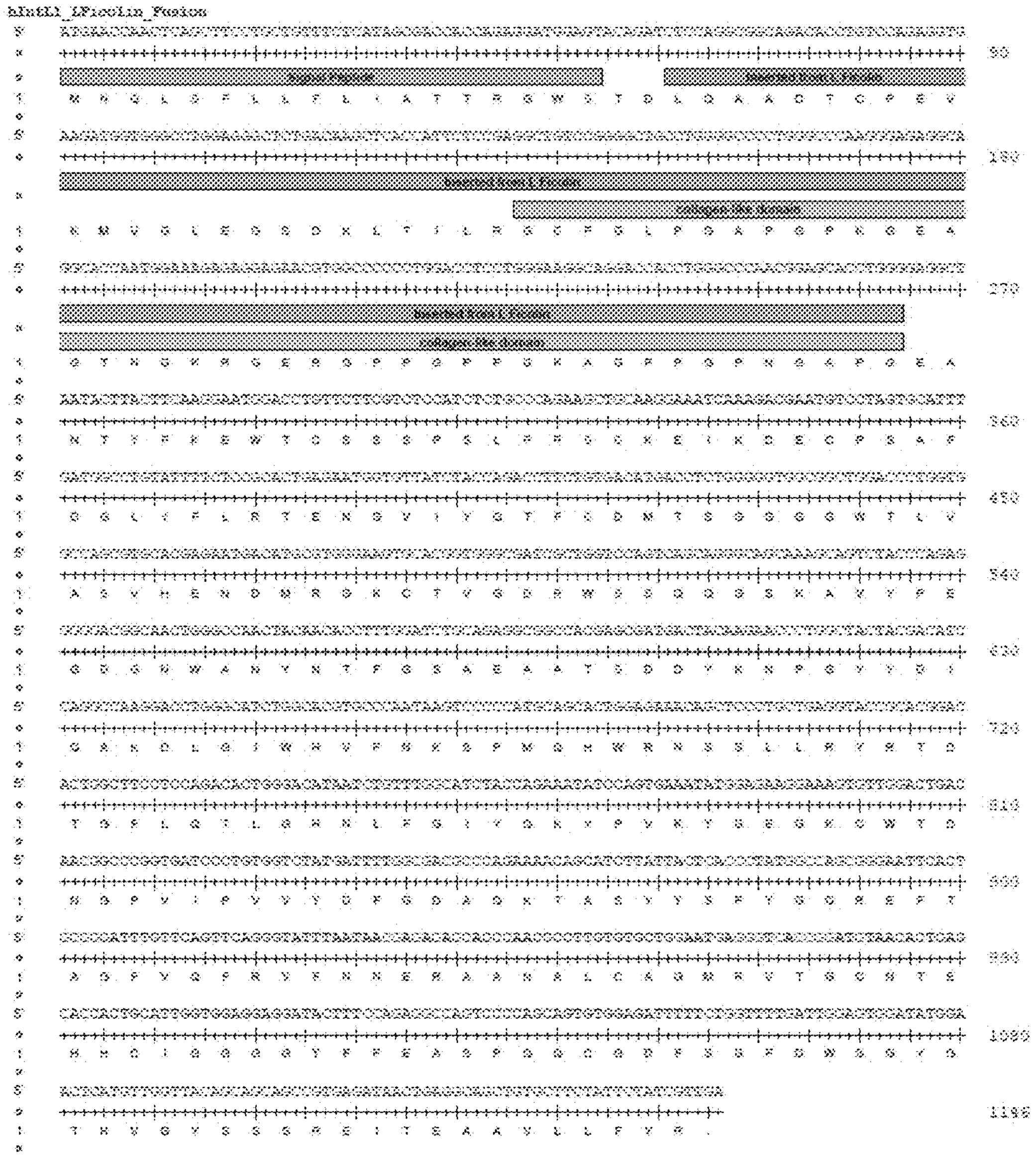

FIG. 22. hIntL1_LFicolin_Fuion_Construct2 (nucleic acid=SEQ ID NO: 20; protein=SEQ ID NO 21).

Figure 23:
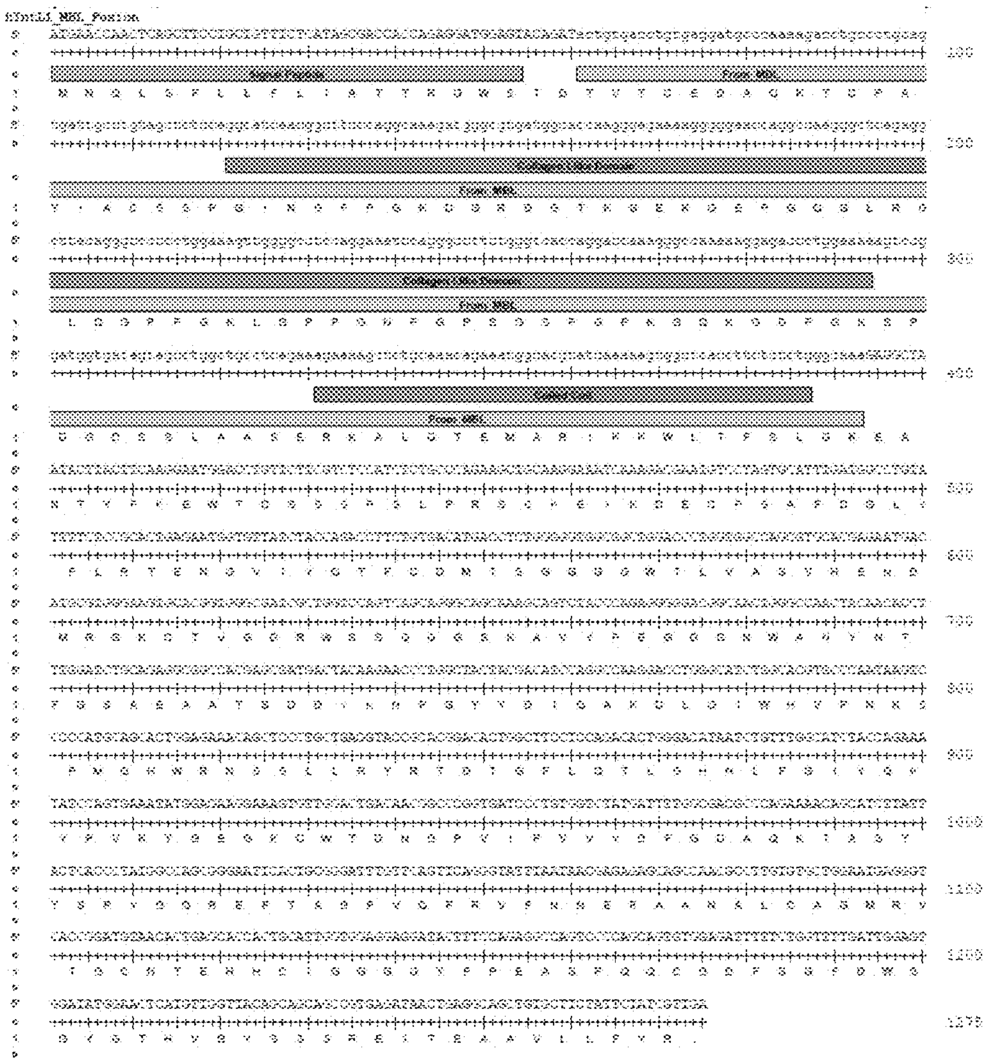

FIG. 23. hIntL1_MBL_Fusion_Construct4 (nucleic acid=SEQ ID NO: 22; protein=SEQ ID NO 23).

Figure 24:
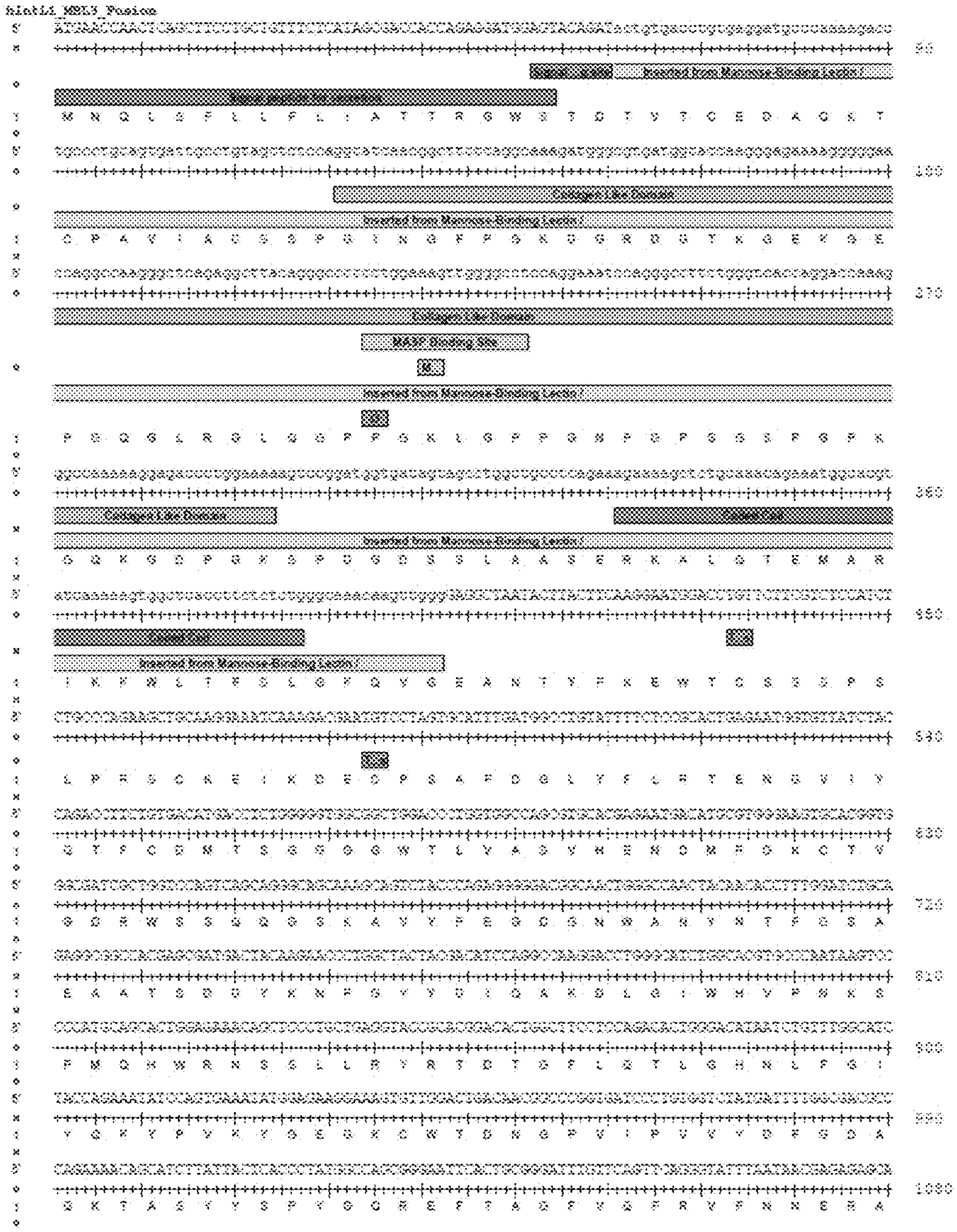

FIG. 24. hIntL1_MBL3_Fusion (nucleic acid=SEQ ID NO: 24; protein=SEQ ID NO 25).

Figure 25:
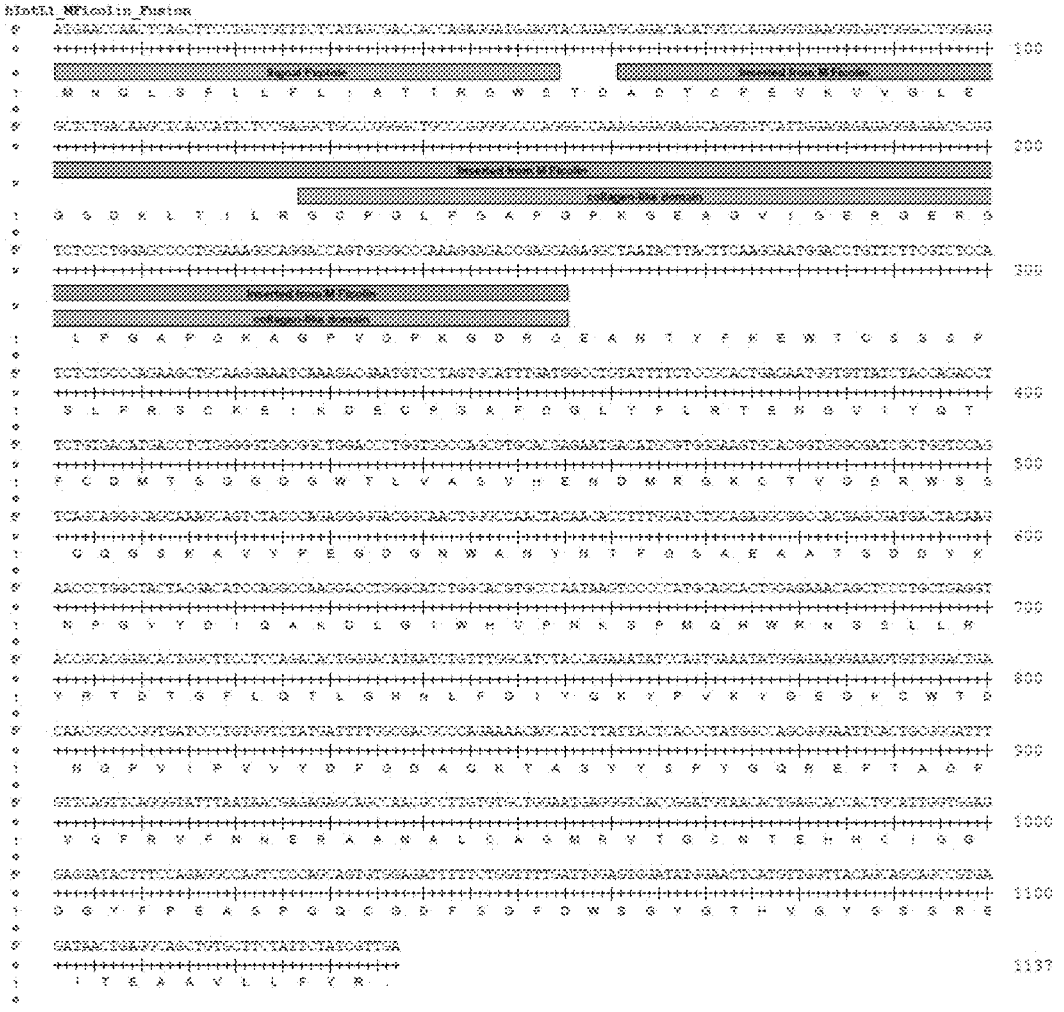
Figure 26A:
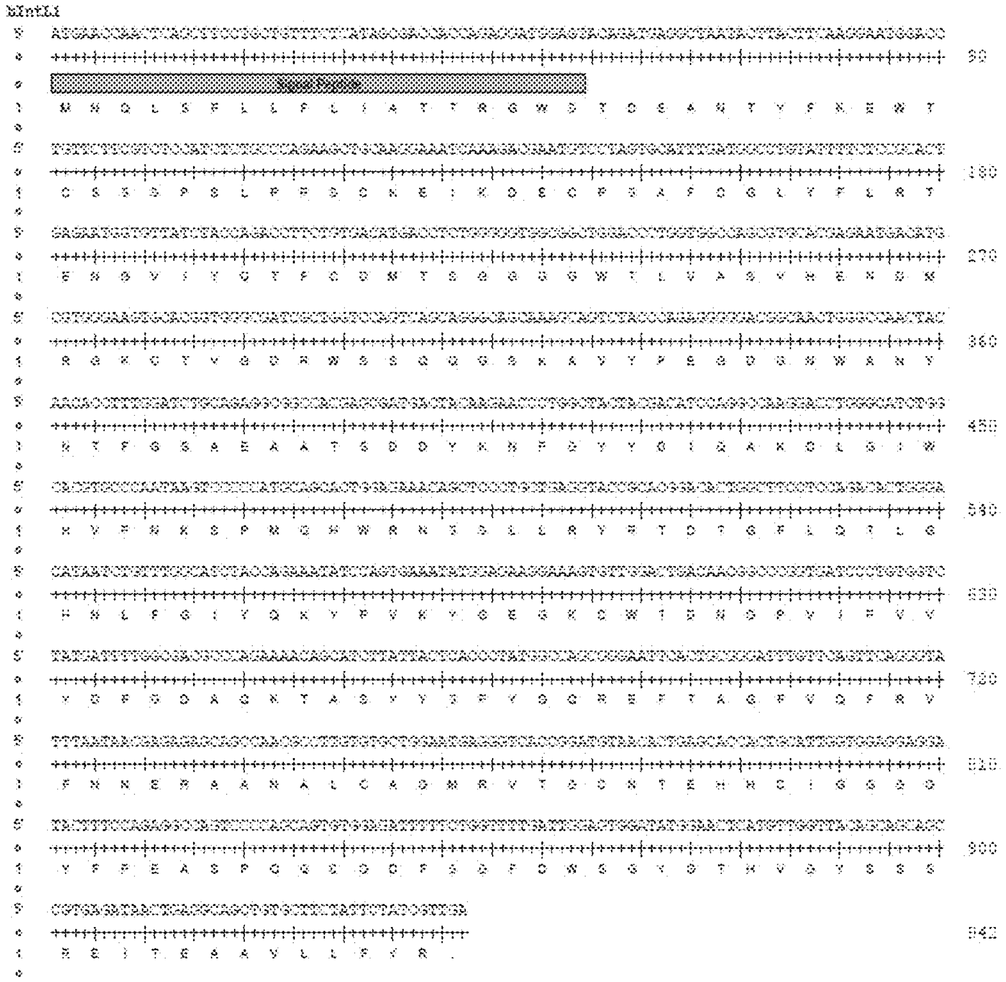
Figure 26B:
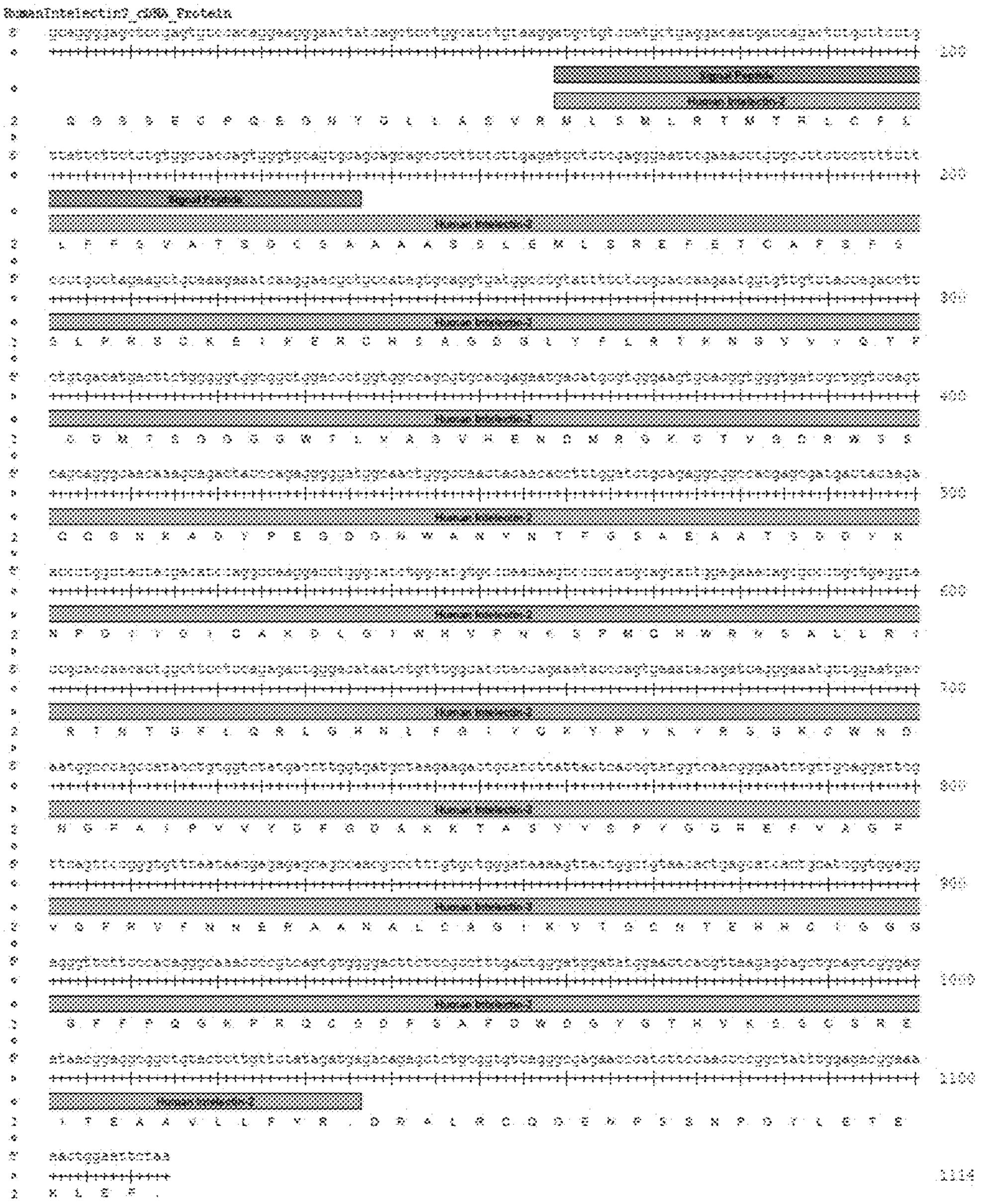
Figure 26C:
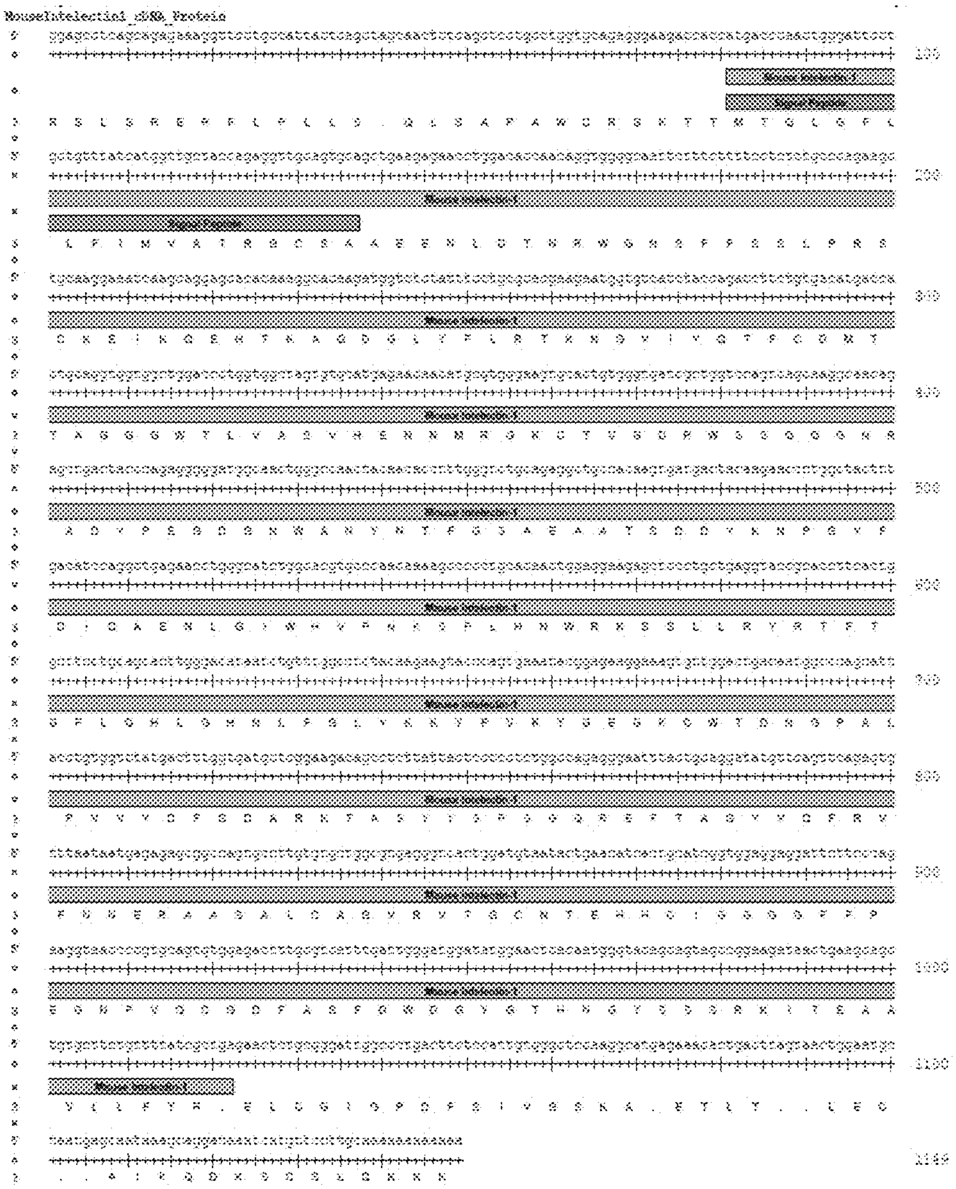
Figure 26D:
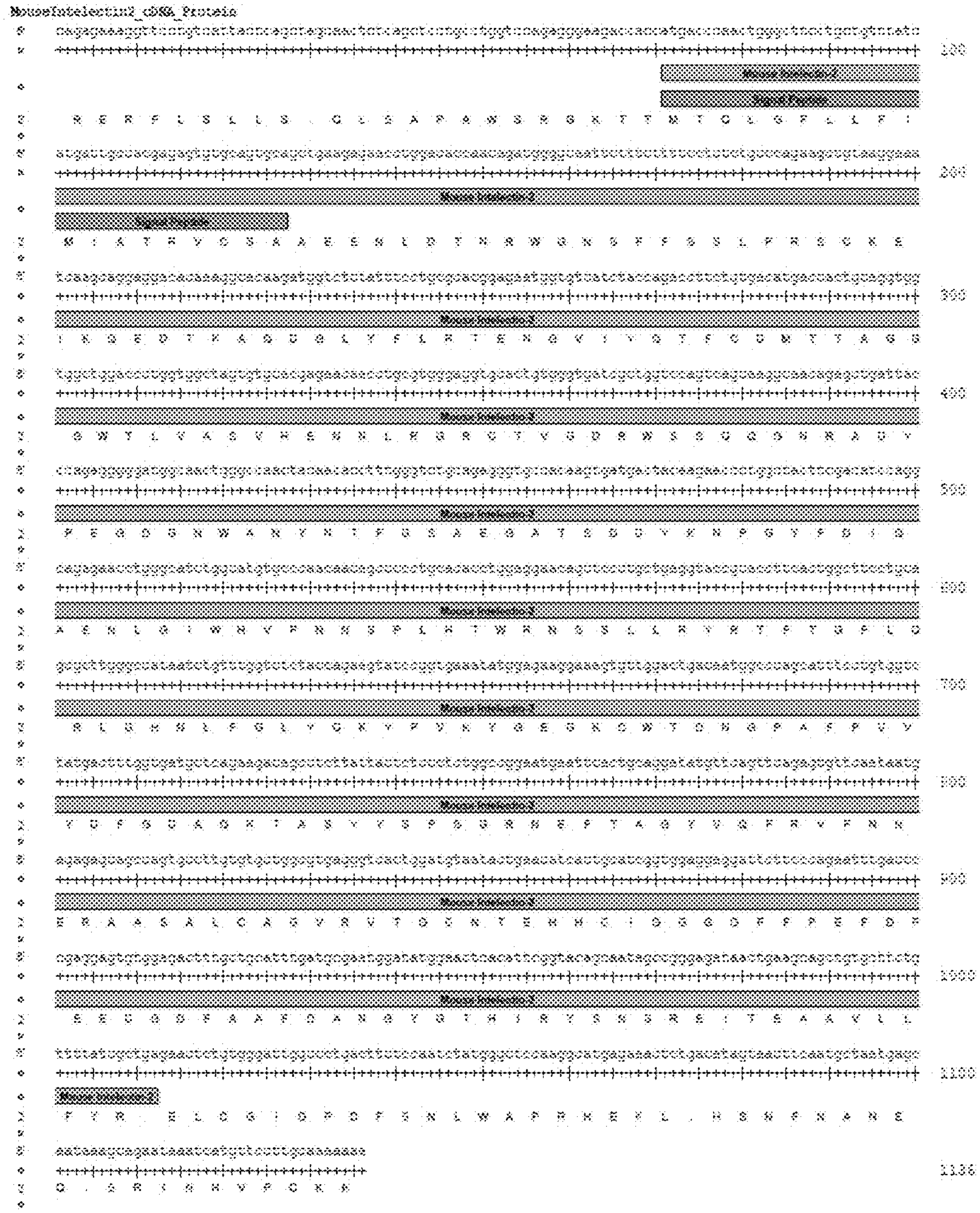

FIG. 25. hIntL1_MFicolin_Fusion_Construct3 (nucleic acid=SEQ ID NO: 26; protein=27).

FIGS. 26A-D. Intelectin sequences. (FIG. 262A) Human intelectin 1 sequences (nucleic acid=SEQ ID NO: 28; protein=SEQ ID NO 1). (FIG. 26B) Human intelectin 2 sequences (nucleic acid=SEQ ID NO: 29; protein=SEQ ID NO 30). (FIG. 26C) Mouse intelectin 1 sequences (nucleic acid=SEQ ID NO: 31; protein=SEQ ID NO 32). (FIG. 26D) Mouse intelectin 2 sequences (nucleic acid=SEQ ID NO: 33; protein=SEQ ID NO 34).

Figure 27:
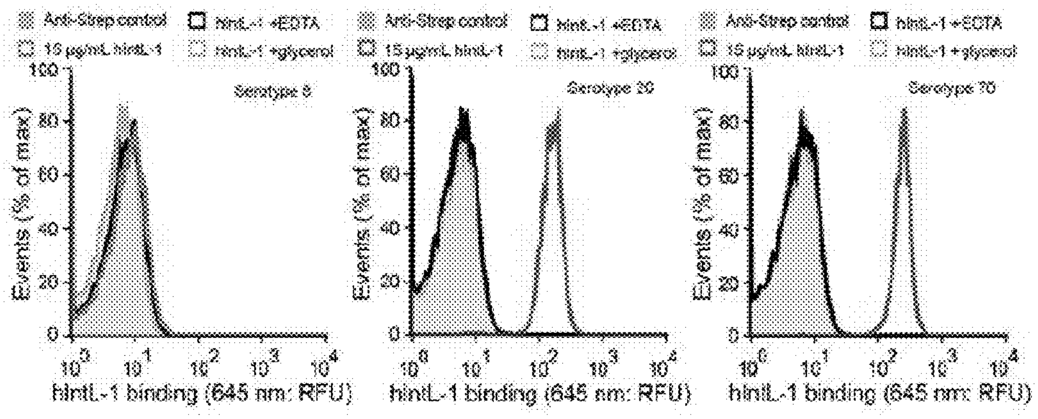

FIG. 27. Specificity of Strep-hIntL-1 for *S. pneumoniae* serotypes. Binding of hIntL-1 to different serotypes of *S. pneumoniae*. Bound hIntL-1 was detected with the addition of an anti-Strep-tag:Oyster 642 nm conjugated antibody. The addition of EDTA and glycerol abrogate binding, supporting a role for calcium ions in 1,2 exocyclic diol recognition. In the anti-Strep control sample, recombinant Strep-hIntL-1 was omitted. All data were collected with identical instrument settings.

Figure 28:
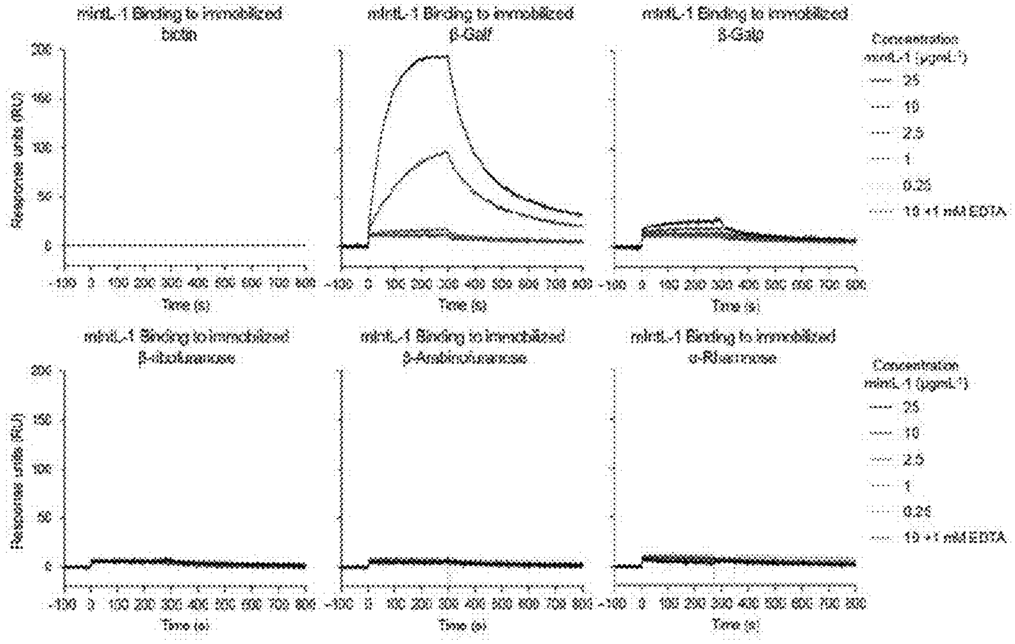

FIG. 28. Mouse intelectin-1 binding to immobilized carbohydrates. Purified Strep-mIntL-1 binding to immobilized carbohydrates monitored using SPR. Addition of EDTA prevents carbohydrate binding, supporting a role for calcium ions in carbohydrate binding. Data are referenced to the biotin channel.

Figure 29:
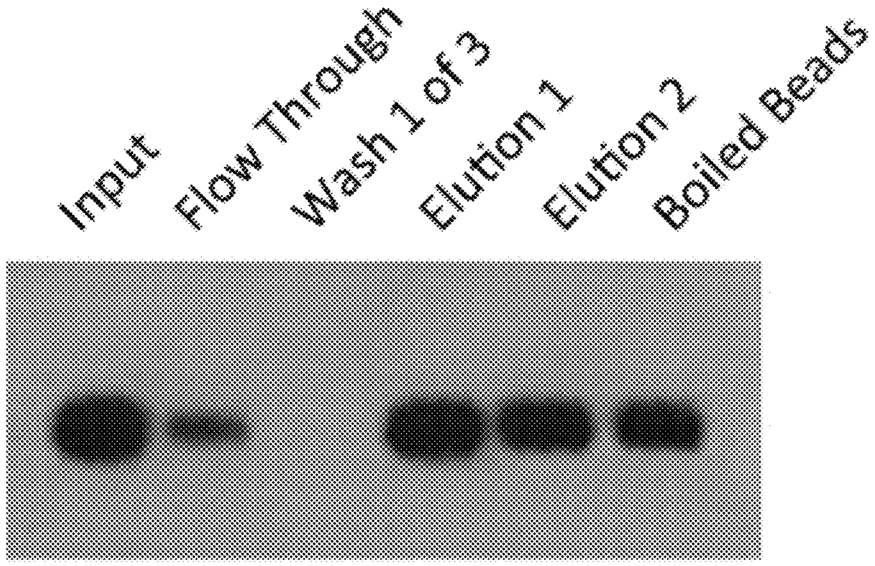

FIG. 29. Representative image of hIntL-1 purification on a sorbitol::sepharose column generated through divinyl sulfone chemistry. Protein was visualized via Western blot using a sheep anti-hntL-1 polyclonal antibody (R&D Systems) and a donkey anti-sheep::HRP conjugate.

DETAILED DESCRIPTION OF ILLUSTRATIVE EMBODIMENTS

The investigators were interested in the specific recognition of non-human glycans by hIntL-1. A lectin that binds in a highly specific manner to Galf would be an invaluable tool for detecting galactofuranosylated biomolecules in complex mixtures. Using biotinylated carbohydrates and an enzyme-linked immunoabsorbent (ELISA) like assay, they showed that trimeric hIntL-1 binds immobilized Galf with an apparent avidity of 85 nM. Unlike previous reports, the investigators showed that hIntL-1 is exceptionally specific for Galf as binding to other immobilized carbohydrate ligands was not detected. To further probe the ligand specificity of hIntL-1, they employed glycan array technology to screen almost 1000 immobilized glycans. Using a custom furanoside array along with the Consortium for Funcational Glycomics (CFG) mammalian glycan array, the investigators produced data suggesting that hIntL-1 does not bind mammalian carbohydrate epitopes. In hindsight, this finding was easily rationalized as the authors later demonstrated that hIntL-1 binds to carbohydrate ligands produced specifically by microbes. They next employed a newly described bacterial pathogen array, and an unexpected affinity toward multiple nonmammalian glycan epitopes was discovered. hIntL-1 exhibits high affinity and selectivity for at least five epitopes displayed on the pathogen array: β-linked D-galactofuranose residues (Galf), D-phosphoglycerol-modified glycans, heptoses, D-glycero-D-talo-oct-2-ulosonic acid (KO) and 3-deoxy-D-manno-oct-2-ulosonic acid (KDO) containing glycans. To further understand carbohydrate binding and the biological role of hIntL-1, the investigators solved the X-ray crystal structure of hIntL-1 to 1.8 Å resolution. This is the first structural information available for the intelectin family of proteins. The investigators believe that these results represent the first example of a human lectin that is orthogonal to the human glycome. These and other aspects of the disclosure are discussed in detail below.

I. Intelectins

Mammals place glycans on their cell surfaces that differ markedly from many of those present on microbes. Lectins that selectively recognize microbial glycans would be useful to distinguish between host and microbe, but the human lectins described to date can interact with human glycans. All cells are covered with a coat of glycans. Differences in the glycan coat can serve as markers of a cell's identity—its developmental state, its tissue type, or whether it is self- or non-self. To specifically recognize differences in glycosylation, humans use carbohydrate binding proteins, or lectins. The importance of glycosylation to human health is highlighted by the fact that 1-2% of the genes of any organism encode for enzymes predicted to be involved in glycosylation. Indeed, glycans are key biomolecules of molecular recognition.

Figure 5:
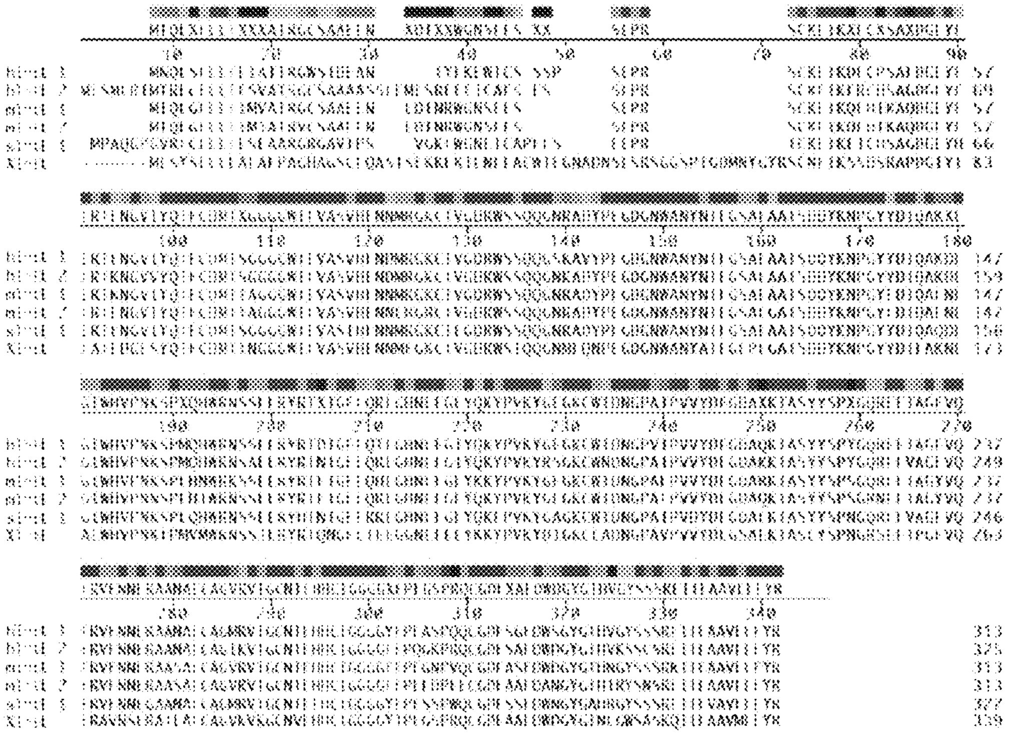
FIGS. 5A-B. Intelectin Protein Primary Sequences are Highly Conserved Across Species.
Figure 6:
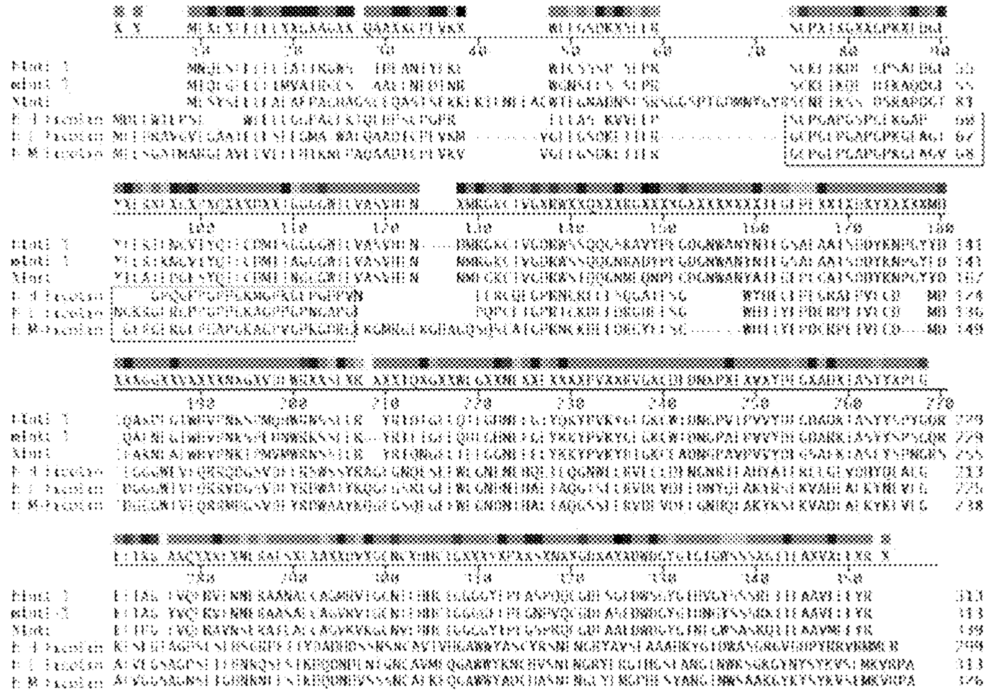
FIGS. 6A-B. Intelectin and Ficolin Proteins are Significantly Divergent Despite Both Containing a Fibrinogen-Like Domain.

Intelectins are a recently discovered class of animal lectins not sequence identical to known C-type lectins (Drickamer, 1993), but in many cases have been shown to bind carbohydrates in a calcium dependent manner. The first intelectin protein was identified in *Xenopus laevis* oocytes and assigned the name XL-35 (Lee et al., 1997). Since then, homologs have been identified in a wide variety of animals; notable examples include lamprey, trout, sheep, mice and humans. Although intelectin family members share a high degree of sequence identity (FIGS. 5A-B), only a small 45-residue (residues 37-82 in hIntL-1 (Tsuji et al., 2001)) fibrinogen-like domain (FBD) shares sequence similarity to other proteins (Thomsen et al., 2011). In addition to intelectins, the FBD is found in other lectins, the best studied being innate immune lectins from the ficolin family. However the predicted domain architecture and primary sequence differ significantly between intelectins and ficolins (FIGS. 6A-B).

Compared to other lectin families, little is known about intelectins biochemically and biologically. There are no definitive experiments that define their carbohydrate binding specificity and no high resolution protein structures available. Mammalian intelectins are expressed by lung and intestinal goblet cells and by intestinal paneth cells. Based on their expression localization and inclusion of a FBD, intelectins are proposed to be lectins of the innate immune system. Expression upregulation of mammalian intelectins in sheep and mice upon infection with intestinal parasitic nematodes support this (Pemberton et al., 2004; Datta et al., 2005; Voehringer et al., 2007; French et al., 2008). Confoundingly, several other biological roles have been suggested for human intelectins independent of their proposed lectin function. Intelectin is proposed to bind lactoferrin and serve as a GPI-anchored intestinal lactoferrin receptor (Suzuki et al., 2001). Studies in humans (Pemberton et al., 2008; Kerr et al., 2014) and mice (Kuperman et al., 2005) have linked intelectin to asthma and airway inflammation. And lastly, intelectin is believed to act as a novel human adipokine, termed omentin, that stimulates insulin-mediated glucose uptake and serves as a predictive biomarker of metabolic disease (Yang et al., 2006). All of these biological roles have been linked to intelectins.

Two human intelectin homologs have been identified; they were termed intelectin-1 and -2 (Lee et al., 2001). The calcium dependent carbohydrate binding activity of hIntL-1 was examined soon after (Tsuji et al., 2001). Data from this study suggested that hIntL-1 promiscuously bound carbohydrate ligands with low affinity. The highest affinity ligand identified was the pentose furanoside, D-ribose, with an apparent $K_D$<5 mM. Among the other ligands identified for hIntL-1 in this study was the disaccharide 2-acetamido-2-deoxy-4-O-beta-D-galactofuranosyl-D-glucopyranose, with a reported apparent affinity of 9 mM. The carbohydrate D-galactofuranose (Galf) is the thermodynamically disfavored five-membered ring isomer of D-galactose. Examples of Galf have been described in bacteria, protozoans, fungi, and nematodes (Nassau et al., 1996; Tefsen et al., 2012; Wesener et al., 2013; Pederson & Turco, 2003). Mammals lack the enzyme uridine 5'-diphosphate (UDP) galactopyranose mutase (UGM) that is requisite for biosynthesis of the Galf glycosyl donor (Blixt et al., 2004). Hence, Galf is a nonhuman glycan epitope and could be used to specifically assign non-self status to cells. Combined with the previously mentioned expression profile, data suggest a role for hIntL in detecting microbial specific glycan epitopes in the lung and gastrointestinal tract.

II. Bacterial Infections

While humans contain numerous different bacteria on and inside their bodies, an imbalance in bacterial levels or the introduction of pathogenic bacteria can cause a symptomatic bacterial infection. Pathogenic bacteria cause a variety of different diseases including but not limited to numerous foodborne illness, typhoid fever, tuberculosis, pneumonia, syphilis, and leprosy.

Additionally, different bacteria have a wide range of interactions with body and those interactions can modulate ability of the bacteria to cause an infection. For example, bacteria can be conditionally pathogenic such that they only cause an infection under specific conditions. For example, *Staphylococcus* and *Streptococcus* bacteria exist in the normal human bacterial biome, but these bacteria when they are allowed to colonize other parts of the body causing a skin infection, pneumonia, or sepsis. Other bacteria are known as opportunistic pathogens and only cause diseases in a patient with a weakened immune system or another disease or disorder.

Bacteria can also be intracellular pathogens which can grow and reproduce within the cells of the host organism. Such bacteria can be divided into two major categories as either obligate intracellular parasites or facultative intracellular parasites. Obligate intracellular parasites require the host cell in order to reproduce and include such bacteria as but are not limited to *Chlamydophila, Rickettsia*, and *Ehrlichia* which are known to cause pneumonia, urinary tract infections, typhus, and Rocky Mountain spotted fever. Facultative intracellular parasites can reproduce either intracellular or extracellular. Some non-limiting examples of facultative intracellular parasites include *Salmonella, Listeria, Legionella, Mycobacterium*, and *Brucella* which are known to cause food poisoning, typhoid fever, sepsis, meningitis, Legionnaire's disease, tuberculosis, leprosy, and brucellosis.

Finally, bacterial infections can be related to a specific location in or on the body. For example, bacteria could be harmless if only exposed to the specific organs, but when it comes in contact with a specific organ or tissue, the bacteria can begin replicating and cause a bacterial infection.

A. Gram-Positive Bacteria

In some aspects of the present disclosure, the peptides disclosed herein may be used to treat a bacterial infection by a gram-positive bacterium. Gram-positive bacteria contain a thick peptidoglycan layer within the cell wall which prevents the bacteria from releasing the stain when dyed with crystal violet. Without being bound by theory, the gram-positive bacteria are often more susceptible to antibiotics. Generally, gram-positive bacteria, in addition to the thick peptidoglycan layer, also comprise a lipid monolayer and contain teichoic acids which react with lipids to form lipoteichoic acids that can act as a chelating agent. Additionally, in gram-positive bacteria, the peptidoglycan layer is outer surface of the bacteria. Many gram-positive bacteria have been known to cause disease including, but are not limited to, *Streptococcus, Staphylococcus, Corynebacterium, Enterococcus, Listeria, Bacillus, Clostridium, Rathybacter, Leifsonia*, and *Clavibacter.*

B. Gram-Negative Bacteria

In some aspects of the present disclosure, the peptides disclosed herein may be used to treat a bacterial infection by a gram-negative bacterium. Gram-negative bacteria do not retain the crystal violet stain after washing with alcohol. Gram-negative bacteria, on the other hand, have a thin peptidoglycan layer with an outer membrane of lipopolysaccharides and phospholipids as well as a space between the peptidoglycan and the outer cell membrane called the periplasmic space. Lipopolysaccharides typically contain heptoses, KO, and KDO in their core. Gram-negative bacterial generally do not have teichoic acids or lipoteichoic acids in their outer coating. Generally, gram-negative bacteria also release some endotoxin and contain prions which act as molecular transport units for specific compounds. Most bacteria are gram-negative. Some non-limiting examples of gram-negative bacteria include *Bordetella, Borrelia, Burcelia, Campylobacteria, Escherichia, Francisella, Haemophilus, Helicobacter, Legionella, Leptospira, Neisseria, Pseudomonas, Rickettsia, Salmonella, Shigella, Treponema, Vibrio*, and *Yersinia.*

C. Gram-Indeterminate Bacteria

In some aspects of the present disclosure, the compounds disclosed herein may be used to treat a bacterial infection by a gram-indeterminate bacterium. Gram-indeterminate bacteria do not full stain or partially stain when exposed to crystal violet. Without being bound by theory, a gram-indeterminate bacterium may exhibit some of the properties of the gram-positive and gram-negative bacteria. Non-limiting examples of gram-indeterminate bacterium include *Mycobacterium tuberculosis* or *Mycobacterium leprae.*

III. Polypeptides/Peptides/Fusions

A. Intelectins and Variants Thereof

The present disclosure contemplates the production and use of various intelectin polypeptides. The sequences (cDNA and protein) of human intelectin-1 are provided in FIG. 26. Additional exemplary recombinant constructs are shown in FIGS. 19-25.

B. Synthesis

1. Recombinant Techniques

For producing larger protein sequences, recombinant techniques are preferred. Such techniques are well known to those of skill in the art. Such techniques generally rely on the use of expression vectors that contain the machinery necessary to produce the protein of interest. Hence, the term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1989 and Ausubel et al., 1994, both incorporated herein by reference).

The term "expression vector" refers to any type of genetic construct comprising a nucleic acid coding for an RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control" and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous" or "homologous." Similarly, an enhancer may be one naturally associated with a nucleic acid sequence, located either downstream or upstream of that sequence. Alternatively, certain advantages will be gained by positioning the coding nucleic acid segment under the control of a recombinant, exogenous or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in prokaryotic recombinant DNA construction include the β-lactamase (penicillinase), lactose and tryptophan (trp) promoter systems.

Naturally, it will be important to employ a promoter and/or enhancer that effectively directs the expression of the DNA segment in the organelle, cell, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression.

The vectors or constructs will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

In certain embodiments, cells containing a nucleic acid constructs may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

In certain embodiments, a plasmid vector is contemplated for use to transform a host cell. In general, plasmid vectors containing replicon and control sequences which are derived from species compatible with the host cell are used in connection with these hosts. In addition, phage vectors containing replicon and control sequences that are compatible with the host microorganism can be used as transforming vectors in connection with these hosts. The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells).

Suitable non-viral methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection, by injection, including microinjection; by electroporation; by calcium phosphate precipitation; by using DEAE-dextran followed by polyethylene glycol; by direct sonic loading; by liposome-mediated transfection and receptor-mediated transfection; by microprojectile bombardment; and any combination of such methods. Through the application of techniques such as these, organelle(s), cell(s), tissue(s) or organism(s) may be stably or transiently transformed.

As used herein, the terms "cell," "cell line," and "cell culture" may be used interchangeably. All of these terms also include their progeny, which includes any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MaxBac® 2.0 from Invitrogen® and BacPack™ Baculovirus Expression System From Clontech®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

2. Chemical Synthesis

In certain aspects, it will be advantageous to produce peptides using solid-phase synthetic techniques. Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the disclosure are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a post-translational modification of proline.

C. Fusion Proteins

Fusion proteins are created by a head-to-tail linking of two proteinaceous molecules such that peptide sequences not normally found together in nature are joined in a single protein chain. These may be entire molecules, or domains derived from larger sequences. The joining may be mechanical, as where a "linker" molecule is just to connect the two proteins/domains, or genetically, where coding sequences for the proteins/domains are fused at the DNA level and a single transcript and protein product are synthesis.

hIntL-1 shares some sequence homology with the ficolin lectins. Ficolin proteins, along with other examples like mannan-binding lectin (NCBI mRNA RefSeq NM_000242), have an additional domain outside of their carbohydrate recognition domain that allows them to activate human complement for cell killing. This domain is usually located N-terminal of the carbohydrate recognition domain and is easy to recognize because of the presence of a collagen-like domain. hIntL-1 lacks this domain.

The inventors propose the fusion of ficolin and mannan-binding lectin complement activation domains onto the N-terminus of hIntL-1 to create a new molecule able to recognize cells and to kill them. These proteins have several advantages in that they are already human proteins and will likely be well tolerated by the human immune system. A variety of examples of such fusion proteins are provided in FIGS. 20-25. These molecules may optionally include a Strep-tagII or other similar motif for use for purification (not shown). Another type of fusion appends peptide sequences to the N-terminus of hIntL-1 that can target the protein to specific cell types (see FIG. 19). One example is polypeptide chains that target CD3, which are engineered antibody Fab sequences bind to CD3 with nanomolar affinity.

D. Linkers

Linkers or cross-linking agents may be used to fuse peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called “Stapled Peptide” technology of Aileron Therapeutics. The general approach for “stapling” a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al. (2000).

E. Modifications, Variants and Analogs

The inventors also contemplate that variants of the sequences may be employed. For example, certain natural and non-natural amino acids that satisfy the structural constraints of native sequences may be used to replace a native residue without a loss, and perhaps with an improvement in, biological function. In addition, the present inventors also contemplate that structurally similar compounds may be formulated to mimic the key portions of peptide or polypeptides of the present disclosure. Such compounds, which may be termed peptidomimetics, may be used in the same manner as the peptides of the disclosure and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

As used herein, “molecular modeling” means quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures. Compounds of the disclosure also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

Also of interest are peptidomimetic compounds that are designed based upon the amino acid sequences of compounds of the disclosure. Peptidomimetic compounds are synthetic compounds having a three-dimensional conformation “motif” that is substantially the same as the three-dimensional conformation of a selected peptide. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Polypeptides may be modified for in vivo use by the addition, at the amino- and/or carboxyl-terminal ends, of a blocking agent to facilitate survival of the polypeptide in vivo. This can be useful in those situations in which the polypeptide termini tend to be degraded by proteases. Such blocking agents can include, without limitation, additional related or unrelated sequences that can be attached to the amino and/or carboxyl terminal residues of the peptide to be administered. These agents can be introduced by recombinant DNA technology using methods familiar in the art. Alternatively, blocking agents such as pyroglutamic acid or other molecules known in the art can be attached to the amino- and/or carboxyl-terminal residues.

It may also be useful to include “tags” in polypeptides of the present disclosure. Such tags may permit purification of the polypeptides, and include biotin, Strep-tag, or 6×His tags. The tags may also permit identification of the molecule through the use of an agent that recognizes the tag. Polypeptides may also be “labeled” with a detectable label, such as a fluorescent moiety, a chemiluminescent moiety, a dye, a radiolabel, a chromophore, a bioluminescent moiety, a nanoparticle or a bead.

IV. Methods of Treating Bacterial Infections

A. Therapeutic Regimens and Pharmacologic Preparations

The present disclosure contemplates the treatment of bacterial infections in or on a surface of a subject. The treatment may be provided to a particular infection site in the patient, or may be provided systemically. Where such clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector or cells, dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the vectors or cells of the compositions.

The active compositions of the present disclosure may include classic pharmaceutical preparations. Administration of these compositions according to the present disclosure may be via any common route so long as the target tissue is available via that route. This includes oral, nasal, inhalation or buccal. Alternatively, administration may be by intradermal, subcutaneous, intramuscular, intraperitoneal or intravenous injection. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the polypeptides of the present disclosure generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety, and purity standards as required by FDA Office of Biologics standards.

B. Combined Therapy

In another embodiment, it is envisioned to use polypeptide/peptide/fusion as described herein combination with other therapeutic modalities. Thus, in addition to the therapies described above, one may also provide to the patient more "standard" pharmaceutical therapies. Examples of other therapies include, without limitation, antibiotics and other antimicrobial compounds.

Combinations may be achieved by contacting cells or subjects with a single composition or pharmacological formulation that includes both agents, or by contacting the cell with two distinct compositions or formulations, at the same time, wherein one composition includes present polypeptides/peptides/fusions and the other includes the agent. Alternatively, the therapy using the polypeptides/peptides/fusions of the present disclosure may precede or follow administration of the other agent(s) by intervals ranging from minutes to weeks. In embodiments where the other agent and the polypeptides/peptides/fusions are applied separately to the cell, one would generally ensure that a significant period of time did not expire between the time of each delivery, such that the other agent and polypeptides/peptides/fusions would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a polypeptides/peptides/fusions according to the present disclosure, or the other agent will be desired. In this regard, various combinations may be employed. By way of illustration, where the peptide/polypeptide/fusion of according to the present disclosure is "A" and the other agent is "B", the following permutations based on 3 and 4 total administrations are exemplary:

```
A/B/A B/A/B B/B/A A/A/B B/A/A A/B/B B/B/B/A

B/B/A/B A/A/B/B A/B/A/B A/B/B/A B/B/A/A B/A/B/A

B/A/A/B B/B/B/A A/A/A/B B/A/A/A A/B/A/A A/A/B/A

A/B/B/B B/A/B/B B/B/A/B
```

Other combinations are likewise contemplated.

C. Supplemental Pharmacological Therapeutic Agents

Pharmacological therapeutic agents and methods of administration, dosages, etc., are well known to those of skill in the art (see for example, the "Physicians Desk Reference," Klaassen's "The Pharmacological Basis of Therapeutics," "Remington's Pharmaceutical Sciences," and "The Merck Index, Eleventh Edition," incorporated herein by reference in relevant parts), and may be combined with the disclosure in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

The term "antibiotics" are drugs which may be used to treat a bacterial infection through either inhibiting the growth of bacteria or killing bacteria. Without being bound by theory, it is believed that antibiotics can be classified into two major classes: bactericidal agents that kill bacteria or bacteriostatic agents that slow down or prevent the growth of bacteria.

The first commercially available antibiotic was released in the 1930's. Since then, many different antibiotics have been developed and widely prescribed. In 2010, on average, 4 in 5 Americans are prescribed antibiotics annually. Given the prevalence of antibiotics, bacteria have started to develop resistance to specific antibiotics and antibiotic mechanisms. Without being bound by theory, the use of antibiotics in combination with another antibiotic may modulate resistance and enhance the efficacy of one or both agents.

In some embodiments, antibiotics can fall into a wide range of classes. In some embodiments, the compounds of the present disclosure may be used in conjunction with another antibiotic. In some embodiments, the compounds may be used in conjunction with a narrow spectrum antibiotic which targets a specific bacteria type. In some non-limiting examples of bactericidal antibiotics include penicillin, cephalosporin, polymyxin, rifamycin, lipiarmycin, quinolones, and sulfonamides. In some non-limiting examples of bacteriostatic antibiotics include macrolides, lincosamides, or tetracyclines. In some embodiments, the antibiotic is an aminoglycoside such as kanamycin and streptomycin, an ansamycin such as rifaximin and geldanamycin, a carbacephem such as loracarbef, a carbapenem such as ertapenem, imipenem, a cephalosporin such as cephalexin, cefixime, cefepime, and ceftobiprole, a glycopeptide such as vancomycin or teicoplanin, a lincosamide such as lincomycin and clindamycin, a lipopeptide such as daptomycin, a macrolide such as clarithromycin, spiramycin, azithromycin, and telithromycin, a monobactam such as aztreonam, a nitrofuran such as furazolidone and nitrofurantoin, an oxazolidonones such as linezolid, a penicillin such as amoxicillin, azlocillin, flucloxacillin, and penicillin G, an antibiotic polypeptide such as bacitracin, polymyxin B, and colistin, a quinolone such as ciprofloxacin, levofloxacin, and gatifloxacin, a sulfonamide such as silver sulfadiazine, mefenide, sulfadimethoxine, or sulfasalazine, or a tetracycline such as demeclocycline, doxycycline, minocycline, oxytetracycline, or tetracycline. In some embodiments, the compounds could be combined with a drug which acts against mycobacteria such as cycloserine, capreomycin, ethionamide, rifampicin, rifabutin, rifapentine, and streptomycin. Other antibiotics that are contemplated for combination therapies may include arsphenamine, chloramphenicol, fosfomycin, fusidic acid, metronidazole, mupirocin, platensimycin, quinupristin, dalfopristin, thiamphenicol, tigecycline, tinidazole, or trimethoprim. Any of the foregoing agents may be provided in combination with the peptides/polypeptides of the present disclosure, for example, by provision as distinct agents, or linked together as a single "conjugate" molecule.

Another agent that can be used in conjunction with the polypeptides/peptides of the present disclosure is a UGM inhibitor. The galactofuran region of the mycobacterial cell wall consists of alternating 5- and 6-linked β-D-galactofuranose (β-D-Galf) residues, essential for viability. UDP-galactofuranose (UDP-Galf), the donor for Galf, is synthesised from UDP-galactopyranose (UDP-Galp) by the enzyme UDP-galactopyranose mutase (UGM), which is not found in humans, rendering it a therapeutic target. 4-chlorophenyl)-[1-(4-chlorophenyl)-3-hydroxy-5-methyl-1H-pyrazol-4-yl]- methanone and 3-(4-iodophenyl)-2-[4-(3,4-dichlorophenyl)-thiazol-2-ylamino]-propionic acid are two such compounds. The first is a pyrazole and inhibits UGM from *Mycobacterium tuberculosis, Klebsiella pneumoniae, Mycobacterium smegmatis, Mycobacterium bovis* BCG and *M. tuberculosis*. The latter is an aminothiazole that is active against UGM from *K. pneumoniae* and *M. tuberculosis*. Other UGM inhibitors include a recently described triazolothiadiazine based scaffod that has been shown to inhibit *Mycobacterium tuberculosis* growth (Kincaid et al. *ACS Chem. Biol.* 2015 (10). 2209-2218.

V. Purification of Peptides/Proteins

It will be desirable to purify peptides and polypeptides according to the present disclosure. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present disclosure concern the purification, and in particular embodiments the substantial purification, of a protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High performance liquid chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of non-antibody proteins that recognize carbohydrate epitopes of polysaccharides and glycoproteins. Lectins can be coupled to agarose by cyanogen bromide to generate affinity resins. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present disclosure is discussed below.

A particular embodiment that can be employed with intelectins is purification using affinity to carbohydrates. Specifically for hIntL-1, linear carbohydrates (specifically sorbitol), or other carbohydrates that contain an exocyclic diol (like β-galactofuranose), can be immobilized on a resin. The terminal exocyclic diol on most linear carbohydrates is an excellent ligand for intelectins, so when they are immobilized on a resin, they capture intelectins in a calcium ion dependent manner. They can be eluted by EDTA or the addition of excess exocyclic diol containing compounds (such as glycerol or sorbitol). This has been demonstrated with a galactofuranose column, but other carbohydrate ligands function as well. In a particular aspect, the inventors use sorbitol that is immobilized on a sepharose resin through divinyl sulfone chemistry. Divinyl sulfone chemistry for carbohydrate resins is well established.

VI. Definitions

The term "treatment" or grammatical equivalents encompasses the improvement and/or reversal of the symptoms of heart failure (i.e., the ability of the heart to pump blood). "Improvement in the physiologic function" of the heart may be assessed using any of the measurements described herein (e.g., measurement of ejection fraction, fractional shortening, left ventricular internal dimension, heart rate, etc.), as well as any effect upon the animal's survival. In use of animal models, the response of treated transgenic animals and untreated transgenic animals is compared using any of the assays described herein (in addition, treated and untreated non-transgenic animals may be included as controls). A compound which causes an improvement in any parameter associated with heart failure used in the screening methods of the instant disclosure may thereby be identified as a therapeutic compound.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present disclosure. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

As used herein, the terms "antagonist" and "inhibitor" refer to molecules, compounds, or nucleic acids which inhibit the action of a target molecule. Antagonists may or may not be homologous to these natural compounds in respect to conformation, charge or other characteristics. Thus, antagonists may be recognized by the same or different receptors that are recognized by an agonist. Antagonists may have allosteric effects which prevent the action of an agonist. Alternatively, antagonists may prevent the function of the agonist. In contrast to the agonists, antagonistic compounds do not result in pathologic and/or biochemical changes within the cell such that the cell reacts to the presence of the antagonist in the same manner as if the cellular factor was present. Antagonists and inhibitors may include proteins, nucleic acids, carbohydrates, or any other molecules which bind or interact with a receptor, molecule, and/or pathway of interest.

As used herein, the term "modulate" refers to a change or an alteration in a biological activity. Modulation may be an increase or a decrease in protein activity, a change in kinase activity, a change in binding characteristics, or any other change in the biological, functional, or immunological properties associated with the activity of a protein or other structure of interest. The term "modulator" refers to any molecule or compound which is capable of changing or altering biological activity as described above.

VII. Examples

The following examples are included to further illustrate various aspects of the disclosure. It should be appreciated by those of skill in the art that the techniques disclosed in the examples which follow represent techniques and/or compositions discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Materials and Methods

Clustal W Alignment. Intelectin and ficolin proteins were selected for Clustal W analysis using MegAlign in the Lasergene 8 Suite (DNASTAR). Intelectins include human intelectin-1 (hIntL-1), accession no. Q8WWA0; human intelectin-2 (hIntL-2), Q8WWU7; mouse intelectin-1 (mIntL-1), 088310; mouse intelectin-2 (mIntL-2), Q80ZA0; sheep intelectin-1 (sIntL-1), Q3LAF5; *Xenopus laevis* intelectin-1 (XIntL-1), Q5PPM0; human H-ficolin (h H-ficolin), O75636; human L-ficolin (h L-ficolin), Q15485; human M-ficolin (h M-ficolin), O00602. Proteins were aligned using the default Clustal W Method parameters on the slow and accurate mode.

Native Human Intelectin-1 Expression and Purification. The cDNA for hIntL-1 (Accession Number: $NM_{13}$ 017625) was obtained from Open Biosystems Clone LIFESEQ2924416 as a glycerol stock (GE Healthcare). The full coding sequence, residues 1-313, were amplified using PRC with the forward primer 5'-CGTGGGATCCTGGAGGGAGGGAGTGAAGGAGC-3' (SEQ ID NO: 35) and the reverse primer 5'-GCCAGCTCGAGACCTTGGGATCTCATGGTTGGGAGG-3' (SEQ ID NO: 36). The primers installed restriction endonuclease sites for BamH1 and XhoI, respectively. The doubly digested hIntL-1 PCR fragment was ligated into a doubly digested pcDNA4/myc-HisA vector backbone (Life Technologies). Correct insertion was confirmed with DNA sequencing (UW-Madison Biotechnology Center).

hIntL-1 was expressed via transient transfection of suspension adapted HEK 293T cells. Cells were transfected in Opti-mem I Reduced Serum Medium (Life Technologies) at ~$2\times10^6$ cells/mL using Lipofectamine 2000 (Life Technologies), according to the manufacturers protocol. Six hours post transfection, the culture medium was changed to FreeStyle F17 expression medium (Life Technologies) supplemented with 50 U/mL penicillin-streptomycin, 4 mM L-glutamine, 1× nonessential amino acids, 0.1% fetal bovine serum and 0.1% Pluronic F-68 (Life Technologies). Cells were left to express hIntL-1 for up to 6 days, or until viability decreased below 60%, at which point the conditioned expression medium was harvest by centrifugation and sterile filtration.

Conditioned media was adjusted to pH=7.4 by slow addition of 0.1 M NaOH and $CaCl_2$ was added to 10 mM. hIntL-1 was purified by binding to a β-Galf column generated from reaction of Compound 51, an amine functionalized β-Galf, and UltraLink Biosupport (Piere). Resin was washed with 20 mM HEPES (7.4) 150 mM NaCl and 10 mM $CaCl_2$. hIntL-1 was eluted with addition of 20 mM HEPES (7.4) 150 mM NaCl and 10 mM EDTA and concentrated using a 10,000 MWCO Amicon Ultra Centrifugal Filter. Buffer was exchanged to 20 mM HEPES (7.4) 150 mM NaCl and 1 mM EDTA. Protein purity was assessed by SDS-PAGE electrophoresis and coomassie blue staining, and was often >95%. The concentration of hIntL-1 was determined using absorbance at 280 nm with a calculated $\varepsilon=237{,}4000\ cm^{-1}M^{-1}$ for the trimer, and an estimated trimer molecular mass of 101,400 Da (to account for glycosylation). Typical yields from a 30 mL transfection were 400 μg.

hIntL-1 Carbohydrate Binding ELISA-like Assay. To fabricate carbohydrate-displaying surfaces, 0.5 μg of streptavidin (Prozyme, cat. no. SA20) was adsorbed onto a Maxisorp (Nunc) flat bottom 96 well plate in PBS. Wells were washed with PBS and then coated with 5 μM of carbohydrate-biotin ligand in PBS for 1 hour at 22° C. Wells were blocked with bovine serum albumin (BSA) in ELISA buffer (20 mM HEPES (7.4) 150 mM NaCl, 10 mM $CaCl_2$, and 0.1% tween-20). Samples containing hIntL-1 were prepared by serial dilution into ELISA buffer+0.1% BSA and added to wells for 2 hours at 22° C. Wells were washed four times with ELISA buffer. Bound hIntL-1 was detected using 0.75 μg/mL of a sheep IgG hIntL-1 antibody (R&D Systems, cat. no. AF4254) in ELISA buffer+0.1% BSA for 2 hours at 22° C. Wells were washed with ELISA buffer. A donkey anti-sheep IgG horseradish peroxidase (HRP) conjugate (Jackson ImmunoResearch Laboratories) was added at a 1:5,000 dilution in ELISA buffer+0.1% BSA for 1 hour at 22° C. Wells were washed and hIntL-1 was detected colorimetrically with addition of 1-Step Ultra TMB-ELISA (Pierce). Once sufficient signal was achieved (typically <2 min.), the reaction was quenched with addition of equal volume 2 M $H_2SO_4$. Plates were read at 450 nm on an EL×800 plate reader (Bio-Tek). When testing the $Ca^{2+}$ dependency of hIntL-1, 1 mM EDTA replaced 10 mM $CaCl_2$ in all steps. Data were analyzed on Prism6 (GraphPad). Data were fit to the one site-specific binding equation.

hIntL-1 Surface Plasmon Resonance (SPR). All hIntL-1 SPR was performed on a ProteOn XPR36 (Bio-Rad) at the University of Wisconsin-Madison Department of Biochemistry Biophysics Instrumentation Facility (BIF). To measure hIntL-1 binding, ProteOn NLC sensor chips (Bio-Rad) (NeutrAvidin coated chips) were used to capture carbohydrate-biotin ligand. All experiments presented here were conducted at surface saturated levels of ligand, ~200 RU. In all experiments, captured biotin served as a control. Samples containing purified hIntL-1 were prepared by serial dilution into hIntL-1 SPR running buffer (20 mM HEPES (7.4) 150 mM NaCl, 1 mM $CaCl_2$, and 0.005% tween-20). Surfaces were regenerated with short injections of 10 mM HCl. All data was interspot corrected and processed using the Bio-Rad ProteOn software package.

Expression and Purification of *Xenopus laevis* Strep-tagII Intelectin-1. The cDNA for *Xenopus laevis* intelectin-1 (XIntL-1) (accession number NM—001089101). An N-terminal Strep-tag® II was cloned into the hItnL-1::pcDNA4 vector using site-directed mutagenesis and a primer set comprised of 5' -ACCACCAGAGGATGGAGTACAGATTGGAGCCATCCGCAGTTTGAAAA GTCTACAGATGAGGCTAATACTTACTTCAAGGA-3' (SEQ ID NO:37) and its reverse complement. The correct insertion was confirmed with DNA sequencing. Strep-hIntL-1 was expressed identically to hIntL-1. For purification, conditioned Strep-hIntL-1 medium was adjusted to pH=7.4 using NaOH, avidin was added per the IBA GmbH protocol (IBA GmbH, cat. no. 2-0205-050), $CaCl_2$ was added to 10 mM, and the solution was cleared with centrifugation (15,000 g for 15 minutes). Protein was captured onto 2 mL of Strep-Tactin Superflow resin (IBA GmbH, cat. no. 2-1206-002). The resulting resin was washed with a solution of 20 mM HEPES (7.4), 150 mM NaCl, and 10 mM $CaCl_2$ and then 20 mM HEPES (7.4), 150 mM NaC1, and 1 mM EDTA. The protein was eluted with 5 mM d-desthiobiotin (Sigma) in 20 mM HEPES (7.4), 150 mM NaCl, and 1 mM EDTA and concentrated using a 10,000 MWCO Amicon Ultra Centrifugal Filter. The concentration of Strep-hIntL-1 was determined using absorbance at 280 nm with a calculated ε=237,400 cm-1M-1 for the trimer, and an estimated trimer molecular mass of 101,400 Da. Typical yields were similar to what was measured with untagged hIntL-1.

For protein x-ray crystallography, Strep-hIntL-1 was purified following culture medium dialysis against 20 mM BIS-TRIS (6.7), 150 mM NaCl, and 1 mM EDTA. The pH of the culture medium was adjusted to 6.7, avidin was added per the IBA GmbH protocol, $CaCl_2$ was added to 10 mM and the solution was cleared with centrifugation. Protein was purified by capture onto Strep-Tactin Superflow resin. Resin was washed with 20 mM BIS-TRIS (6.7), 150 mM NaCl, 10 mM $CaCl_2$ and then 20 mM BIS-TRIS (6.7), 150 mM NaCl, 0.5 mM EDTA. Protein was eluted with 5 mM d-desthiobiotin (Sigma) in 20 mM BIS-TRIS (6.7), 150 mM NaCl, 0.5 mM EDTA and concentrated using a 10,000 MWCO Amicon Ultra Centrifugal Filter.

Construction of the Furanoside Glycan Array. The microarray of furanoside containing glycans was printed as previously described. Briefly, the amine functionalized glycans shown in FIG. 10A were dissolved in 100 mM sodium phosphate (8.0) and printed as 14 arrays on N-hydroxysuccinimidyl (NHS) ester-activated slides (Shott Nexterion, Louisville, Ky.). Arrays were printed in replicates of n=4 at different glycan concentrations (as indicated in FIG. 10B) using a Piezorray printer (Perkin Elmer, Waltham, Mass.)

that delivered 0.33 nL per spot. The 2-amino(N-aminoethyl) benzamine (AEAB) derivatives of lacto-N-neotetraose (LNnT) and asialo, galactosylated bi-antennary N-linked glycan (NA2) were printed as controls to confirm glycan immobilization. After printing, covalent coupling of glycans to the surface was facilitated by incubation at 55° C. in an atmosphere of >80% humidity for 1 hour. Slides were dried in a desiccator overnight and blocked using a solution of 50 mM ethanolamine in 50 mM borate buffer (8.0). Prior to interrogating with glycan binding proteins (GBPs), the arrays are rehydrated in binding buffer.

Assay of hIntL-1 on Furanoside and CFG Mammalian Glycan Array. GBPs at various concentrations were applied to separate furanoside arrays in 70 μL of binding buffer (20 mM HEPES (7.4), 150 mM NaCl, 1 mM EDTA, 10 mM $CaCl_2$, 1% BSA and 0.05% Tween-20) in the wells formed on the slide with a silicon grid (14 wells per slide). After incubation for 1 hr at RT, the slides were washed with wash buffer (20 mM HEPES (7.4), 150 mM NaCl, 1 mM EDTA and 10 mM CaCl2, 0.05% Tween-20). The biotinylated lectins *Erythrina cristagalli* lectin (ECL) and *Ricinus communis* agglutinin I lectin (RCA-I) were detected using Alexa Fluor® 488-labeled streptavidin (10 μg/ml) in binding buffer (FIGS. 10C and D). hIntL-1 was detected with a sheep polyclonal IgG antibody specific for hIntL-1 (5 μg/ml) (R&D Systems) and an Alexa Fluor® 488-labeled donkey anti-sheep IgG secondary antibody (5 μg/ml) (Life Technologies). Bound protein was detected using a ProScanArray Scanner (Perkin Elmer) equipped with 4 lasers covering an excitation range from 488 to 633 nm. The data from the furanoside glycan array were analyzed with the ScanArray Express software (Perkin Elmer) as the average of the 4 replicates.

For the analysis of the CFG glycan array, hIntL-1 was applied in 70 μl at a concentration of 50 and 200 μg/ml in binding buffer under a coverslip to distribute the solution evenly over the large array of 610 glycans printed in replicates of n=6 (Array v5.1). After washing and scanning, the data from the CFG glycan microarray were analyzed using ImaGene software (BioDiscovery, Hawthorne, Calif.) as the average of 4 values after removing the high and low values of the 6 replicates. With both the furanoside and mammalian glycan array, the images were converted to Excel files, and the data are reported as histograms of average Relative Fluorescence Units (RFU) versus print identification number that identified the glycan targets. Figures were made using Prism6 (GraphPad) or Excel (Microsoft).

Assay of hIntL-1 on the Bacterial Glycan Array. Strep-hIntL-1 was used to interrogate the Microbial Glycan Microarray version 2 (MGMv2). Construction of the MGMv2 is previously described (22). Briefly, bacterial polysaccharide samples were dissolved and diluted to 0.5 mg/mL in printing buffer (150 mM sodium phosphate buffer (8.4)+0.005% Tween-20). Samples were immobilized on NHS-activated glass slides (SlideH, Schott/Nexterion) using a MicroGrid II (Digilab) contact microarray printer equipped with SMP-4B printing pins (Telechem). Six replicates of each bacterial glycan sample were printed. Covalent coupling of glycans to the surface was facilitated by incubation for 1 hour postprint at 100% relative humidity. The remaining reactive NHS-moieties were quenched using a blocking solution (50 mM ethanolamine in 50 mM borate buffer (9.2)). Blocked slides were stored at −20° C. until assays were performed. To interrogate the MGMv2, Strep-hIntL-1 was diluted to 50 μg/mL in binding buffer (20 mM Tris-HCl (7.4), 150 mM NaCl, 2 mM $CaCl_2$, 2 mM magnesium chloride ($MgCl_2$) 1% BSA, and 0.05% Tween-20) and applied directly to the array surface for 1 hour. Following incubation, the array was washed by dipping into binding buffer four times. The Strep-Tag® II on bound hIntL-1 was detected using StrepMAB-Classic Chromeo647 (10 μg/mL, IBA GmbH Lifesciences) diluted in binding buffer applied directly to the array surface and allowed to incubate for 1 hour. The array was washed in binding buffer (4 dips), binding buffer minus BSA and Tween-20 (4 dips) and de-ionized water (4 dips). Finally, the array was dried by centrifugation and scanned. Interrogated arrays were scanned for Chromeo647 signal using a ProScanArray Express scanner (Perkin Elmer) and resultant images were processed to extract signal data using Imagene (v6.0, Biodiscovery). Signal data was calculated as the average of 4 values after removing the high and low values of the 6 replicates. Data were plotted using Excel (Microsoft) as average Relative Fluorescence Units (RFU) versus print identification number. Figures were made using Prism6 (GraphPad).

Protein X-Ray Crystallography. The Strep-hIntL-1 protein that was purified using 20 mM BIS-TRIS (6.7) buffers was concentrated to 1.5 mg/mL and crystallization (hanging-drop vapor-diffusion) was achieved by mixing 1 μL of the protein solution and 1 μL of well solution (100 mM BIS-TRIS (6.0) and 25% PEG 3350). Crystals grew to full size in two weeks. Protein crystals of Apo-hIntL-1 were cryoprotected via transfer to well solution supplemented with 35% PEG 3350 for one minute and then vitrified in liquid nitrogen. The allyl-β-Galf-hIntL-1 complex was formed by soaking apohIntL-1 crystals in cryoprotection solution supplemented with 50 mM allyl-β-D-galactofuranose for two weeks.

Single crystal X-ray diffraction experiments were performed at beamline 21-ID-D (Life Sciences Collaborative Access Team, LS-CAT), Advanced Photon Source, Argonne National Laboratory. Integration, scaling, and merging were performed with HKL2000. The structure was solved using the PHENIX suite. The *Xenopus laevis* intelectin structure recently solved in the inventors' lab was used as a search model to determine the structure of apo-hIntL-1 by molecular replacement using Phase r. Because the apo-hIntL-1 and β-Galf-bound hIntL-1 data are isomorphous, the structure of β-Galf-bound hIntL-1 was solved by a difference Fourier method using apo-hIntL-1 as a starting model for rigid-body refinement with phenix.refine. The chemical restraint for 0-Galf was generated by PRODRG. Model adjustment and refinement were performed in Coot and phenix.refine, respectively. The model was validated using MolProbity. Crystal structure figures were generated with PyMOL.

XIntL-1 was expressed as a secreted protein in High Five cells (Life Technologies), a derivative of *Trichopulsia ni*, by the addition of 0.5 μL of baculovirus conditioned medium per $1\times10^6$ viable cells. For selenomethione labeled XIntL-1 used for phasing, High Five cells were suspension cultured in 921 Delta Series, Methionine Deficient medium (Expression Systems, cat. no. 96-200) supplemented with 1× anti-biotic-antimycotic (Life Technologies) and 10 μg/mL gentamicin (Life Technologies). Expression was induced when cells reached a density $\geq2\times10^6$ cells/mL by the addition of 0.5 μL of baculovirus conditioned media per $1\times10^6$ viable cells. L-selenomethionine (Acros Organics) was dissolved in water at 10 mg/mL and sterile filtered. The first addition of selenomethionine was 10 mgs at 12 hours post infection, 10 additional mgs were added every 24 hours up until medium harvest. No significant toxicity or growth defect was observed. Cells were allowed to express XIntL-1 for 5 days at 22° C. in a baffled flask shaking at 90 RPM. Conditioned culture medium was harvest by centrifugation and filtration through a 0.22 μM filter unit, the media was stored at 4° C. for at least one week. Conditioned media was dialyzed extensively against 20 mM bis-tris (6.7), 150 mM NaCl, and 1 mM EDTA. The media was slowly adjusted to pH=6.7, $CaCl_2$ was added 10 mM, 4 μL of 7 mg/mL avidin (Calbiochem) per mL of conditioned media was added to absorb excess biotin, and the solution was cleared by centrifugation. Strep-tagII XIntL-1 was purified by binding to Strep-Tactin Superflow resin (IBA GmbH, cat. no. 2-1206-002). The column was washed with 20 mM bis-tris (6.7), 150 mM NaCl, 10 mM $CaCl_2$ and then 20 mM bis-tris (6.7), 150 mM NaCl, 0.5 mM EDTA. Protein was eluted with 5 mM d-desthiobiotin (Sigma) in 20 mM bis-tris (6.7), 150 mM NaCl, 0.5 mM EDTA and concentrated using a 10,000 MWCO Amicon Ultra Centrifugal Filter. During the concentration process, large sheet-like crystals began to form. Crystals were harvested by centrifugation at 2,000 RPM and washed 2 times using 20 mM bis-tris (6.7), 150 mM NaCl, 0.5 mM EDTA. The crystals were resuspended in 20 mM bis-tris (6.7), 150 mM NaCl, 0.5 mM EDTA and $CaCl_2$ was added to 5 mM. Within one minute, the crystals completely redissolved. Protein purity of the redissolved crystals was assessed by SDS-PAGE electrophoresis and coomassie blue staining and was >95%. The concentration of XIntL-1 was determined using absorbance at 280 nm with an estimated $\varepsilon$=75,455 $cm^{-1}M^{-1}$ for the monomer and a calculated molecular mass of 36,258 Da, post signal peptide removal. Typical yields were 0.5 mg per 50 mL of conditioned media. Selenomethionine incorporation was assessed using electrospray ionization mass spectrometry (UW-Madison Biotechnology Center).

Expression and Purification of Strep-tagll hIntL-1 for Crystallography. An N-terminal Strep-tag II was cloned into the hItnL-1::pcDNA4 vector using site-directed mutagenesis and the primer set 5'-accaccagaggatggagtacagattggagccatccgcagtttgaaaagtctacagatgaggctaatacttacttcaagga-3' (SEQ ID NO: 38) and its reverse complement. The correct insertion was confirmed with DNA sequencing. Strep-hlntL-1 was expressed identically to hIntL-1 expression. Strep-hlntL-1 was purified following culture medium dialysis against 20 mM bis-tris (6.7), 150 mM NaCl, and 1 mM EDTA. The pH of the culture media was adjusted to 6.7, avidin was added per the IBA GmbH protocol, $CaCl_2$ was added to 10 mM and the solution was cleared with centrifugation. Protein was purified by capture onto Strep-Tactin Superflow resin. Resin was washed with 20 mM bis-tris (6.7), 150 mM NaCl, 10 mM $CaCl_2$ and then 20 mM bis-tris (6.7), 150 mM NaCl, 0.5 mM EDTA. Protein was eluted with 5 mM d-desthiobiotin (Sigma) in 20 mM bis-tris (6.7), 150 mM NaCl, 0.5 mM EDTA and concentrated using a 10,000 MWCO Amicon Ultra Centrifugal Filter. Typical yields were similar to what was measured with untagged hlntL-1.

Commercially Available and Previously Characterized Compounds Used in This Study. The α-N-acetyl-neuraminic acid-biotin ligand used in this study was purchased from GlycoTech (Gaithersburg, Md.; cat. no. 02-012). Glycerol phosphate was purchased from Sigma Aldrich (Milwaukee, Wis.: cat. no. G7886). The 2-O-methyl-N-acetyl-α-neuraminic acid was purchased from Toronoto Research Chemicals (North York, ON, Canada; cat. no. M275400). The synthesis of the α-rhamnose-biotin ligand has been described previously.

Materials and General Information. All commercially available reagents were purchased from Sigma-Aldrich (St. Louis, Mo.) unless otherwise specified. Methanol (MeOH) was distilled over magnesium filings. Dichloromethane (CH2Cl2) and triethylamine (TEA) were distilled over calcium hydride. N,Ndimethyl formamide (DMF), dichloroethane (DCE), tetrahydrofuran (THF), tert-butanol (tBuOH), ethanol (EtOH), acetonitrile (MeCN), hexanes, and ethyl acetate (EtOAc) were used as received. All reactions were run under an inert atmosphere of N2 unless otherwise specified. Reactions were stirred using Teflon coated magnetic stir bars. All glassware and stir bars were oven-dried prior to use. Cold baths were prepared using water/ice (0° C.), brine/ice (−5° C.), or ethylene glycol/$CO_2$ (−10° C.).

Analytical thin layer chromatography (TLC) was carried out on E. Merck (Darmstadt) TLC plates pre-coated with silica gel 60 F254 (250 μm layer thickness). Analyte visualization was accomplished using a UV lamp and by charring with p-anisaldehyde (3.5 mL in 350 mL ethanol, acidified with 15 mL glacial acetic acid and 50 mL concentrated $H_2SO_4$). Flash column chromatography was performed on SiliaFlash® P60 (Silicycle; Quebec City, Canada; 40-63 μm particle size).

Proton nuclear magnetic resonance (1H-NMR) spectra were obtained using a Varian Mercury-300 MHz spectrometer, Bruker Avance III 400 MHz spectrometer, or Bruker Avance III 500 MHz spectrometer. Chemical shifts are reported relative to tetramethylsilane or residual solvent peaks in parts per million ($CHCl_3$: 1H: δ 7.26; MeOH-d4: 1H: δ 3.33). Peak multiplicity is reported as singlet (s), doublet (d), doublet of doublets (dd), doublet of doublet of triplets (ddt), triplet (t), triplet of doublets (td), pentet (pent), ABX quartet (ABX), multiplet (m). High resolution electrospray ionization mass spectra (HRESI-MS) were obtained on a Micromass LCT mass spectrometer.

Example 2

Results

Figure 7:
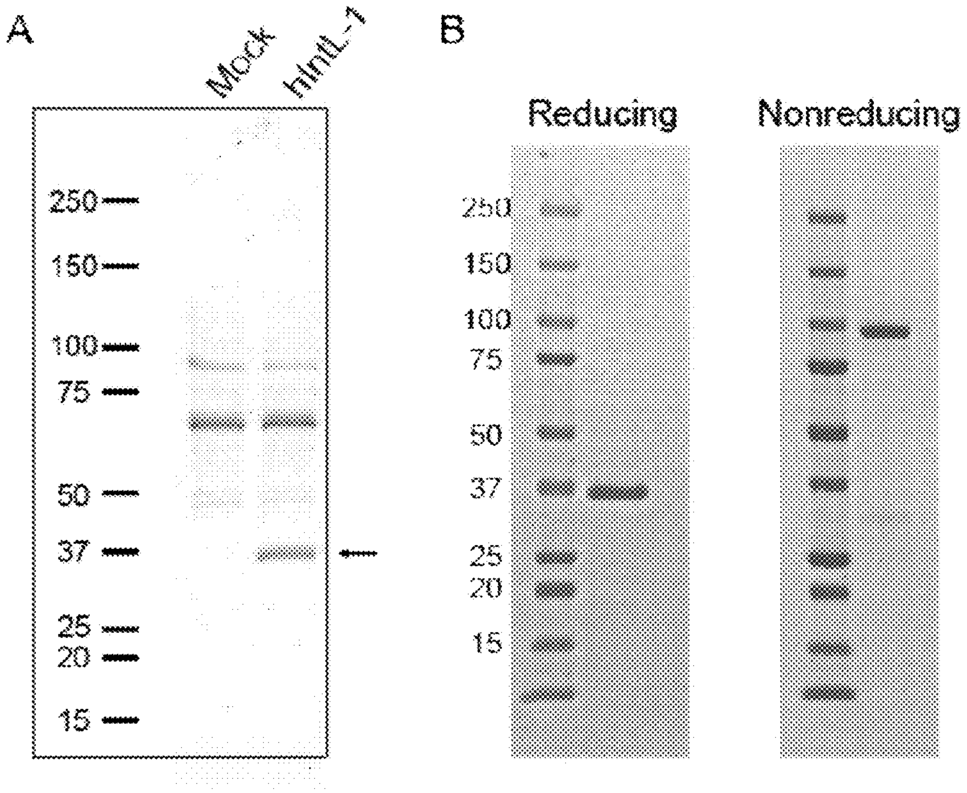
FIGS. 7A-B. Expression and Purification of hIntL-1.

The investigators were interested in the specific recognition of nonhuman glycans by hIntL-1. A lectin specific for Galf would be an invaluable tool for detecting galactofuranosylated biomolecules in complex mixtures. Previous researchers have explored the carbohydrate-binding specificity of intelectin proteins, although a general trend of ligand preferences could not be determined (Tsuji et al., 2001). The difficulty of accurately determining the carbohydrate preferences of hIntL-1 likely resulted from their use of soluble monosaccharides with a free reducing end as competitors. The presence of a free reducing end, as opposed to glycosides, results in a mixture of linear and various ring closed isomers. As a result, the precise molecules that compete for intelectin binding with an immobilized polysaccharide were unclear from previous experiments. The investigators first established a robust expression and purification strategy for hIntL-1. Based on the intra- and intermolecular disulfide bonds and reported N-glycosylation, they chose a HEK293-T based mammalian transient expression system. Transfection of suspension cells yields high amounts of properly folded disulfide-linked trimeric hIntL-1. For initial characterization, hIntL-1 was purified by exploiting its carbohydrate binding activity to an immobilized β-Galf agarose column (FIGS. 7A-B). Previous to this successful purification strategy, the investigators attempted unsuccessfully to purify hIntL-1 using an immobilized galactopyranose and an immobilized β-ribofuranose column. This was their first indication that hIntL-1 bound Galf.

Figure 1:
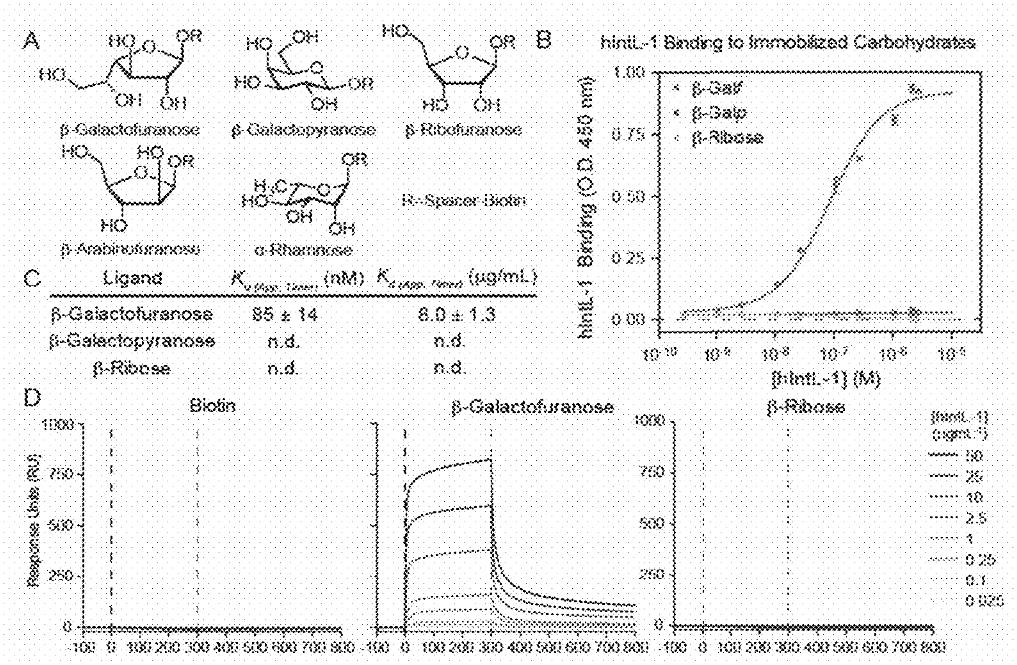
FIGS. 1A-D. hIntL-1 selectively binds β-Galf with high affinity.
Figure 8:
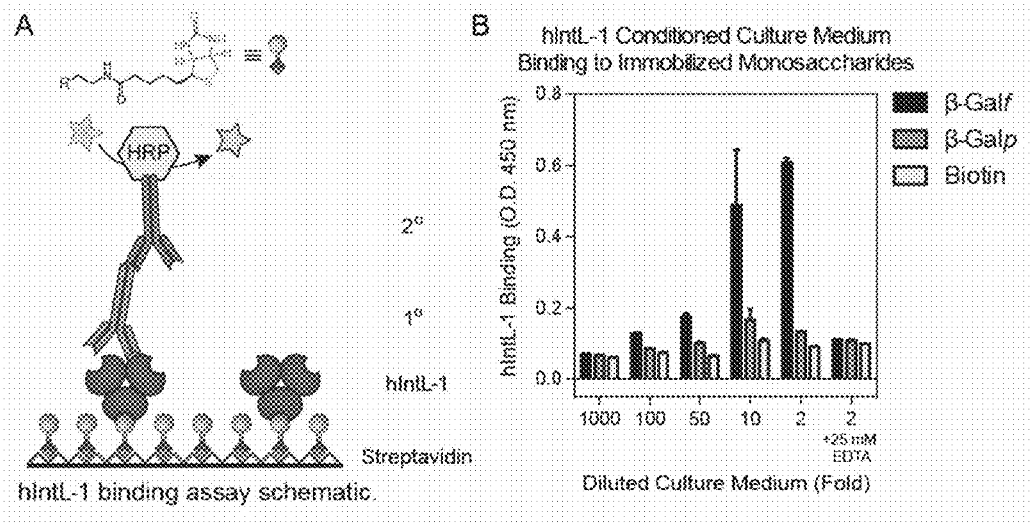
FIGS. 8A-B. hIntL-1 Conditioned Culture Media Specifically Binds β-Galf.
Figure 9:
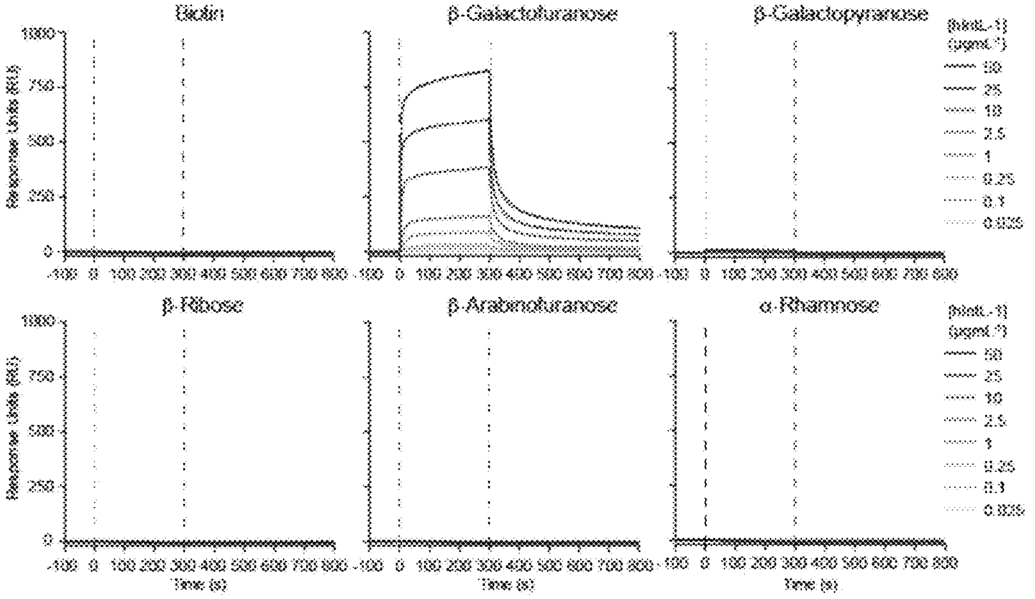
FIG. 9. SPR analysis of hIntL-1. Complete data set of hIntL-1 SPR analysis presented in FIG. 1*d*. No binding to an immobilized carbohydrate is observed other than robust binding to β-Galf. β-Ribofuranose and β-arabinofuranose were included as they were previously reported to be ligands of hIntL-1. β-Rhamnose was included as it is a non-human monosaccharide. Data was injection and baseline aligned using the Bio-Rad ProteOn software. Data is interspot corrected.

To assess the carbohydrate binding activity of recombinant hIntL-1, the investigators employed biotinylated carbohydrates and an enzyme-linked immunoabsorbent (ELISA) like assay (FIGS. 1A and 8A-B). Using this assay, the investigators show that trimeric hIntL-1 binds immobilized β-Galf with an avidity of 85±14 nM (FIGS. 1B-C). Unlike previous reports, these results reveal that hIntL-1 is exceptionally specific for Galf as binding to other immobilized carbohydrate ligands was not detected. To further probe the ligand specificity of hIntL-1, the investigators chose to investigate binding using surface plasmon resonance (SPR). The results of this ELISA suggested specific binding to β-Galf, but ELISAs are dependent on the dissociation kinetics ($k_d$) of hIntL-1::carbohydrate complexes. The investigators envisioned using SPR as a more biologically relevant assay of lectin binding. In this format, carbohydrate ligands are immobilized in a multivalent display on a cell surface, both lectin and ligand are at steady state concentrations, and ligand binding will be independent of $k_d$. For examining specificity, they added two additional nonhuman glycans; β-arabinofuranose (Araf) and β-rhamnose. Even at concentrations 6-fold higher than the β-Galf $K_D$, high specificity of hIntL-1 binding was observed (FIGS. 1D and 9). The small response to immobilized β-galactopyranose (β-Galp) is attributed to the extended anomeric alkyl linker it bears. This SPR result supports the specificity the investigators observed with their ELISA.

Figure 2:
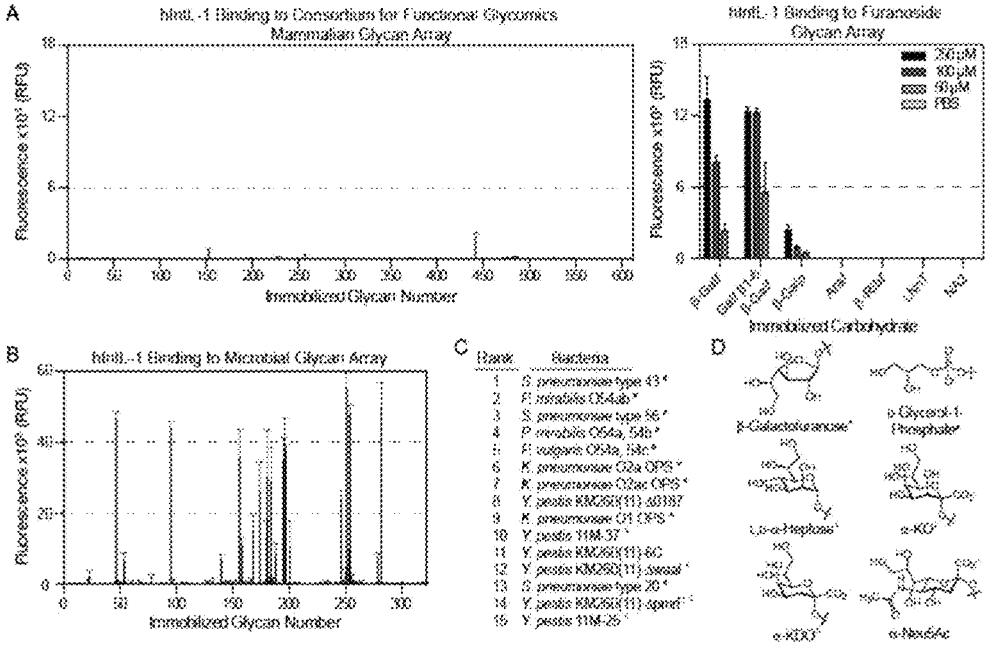
FIGS. 2A-D. hIntL-1 binds microbial glycan epitopes.
Figure 3:
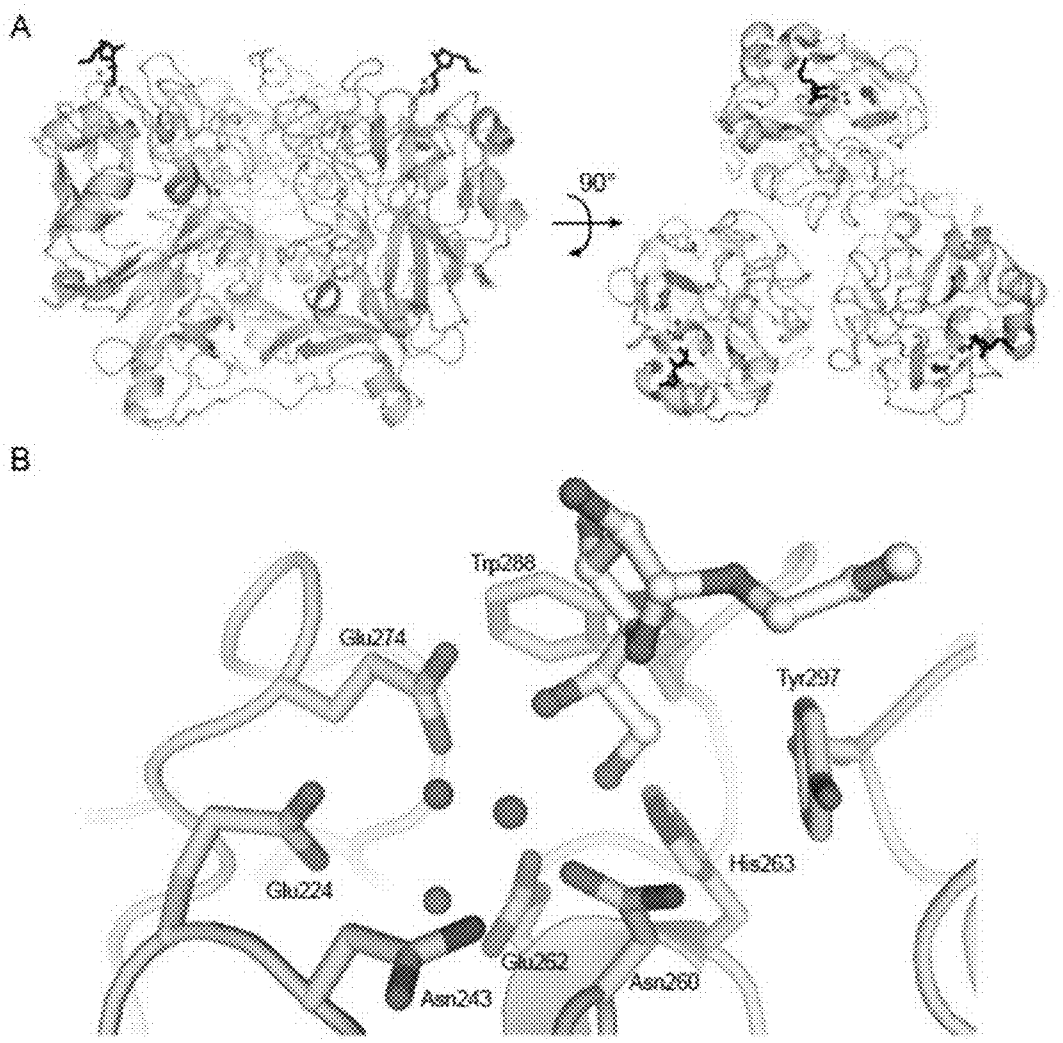
FIGS. 3A-B. Structure of hIntL-1 bound to allyl-β-D-Galf.

Glycan microarray technology has revolutionized the field of glycobiology (Blixt et al., 2004). It enables the high throughput discovery of carbohydrate ligands and simultaneously allows exploration of structure function relationships. Several requests to screen the Consortium for Functional Glycomics (CFG) mammalian glycan array have been made previously (available on the CFG website). An inspection of that data reveals consistently no high affinity ligands. The investigators hypothesized these results stem from a lack of functional hIntL-1 and the lack of a positive control for carbohydrate binding activity. As the investigators had previously demonstrated functionality of hIntL-1, they envisioned using amine-activated carbohydrate ligands to generate a small furanoside array to run as a positive control alongside the mammalian glycan array v5.1 (FIGS. 10A-D). Ligands were immobilized at varying density using standard succinimidyl-ester coupling to a glass overclip. LNnT and NA2 were used as immobilization controls. Similar specificity was measured under the array format for β-Galf as what was observed when using complementary techniques (FIG. 2A). The small furanoside glycan array afforded conditions to screen hIntL-1 on the CFG mammalian glycan array. Using these conditions, no glycans were bound by hIntL-1 to an extent similar to β-Galf on the furanoside array (FIG. 2A). The highest signal came from a disaccharide GalNAcβ1-6GalNAc ligand. The investigators concluded that the putative binding interactions from this array are nonspecific. No general epitope preferences can be inferred, and increasing the hIntL-1 concentration 4-fold identified different ligands with similarly low signal intensity. These data suggest that of the human glycan ligands screen thus far, none are bound by hIntL-1 with appreciable affinity.

In the absence of human-derived glycan ligands for hIntL-1, the investigators turned to the only available, small microbial glycan array (Stowell et al., 2014). Inspection of the glycans immobilized on the microbial array revealed several candidate ligands that contain Galf. When assayed at the same concentration as the previous arrays, 50 μg/mL, several glycans were bound by hIntL-1 (FIG. 2B). The identified ligands include glycans from *Streptococcus pneumonia, Proteus mirabilis, Proteus vulgaris, Klebsiella pneumonia*, and *Yersinia pestis* (FIG. 2C). Of the top 15 glycan ligands for hIntL-1, several contained the β-Galf epitope, including OPS from *Klebsiella* and capsular polysaccharide from *Streptococcus*. Many other ligands, however, lack Galf. Inspection of the chemical structures of each ligand revealed hIntL-1 has an unexpected affinity for terminal D-glycerol-1-phosphate modified glycans and glycans that contained heptose, D-glycero-D-talo-oct-2-ulosonic acid (Ko), or 3-deoxy-D-manno-oct-2-ulosonic acid (Kdo). Each of these glycan modifications share a terminal vicinal diol epitope with the last carbon being nonstereogenic (FIG. 2D). Every characterized ligand from the top 15 hits contains at least one of these terminal epitopes.

Figure 4:
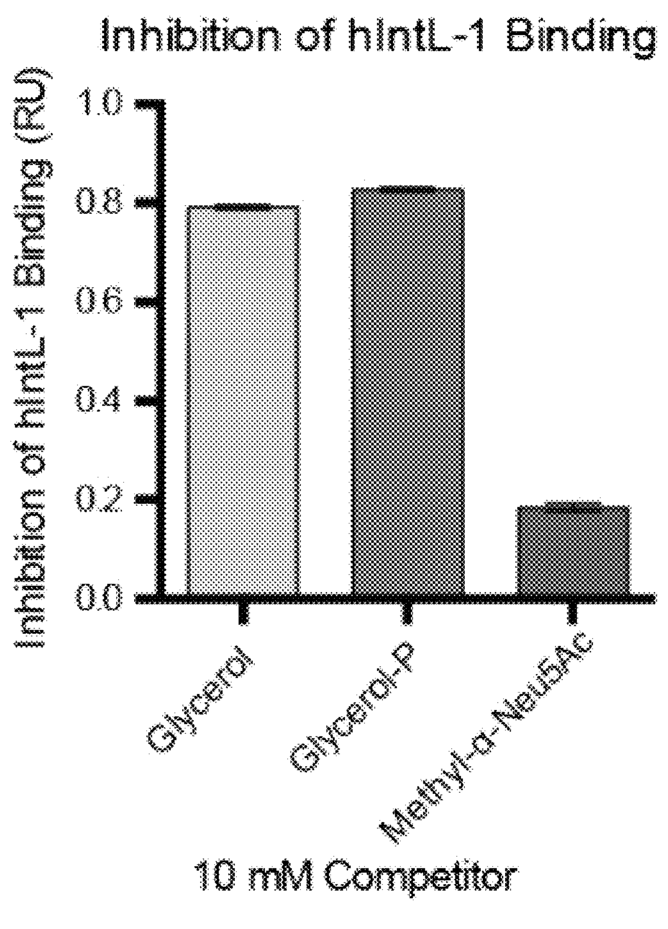
FIG. 4. Competitive binding assay with hIntL-1. Three compounds (glycerol, 1-phosphoglycerol, and α-methyl-glycoside of Neu5Ac) were tested as competitors for hIntL-1 binding to immobilized β-Galf. Error bars represent the s.d. of the mean (n=2).

Each of the ligands discovered in this array are bacteria-specific glycan epitopes. Earlier the investigators discussed microbial Galf biosynthesis. As with Galf, glycerol modification of glycans is not found in humans. And lastly, heptose, Ko, and Kdo are microbe-specific monosaccharides. Specifically, heptose, Kdo, and Ko are conserved components of gram-negative bacterial lipopolysaccharide (LPS) (Schnaitnman et al., 1993). It does not appear that hIntL-1 recognizes a single glycan epitope (FIGS. 12A-B). Rather, the vicinal diols present in the ligands identified here comprise allow broad recognition of many microbes. This may explain why LPS derived glycans appear preferentially in the top half of ligands from the microbial glycan array. Despite the apparent simplicity of ligand recognition, other factors such as sterics are involved in binding. For example, the microbial glycan array contains several examples of α-Galf *S. pneumonia* type 22F (array ligand #238) contains a α-Galf residue with the 5- and 6-hydroxyl free to bind hIntL-1 (FIGS. 12A-B). Inspection of the data reveals this is the $301^{st}$ ranked ligand on the array, with an average signal of −9.6 RFU. Additional examples of hindered binding to α-Galf include *E. coli* O85 (#295), *Salmonella enterica* O17 (#299), and *Shigella boydii* type 3 (#196); each contains a terminal α-Galf residue but resulted in signals of only 49, 66, and 26 RFU, respectively (FIGS. 12A-B). The investigators suspect the inverted stereochemistry at the anomeric carbon of Galf generates a steric block that prevents binding. Another interesting example of specificity is the lack of affinity for N-acetyl-neuraminic acid (Neu5Ac, 6) in the mammalian glycan array and ELISA (FIGS. 4 and 15A-B). Both Kdo and Neu5Ac belong to the 2-keto-3-deoxy-sugar acid family and contain terminal vicinal diols. A structural difference between these sugars is the replacement of the 5-hydroxyl with a 5-N-acetyl group. This substituent adds steric bulk to the monosaccharide. Another difference is the relative orientation of the carboxylate and the anomeric substituent. The differences in sterics and conformation, may prevent hIntL-1 binding. In other species, the 5-N-acetyl group can vary, such as for mice where it is N-glycolyl.

How hIntL-1 binds carbohydrates was an open question. A search of solved protein structures yielded no candidate template. This is not surprising as there was no structural information available for intelectin proteins or the newly termed X-type sequence motif (22). To this end, the investigators obtained a protein x-ray crystal structure of hIntL-1. Strep-tag II hIntL-1 was purified from transiently transfected suspension HEK 293T (FIGS. 11A-E). After optimization around a lead condition, apo crystals that diffract to 1.8 Å were obtained. Unfortunately, the data could not be phased using structures available in the protein data bank (PDB). The investigators thus turned to *Xenopus laevis* intelectin 1 (XIntL-1) expressed in *Trichoplusia ni* cells using methione dropout medium supplemented with exogenous L-selenomethione. The result was the first structure of an X-type lectin.

It reveals the protein forms a disulfide linked trimer with the carbohydrate binding sites located on a single face. The orientation of the carbohydrate-binding sites is consistent with the ability of hIntL-1 to bind avidly to microbial surfaces. The structure reveals why the lectin binds to glycans with terminal 1,2 diols. There is a calcium ion in the binding site to which the terminal 1,2-diol of the glycan coordinates.

Purification of hIntL-1 on a Sorbitol::sepharose Column. Divinyl sulfone activated sepharose was purchased from US Biological (Salem, Mass.; Cat. no. WU6752). Resin was washed three times with doubly distilled water. Resin was then washed with two resin volumes of 100 mM sodium bicarbonate (pH 10.0). The resin was generated via incubation of resin in a solution of 100 mM sodium bicarbonate (pH 10.0) plus 20 mg/mL sorbitol at 4° C. for at least 18 hours. The resin was washed with the bicarbonate solution. The resin was blocked via incubation of resin in a solution of 100 mM Tris-base (pH 9.5) at 4° C. for at least 4 hours. The resin can then be washed, stored in buffer, and is ready for use.

Human intelectin-1 was bound to the resin through incubation of hintL-1 conditioned culture media plus 10 mM $CaCl_2$. The resin was washed with 10 column volumes of 20 mM HEPES (7.4) 150 mM NaCl, 10 mM $CaCl_2$. Bound hIntL-1 was eluted using 10 column volumes of 20 mM HEPES (7.4) 150 mM NaCl, 15 mM EDTA.

Example 3

Glycan Synthetic Procedures

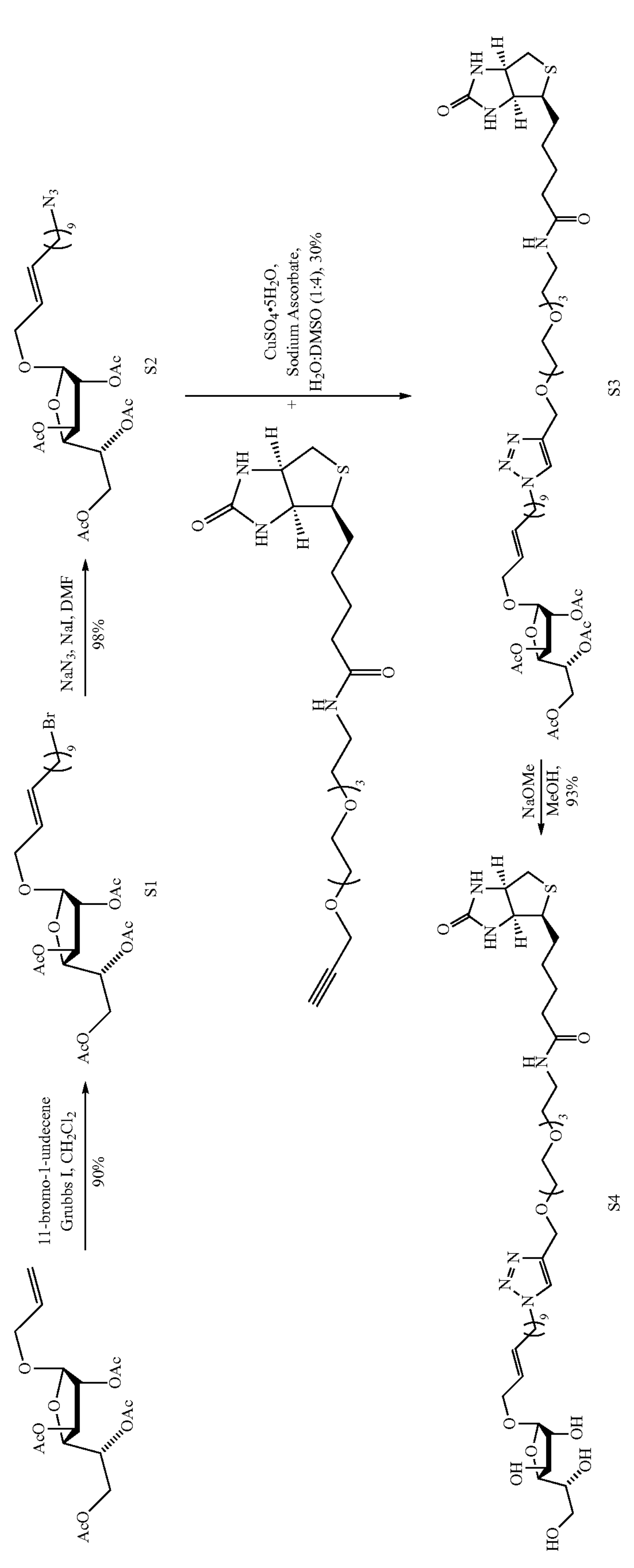
S1 S2 S3 S4

12-Bromo-dodec-2-enyl 2,3,5,6-tetra-O-acetyl-β-D-galactofuranoside (Compound S1)

To a solution of 1-allyl-2,3,5,6-tetra-O-acetyl-β-D-galactofuranose (45) (213 mg, 0.55 mmol) in $CH_2Cl_2$ (5.4 mL) was added 11-bromo-1-undecene (0.6 mL, 2.7 mmol) and Grubbs first generation catalyst (31 mg, 0.037 mmol). The reaction mixture was stirred at reflux for 12 h. The reaction mixture was concentrated under reduced pressure and purified by flash chromatography (0-30% gradient EtOAc/hexanes) to provide 294 mg (90%) of S1 as a brown oil. $^1$H-NMR (300 MHz, $CDCl_3$): δ 5.72 (dt, J=15.4, 6.6 Hz, 1H), 5.56-5.44 (m, 1H), 5.39 (dt, J=6.8, 4.2 Hz, 1H), 5.10-5.03 (m, 2H), 5.03-4.96 (m, 1H), 4.35 (dd, J=11.8, 4.4, 1H), 4.30-4.10 (m, 3H), 3.96 (dd, J=12.1, 6.8 Hz, 3.41 (t, J=6.8 Hz, 2H), 2.17-1.95 (m, 14H), 1.85 (pent, J=7.0 Hz, 2H), 1.50-1.20 (m, 12H). HRESI-MS calcd for $C_{26}H_{41}BrO_{10}$ $[M+H]^+$ 615.1776; found 615.1776.

12-Azido-dodec-2-enyl 2,3,5,6-tetra-O-acetyl-β-D-galactofuranoside (Compound S2)

Intermediate S1 (366 mg, 0.617 mmol) was dissolved in DMF (2.0 mL). $NaN_3$ (200 mg, 3.09 mmol) and NaI (93 mg, 0.617 mmol) were added and the reaction mixture was stirred at room temperature for 18 h. The reaction was diluted with $CH_2Cl_2$ and washed with a saturated sodium bicarbonate ($NaHCO_3$) solution, water, and brine. The organic phase was dried over magnesium sulfate ($MgSO_4$), and the solvent removed under reduced pressure. The residue was passed through a plug of silica (40% EtOAc/hexanes) to give 335 mg (98%) of compound S2. $^1$H-NMR (300 MHz, $CDCl_3$): δ 5.72 (dt, J=15.4, 6.6 Hz, 1H), 5.56-5.44 (m, 1H), 5.39 (dt, J=6.8, 4.2 Hz, 1H), 5.10-5.03 (m, 2H), 5.03-4.96 (m, 1H), 4.35 (dd, J=11.8, 4.4, 1H), 4.30-4.10 (m, 3H), 3.96 (dd, J=12.1, 6.8 Hz, 3.26 (t, J=7.0 Hz, 2H), 2.17-1.95 (m, 14H), 1.65-1.54 (m, 2H), 1.43-1.23 (m, 12H). HRESI-MS calcd for $C_{26}H_{41}N_3O_{10}$ $[M+H]^+$ 578.2690; found 578.2692.

Biotin-$(PEG)_4$-triazole-dodec-2-enyl 2,3,5,6-tetra-O-acetyl-β-D-galactofuranoside (Compound S3)

Intermediate S2 (6.0 mg, 0.011 mmol) was dissolved in dimethyl sulfoxide (DMSO) (400 μL) and water (100 μL). Biotin-$PEG_4$-alkyne (Click Chemistry Tools, LLC, 5.4 mg, 0.012) was added, followed by $CuSO_4$ $5H_2O$ (0.4 mg) and sodium ascorbate (0.4 mg). The reaction was stirred at room temperature for 22 h. The solvent was removed under reduced pressure, and the crude product was dissolved in MeCN (1 mL). The product was purified by HPLC [Vydac Protein & Peptide C18 column; gradient elution from 5-95% MeCN/water (vol/vol), 0.05% trifluoroacetic acid (TFA) (vol/vol)] to provide 3.3 mg (30%) of S3. $^1$H-NMR (300 MHz, $CDCl_3$): δ 7.58 (s, 1H), 5.72 (dt, J=15.4, 6.8 Hz, 1H), 5.57-5.43 (m, 1H), 5.43-5.30 (m, 1H), 5.23-4.95 (m, 2H), 4.69 (s, 2H), 4.60-4.47 (m, 1H), 4.45-3.82 (m, 8H), 3.80-3.55 (m, 12H), 2.95-2.65 (m, 2H), 2.25-1.96 (m, 16 H), 1.95-1.80 (m, 2H), 1.76-1.50 (m, 6H), 1.49-1.15 (m, 12H), 0.95-0.77 (m, 6H).

Biotin-$(PEG)_4$-triazole-dodec-2-enyl β-D-galactofuranose (Compound S4)

To S3 (3.3 mg, 3.3 μmol) in MeOH (0.2 mL) was added sodium methoxide solution (0.02 mL, 0.5 M in MeOH). The reaction was stirred for 2 h at room temperature and neutralized with Amberlite (IR-120 $H^+$) ion exchange resin, filtered, and concentrated under reduced pressure to provide 2.6 mg (93%) of compound S4. $^1$H-NMR (300 MHz, MeOH-$d_4$): δ 7.96 (s, 1H), 5.71 (dt, J=15.4, 6.8 Hz, 1H), 5.62-5.445 (m, 1H), 4.90 (d, J=1.7 Hz, 1H), 4.64 (s, 2H), 4.49 (ddd, J=7.9, 5.0, 0.7 Hz, 1H), 4.40 (t, J=7.1 Hz, 2H), 4.30 (dd, J=7.9, 4.4 Hz, 1H), 4.14 (ddd, J=12.0, 5.5, 0.8 Hz, 1H), 4.03-3.87 (m, 3H), 3.67-3.60 (m, 12H), 3.53 (t, J=5.4 Hz, 2H), 3.35 (t, J=5.3 Hz, 2H), 3.25-3.00 (m, 2H), 3.92 (dd, J=12.8, 5.0 Hz, 1H), 2.70 (d, J=12.7 Hz, 1H), 2.21 (t, J=7.4 Hz, 2H), 2.10-2.00 (m, 2H), 1.95-1.80 (m, 2H), 1.75-1.50 (m, 6H), 1.36-1.15 (m, 12H), 0.96-0.80 (m, 6H). HRESI-MS calcd for $C_{39}H_{68}N_6O_{12}S$ $[M+Na]^+$ 867.4509; found 867.4515.

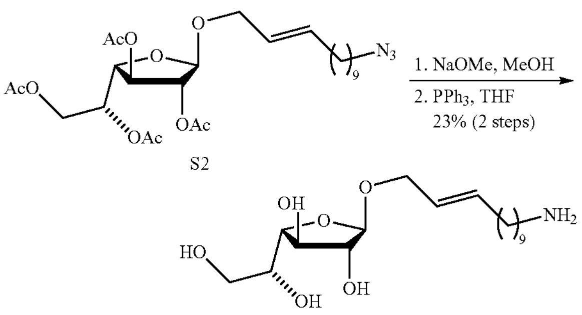

S2

S5

12-Amino-dodecyl β-D-galactofuranoside (Compound S5)

To intermediate S2 (297 mg, 0.54 mmol) was added sodium methoxide solution (2.0 mL, 0.5 M in MeOH). The reaction was stirred for 1.5 h at room temperature and neutralized with Amberlite (IR-120 $H^+$) ion exchange resin, filtered, and concentrated under reduced pressure. The crude mixture was dissolved in wet THF (1.8 mL) and triphenylphosphine (420 mg, 1.61 mmol) was added. The reaction was stirred under an open atmosphere for 18 h. Compound S5 was produced in 23% yield (44 mg over two steps), with residual triphenylphosphine oxide present. $^1$H-NMR (300 MHz, $D_2O$): δ 5.71 (dt, J=15.4, 6.6 Hz, 1H), 5.54 (dtd, J=15.3, 6.2, 1.2 Hz, 1H), 4.90 ($H_{anomeric}$ under $D_2O$ signal, 1H) 4.13 (broad ddd, J=12.1, 5.5, 1.0 Hz, 1H), 4.03-3.99 (m, 1H), 3.98-3.90 (m, 3H), 3.75-3.67 (m, 1H), 3.65-3.59 (m, 2H), 2.74 (t, J=7.3 Hz, 2H), 2.04 (q, J=6.8 Hz, 2H), 1.62-1.47 (m, 2H), 1.35-1.25 (m, 12H). HRESI-MS calcd for $C_{18}H_{35}NO_6$ $[M+H]^+$ 362.2538; found 362.2537.

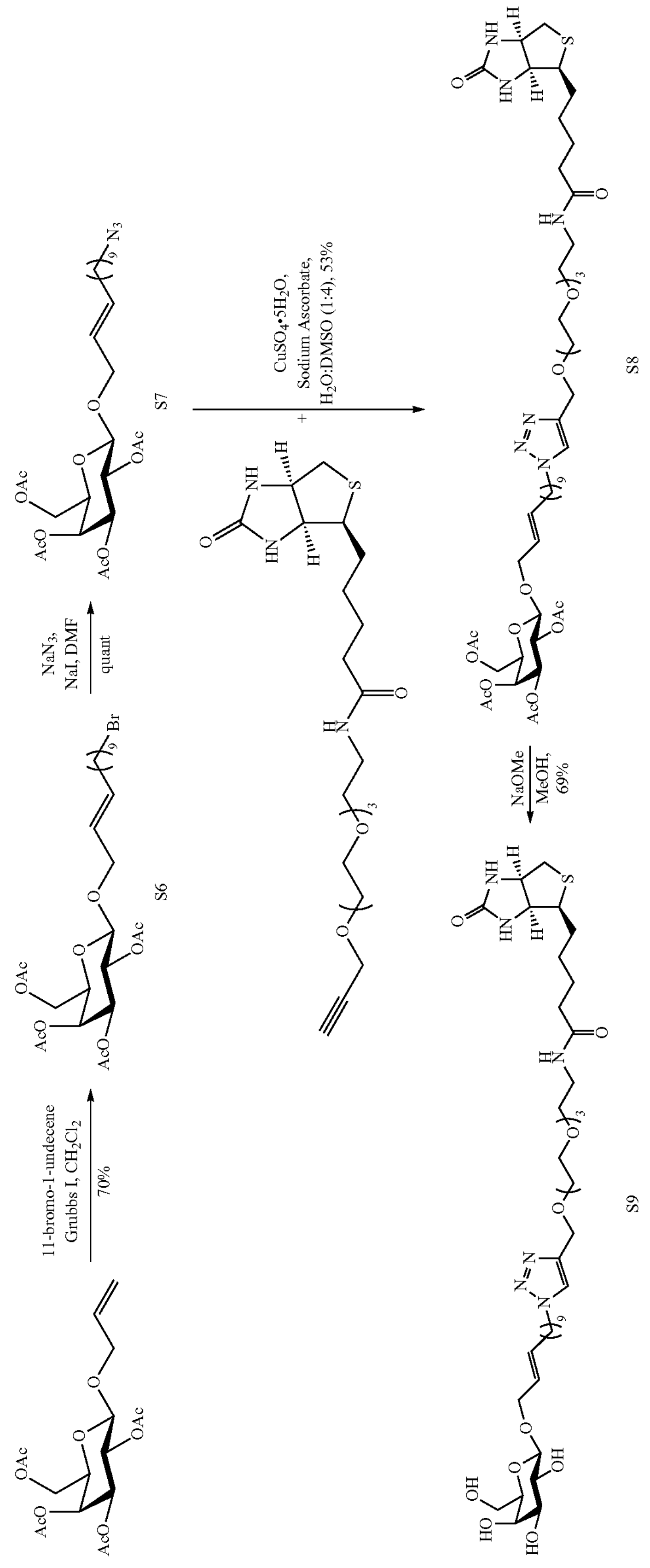
S6
S7
S8
S9

12-Bromo-dodec-2-enyl 2,3,5,6-tetra-O-acetyl-β-D-galactopyranoside (Compound S6)

To a solution of 1-allyl-2,3,5,6-tetra-O-acetyl-β-D-galactopyranoside (45, 46) 208 mg, 0.54 mmol) in $CH_2Cl_2$ (5.4 mL) was added 11-bromo-1-undecene (0.6 mL, 2.7 mmol) and Grubbs first generation catalyst (31 mg, 0.037 mmol). The reaction mixture was stirred at reflux for 12 h. The reaction mixture was concentrated under reduced pressure and purified by flash chromatography [0-30% gradient EtOAc/hexanes) to provide 223 mg (70%) of S6 as a brown oil. $^1$H-NMR (300 MHz, $CDCl_3$): δ 5.69 (dt, J=15.4, 6.7 Hz, 1H), 5.55-5.32 (m, 2H), 5.23 (10.4, 8.0 Hz, 1H), 5.02 (dd, J=10.4, 3.4 Hz, 1H), 4.51 (d, J=8.0 Hz, 1H), 4.29 (dd, J=13.0, 6.5 Hz, 1H), 4.24-3.96 (m, 3H), 3.88 (t, J=7.3 Hz, 1H), 3.41 (t, J=6.9 Hz, 2H), 2.15 (s, 3H), 2.11-2.01 (m, 8H), 1.98 (s, 3H), 1.86 (pent, J=5.8 Hz, 2H), 1.50-1.10 (m, 12H).

12-Azido-dodec-2-enyl 2,3,5,6-tetra-O-acetyl-β-D-galactopyranoside (Compound S7)

Compound S6 (134 mg, 0.23 mmol) was dissolved in DMF (0.8 mL). $NaN_3$ (75 mg, 1.15 mmol) and NaI (35 mg, 0.23 mmol) were added. The reaction mixture was stirred at room temperature for 16 h. The solvent was removed under reduced pressure to give quantitative yield of S7. $^1$H-NMR (300 MHz, $CDCl_3$): δ 5.69 (dt, J=15.4, 6.7 Hz, 1H), 5.55-5.32 (m, 2H), 5.23 (10.4, 8.0 Hz, 1H), 5.02 (dd, J=10.4, 3.4 Hz, 1H), 4.51 (d, J=8.0 Hz, 1H), 4.29 (dd, J=13.0, 6.5 Hz, 1H), 4.24-3.96 (m, 3H), 3.88 (t, J=7.3 Hz, 1H), 3.26 (t, J=6.9 Hz, 2H), 2.15 (s, 3H), 2.11-2.01 (m, 8H), 1.98 (s, 3H), 1.65-1.54 (m, 2H), 1.50-1.10 (m, 12H).

Biotin-$(PEG)_4$-triazole-dodec-2-enyl 2,3,5,6-tetra-O-acetyl-β-D-galactopyranoside (Compound S8)

Compound S7 (6.0 mg, 0.011 mmol) was dissolved in DMSO (400 μL) and water (100 μL). Biotin-PEG4-alkyne (5.4 mg, 0.012 mmol) was added, followed by $CuSO_4$ $5H_2O$ (0.4 mg) and sodium ascorbate (0.4 mg). The reaction was stirred at room temperature for 22 h. The solvent was removed under reduced pressure, and the crude product was dissolved in MeCN (1 mL). The product was purified by HPLC [Vydac, Protein & Peptide C18 column; gradient elution from 5-95% MeCN/water (vol/vol), 0.05% TFA (vol/vol)] to provide 5.8 mg (53%) of S8. (300 MHz, CDCl3): δ 7.59 (s, 1H), 5.68 (dt, J=15.3, 6.8 Hz, 1H), 5.54-5.34 (m, 2H), 5.22 (dd, J=9.5, 7.9 Hz, 1H), 5.01 (dd, J=10.4, 3.4 Hz, 1H), 4.70 (s, 2H), 4.55-4.45 (m, 2H), 4.40-3.95 (m, 6H), 3.89 (td, J=6.4, 1.0, 1H), 3.77-3.56 (m, 12H), 3.43 (broad s, 2H), 3.20-3.05 (m, 1H), 2.97-2.80 (m, 1H), 2.71 (broad d, J=13.4 Hz, 1H), 2.24-2.13 (m, 6H), 2.11-1.95 (m, 11H), 1.94-1.80 (m, 2H), 1.76-1.54 (m, 4H), 1.52-1.15 (m, 12H).

Biotin-$(PEG)_4$-triazole-dodec-2-enyl β-D-galactopyranoside (Compound S9)

To S8 (5.8 mg, 0.57 μmol) in MeOH (0.2 mL) was added sodium methoxide solution (0.03 mL, 0.5 M in MeOH). The reaction was stirred for 2 h at room temperature and neutralized with Amberlite (IR-120 $H^+$) ion exchange resin, filtered, and concentrated under reduced pressure to provide 3.3 mg (69%) of compound S9. (300 MHz, MeOH-$d_4$): δ 8.00 (s, 1H), 5.74 (dt, J=15.4, 6.8 Hz, 1H), 5.64-5.52 (m, 1H), 4.65 (s, 1H), 4.50 (dd, J=7.9, 4.7 Hz, 1H), 4.41 (t, J=7.1 Hz, 2H), 4.35-4.20 (m, 3H), 4.09 (dd, J=12.0, 6.7 Hz, 1H), 3.83 (dd, J=3.2, 1.0 Hz, 1H), 3.76-3.72 (m, 2H), 3.67-3.60 (m, 12H), 3.56-3.41 (m, 5H), 3.38 (t, J=5.0 Hz, 2H), 2.23-3.16 (m, 1H), 2.92 (dd, J=12.8, 5.0, 1H), 2.70 (d, J=12.7 Hz, 1H), 2.21 (t, J=7.3 Hz, 2H), 2.04 (broad q, J=6.7 Hz, 2H), 1.91 (broad pent, J=7.0 Hz, 2H), 1.75-1.50 (m, 6H), 1.40-1.20 (m, 12H), 0.95-0.80 (m, 6H). HRESI-MS calcd for $C_{39}H_{68}N_6O_{12}S$ $[M+Na]^+$ 867.4509; found 867.4481.

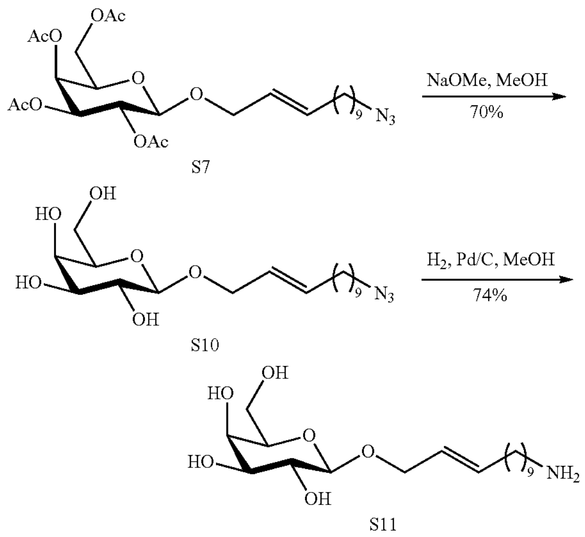

12-Azido-dodec-2-enyl-β-D-galactopyranoside (Compound S10)

To intermediate S7 (129 mg, 0.23 mmol) in MeOH (1 mL) was added sodium methoxide solution (1 mL, 0.5 M in MeOH). The reaction was stirred for 1.5 h at room temperature and neutralized with Amberlite (IR-120 $H^+$) ion exchange resin, filtered, and concentrated under reduced pressure. Purification by flash chromatography (10% $MeOH/CH_2Cl_2$) provided 61 mg (70%) of S10 as a white solid. $^1$H-NMR (300 MHz, $CDCl_3$): δ 5.72 (dt, J=15.4, 6.6 Hz, 1H), 5.65-5.47 (m, 1H), 4.40-4.19 (m, 2H), 4.07 (dd, J=11.8, 6.8 Hz, 1H), 3.97 (broad s, 1H), 3.80-3.64 (m, 2H), 3.64-3.40 (m, 3H), 3.26 (t, J=6.9 Hz, 2H), 2.04 (broad q, J=6.8 Hz, 2H), 1.60 (pent, J=7.2 Hz, 2H), 1.45-1.15 (m, 12H).

12-Amino-dodec-2-enyl-β-D-galactopyranoside (Compound S11)

Intermediate S10 (8.7 mg, 0.022 mmol) was dissolved in MeOH (0.1 mL) under argon. Palladium (10% on carbon, 2 mg) was added. The flask was flushed with $H_2$ and then fitted with a balloon of $H_2$. The reaction mixture was stirred at room temperature for 13 h. The reaction was filtered through celite, and the solvent was removed under reduced pressure to provide 5.9 mg (74%) of S11. $^1$H-NMR (300 MHz, MeOH-$d_4$): δ 4.20 (d, J=7.1 Hz, 1H), 3.89 (dt, J=9.5, 6.8 Hz, 1H), 3.82 (dd, J=3.0, 0.9 Hz, 1H), 3.76-3.70 (m, 2H), 3.59-3.45 (m, 4H), 2.73 (t, J=7.1 Hz, 2H), 1.70-1.20 (m, 20H). HRESI-MS calcd for $C_{18}H_{37}NO_6$ $[M+H]^+$ 364.2694; found 364.2687.

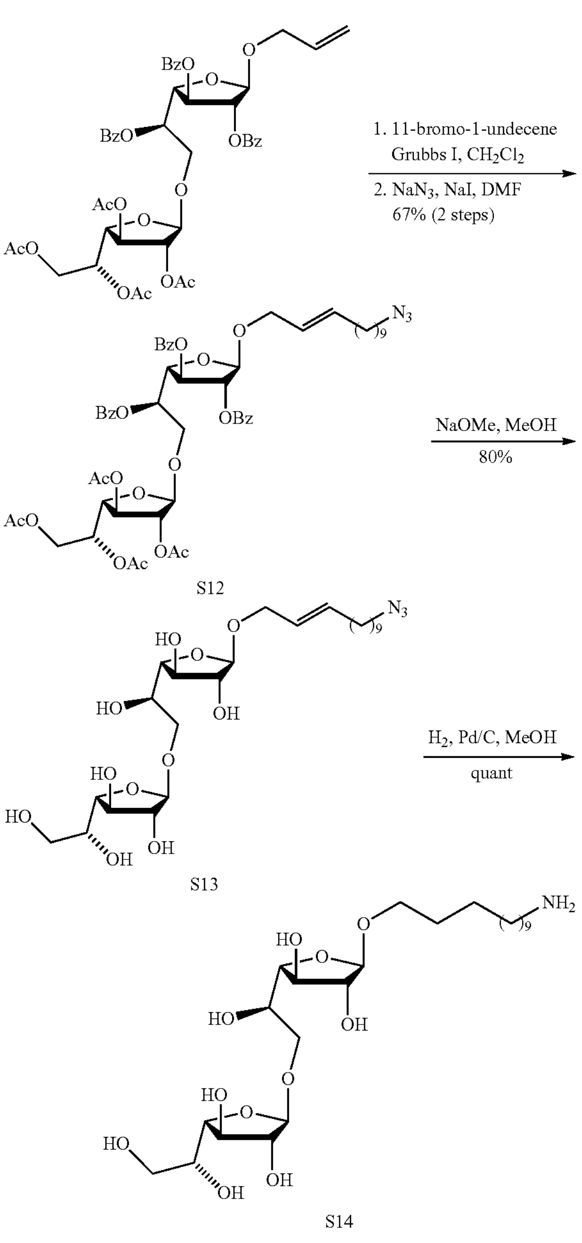

S12

S13

S14

12-Azido-dodec-2-enyl 2,3,5-tri-O-benzoyl-β-D-galactofuranosyl-(1,6)-2,3,5,6-tetra-O-acetyl-β-D-galactofuranoside (Compound 12)

To a solution of 1-allyl-2,3,5-tri-O-benzoyl-β-D-galactofuranosyl-(1,6)-2,3,5,6-tetra-O-acetyl-β-D-galactofuranoside (45) (86 mg, 0.10 mmol) in $CH_2Cl_2$ (1.0 mL) was added 11-bromo-1-undecene (110 μL, 0.50 mmol) and Grubbs first generation catalyst (6 mg, 0.007 mmol). The reaction mixture was stirred at reflux for 14 h. Additional catalyst (5 mg) was added, and stirring continued for 2 h. The reaction mixture was concentrated under reduced pressure and purified by flash chromatography (0→30% gradient EtOAc/hexanes) to provide 75 mg (71%) as a brown oil.

The bromo intermediate (63 mg, 0.059 mmol) was dissolved in DMF (0.2 mL). $NaN_3$ (19 mg, 0.29 mmol) and NaI (9 mg, 0.059 mmol) were added. The reaction mixture was stirred at room temperature for 18 h. The reaction was diluted with $CH_2Cl_2$ and washed with saturated $NaHCO_3$ solution, water, and brine. The organic phase was dried over $MgSO_4$, and the solvent removed under reduced pressure to give 58 mg (95%) of S12. $^1$H-NMR (300 MHz, $CDCl_3$): δ 8.12-8.02 (m, 4H), 7.93-7.83 (m, 2H), 7.61-7.42 (m, 3H), 7.42-7.38 (m, 2H), 7.38-7.22 (m, 4H), 5.90-5.72 (m, 2H), 5.66-5.52 (m, 2H), 5.50-5.45 (m, 1H), 5.41-5.30 (m, 2H), 5.10 (s, 1H), 5.02-4.97 (m, 1H), 4.95 (dd, J=5.4, 1.4 Hz, 1H), 4.64 (dd, J=5.2, 3.5 Hz, 1H), 4.37-4.13 (m, 4H), 4.12-4.00 (m, 2H), 3.93 (dd, J=10.4, 6.8 Hz, 1H), 3.25 (t, J=6.9 Hz, 2H), 2.12-1.99 (m, 11H), 1.96 (s, 3H), 1.56 (pent, J=7.3 Hz, 2H), 1.40-1.20 (m, 12H).

12-Azido-dodec-2-enyl β-D-galactofuranosyl-(1,6)-β-D-galactofuranoside (Compound S13)

To intermediate S12 (47 mg, 0.046 mmol) in MeOH (0.5 mL) was added sodium methoxide solution (0.4 mL, 0.5 M in MeOH). The reaction was stirred for 2 h at room temperature and neutralized with Amberlite (IR-120 H$^+$) ion exchange resin, filtered, and concentrated under reduced pressure. Purification by flash chromatography (20% MeOH/$CH_2Cl_2$) provided 20 mg (80%) of S13 as a white solid. $^1$H-NMR (300 MHz, $D_2O$): δ 5.68 (dt, J=15.3, 6.7 Hz, 1H), 5.55-5.44 (m, 1H), 4.88 (d, J=1.1 Hz, 1H), 4.85 (d, J=1.7 Hz, 1H), 4.14-4.05 (m, 1H), 4.00-3.74 (m, 8H), 3.72-3.65 (m, 1H), 3.62-3.55 (m, 2H), 3.55-3.46 (m, 1H), 3.28-3.19 (m, 3H), 2.01 (q, J=6.8 Hz, 2H), 1.54 (pent, J=7.1 Hz, 2H), 1.45-1.20 (m, 12H).

12-Amino-dodecyl β-D-galactofuranosyl-(1,6)-β-D-galactofuranoside (Compound S14)

Compound S13 (28 mg, 0.51 mmol) was dissolved in MeOH (0.3 mL) under argon. Palladium (10% on carbon, 8 mg) was added. The flask was flushed with $H_2$ and then fitted with a balloon of $H_2$. The reaction mixture was stirred at room temperature for 13 h. The reaction was filtered through celite, and the solvent was removed under reduced pressure to provide S14 in quantitative yield (27 mg). $^1$H-NMR (300 MHz, MeOH-$d_4$): δ 4.82 (d, J=1.2 Hz, 1H), 4.74 (d, J=1.8 Hz, 1H), 3.92-3.87 (m, 3H), 3.83 (dd, J=3.9, 1.9 Hz, 1H), 3.80-3.40 (m, 7H), 3.31 (dt, J=9.6, 6.6 Hz, 1H), 2.57 (t, J=7.2 Hz, 2H), 1.54-1.32 (m, 4H), 1.32-1.15 (m, 12H). HRESI-MS calcd for $C_{24}H_{47}NO_{11}$ [M+H]$^+$ 526.3222; found 526.3229.

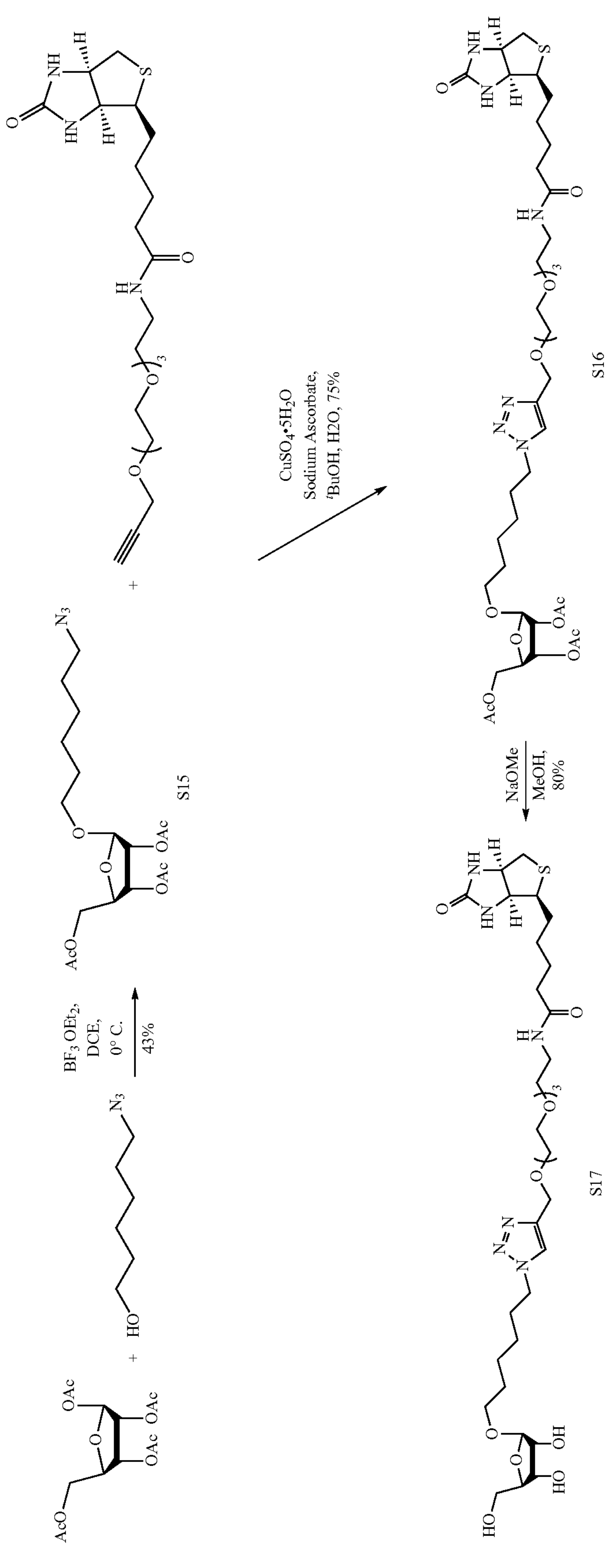
S15
S16
S17

6-Azido-hexyl 2,3,5-tri-O-acetyl-β-D-ribofuranoside (Compound S15)

To a stirring solution of 1,2,3,5-tetra-O-acetyl-β-D-ribofuranoside (200 mg, 0.628 mmol) and 6-azido-1-hexanol (47) (108 mg, 0.754 mmol) in DCE (0.2 M) at 0° C. was added $BF_3$.$OEt_2$ (100 μL, 0.816 mmol). The reaction was stirred for 3.5 h at 0° C. and was then poured into an ice cold mixture of $CH_2Cl_2$ (20 mL) and saturated $NaHCO_3$ (aq, 20 mL). The phases were separated and the aqueous phase was extracted with $CH_2Cl_2$ (3×15 mL). The combined organic phase was dried over sodium sulfate, filtered, and concentrated in vacuo. The residue was purified by flash column chromatography (30% EtOAc/hexanes, $R_f$=0.41). S15 was isolated as an oil (108 mg, 43%). $^1$H-NMR ($CDCl_3$, 300 MHz): δ 5.35-5.27 (m, 1H), 5.22 (dd, J=4.8, 0.7 Hz, 1H), 4.98 (s, 1H), 4.36-4.23 (m, 2H), 4.15-4.03 (m, 1H), 3.75-3.64 (m, 1H), 3.42-3.32 (m, 1H), 3.26 (t, J=6.9 Hz, 2H), 2.14-1.98 (3s, 9H), 1.66-1.48 (m, 4H), 1.45-1.28 (m, 4H). HRESI-MS calcd for $C_{17}H_{27}N_3O_8$ $[M+NH_4]^+$ 424.1691; found 424.1700.

Biotin-(PEG)$_4$-triazole-hexyl 2,3,5-tri-O-acetyl-β-D-ribofuranoside (Compound S16)

To a stirring mixture of intermediate S15 (9.5 mg, 0.024 mmol) and biotin-$PEG_4$-alkyne (11 mg, 0.024 mmol) in $^t$BuOH/$H_2O$ (1:1, 0.07 M) were added sodium ascorbate (4.8 μmol) from a 0.1 M stock solution in $H_2O$ and $CuSO_4$.5$H_2O$ (0.5 μmol) from a 0.01 M stock solution in $H_2O$. The mixture was stirred at room temperature overnight and then concentrated in vacuo. The residue was purified by flash column chromatography (1-100% MeOH/$CH_2Cl_2$). S16 was isolated in 75% yield (15.5 mg). $^1$H-NMR ($CDCl_3$, 300 MHz): δ 7.58 (s, 1H), 6.79 (broad s, 1H), 6.32 (s, 1H), 5.43 (s, 1H), 5.29 (dd, J=6.6, 5.0 Hz, 1H), 5.20 (dd, J=4.8, 0.6 Hz, 1H), 4.96 (s, 1H), 4.67 (s, 2H), 4.53-4.44 (m, 1H), 4.38-4.24 (m, 4H), 4.15-4.03 (m, 1H), 3.75-3.50 (m, 16H), 3.47-3.30 (m, 3H), 3.19-3.08 (m, 1H), 2.89 (dd, J=12.9, 5.1 Hz, 1H), 2.72 (d, J=12.7 Hz, 1H), 2.20 (t, J=7.2 Hz, 2H), 2.14-2.00 (3s, 9H), 1.90 (pent, J=6.9 Hz, 2H), 1.80-1.15 (m, 12H). HRESI-MS calcd for $C_{38}H_{62}N_6O_{14}S$ $[M+Na]^+$ 881.3937; found 881.3838.

Biotin-(PEG)$_4$-triazole-hexyl β-D-ribofuranoside (Compound S17)

To a stirring solution of intermediate S16 (14.6 mg, 0.017 mmol) was added a sodium methoxide solution in MeOH (0.5 M, 34 μL, 0.017 mmol). The mixture was stirred at room temperature for 4 h. The reaction was neutralized with acidic resin (amberlite IR20-H) and filtered through sand, rinsing with MeOH. The filtrate was concentrated under reduced pressure. The residue was purified by flash column chromatography (10→20% MeOH/$CH_2Cl_2$, $R_f$=0.44). S17 was isolated as an oil (10.0 mg, 80%). $^1$H-NMR (MeOH-$d_4$, 300 MHz): δ 7.97 (s, 1H), 4.63 (s, 2H), 4.48 (dd, J=7.8, 4.4 Hz, 1H), 4.40 (t, J=7.0 Hz, 2H), 4.30 (dd, J=7.8, 4.4 Hz, 1H), 4.02 (dd, J=6.7, 4.7 Hz, 1H), 3.92 (td, J=6.7, 3.5, 1H), 3.85 (d, 4.7 Hz, 1H), 3.77-3.46 (m, 18H), 3.36-3.33 (m, 3H), 3.23-3.14 (m, 1H), 2.92 (dd, J=12.7, 5.0 Hz, 1H), 2.69 (d, J=12.7 Hz, 1H), 2.21 (t, J=7.3 Hz, 2H), 1.91 (pent, J=7.2 Hz, 2H), 1.79-1.23 (m, 12H). HRESI-MS calcd for $C_{32}H_{56}N_6O_{11}S$ $[M+Na]^+$ 755.3620; found 755.3612.

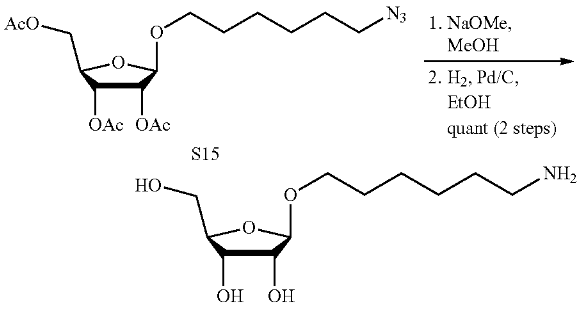

S15

S18

6-Amino-hexyl β-D-ribofuranoside (Compound S18)

To a stirring solution of intermediate S15 (13 mg, 0.032 mmol) in MeOH (0.06 M) was added sodium methoxide (0.5 M in MeOH, 65 μL, 0.032 mmol). The solution was neutralized by the addition of Amberlite $H^+$ resin after 1 h. The resin was removed by filtration through sand with MeOH and the solvent was removed in vacuo. The resulting azide was carried forward to hydrogenation without further purification.

To a stirred solution of the aforementioned azide in ethanol (0.06 M) was added palladium (10% on carbon, 3.4 mg, 0.0032 mmol). The vessel was inerted with $N_2$ and then equipped with a balloon of $H_2$. The mixture was stirred at room temperature for 4 h. The catalyst was removed by filtration through sand/celite, rinsing forward with EtOH. The solvent was removed in vacuo to afford S18 (8.1 mg, quant, 2 steps). $^1$H-NMR (MeOH-$d_4$, 300 MHz): δ 4.87 (s, 1H), 4.06 (dd, J=6.9, 4.8 Hz, 1H), 3.97 (td, J=6.8, 3.5 Hz, 1H), 3.90 (d, 4.6 Hz, 1H), 3.82-3.70 (m, 2H), 3.57 (dd, J=11.8, 6.5 Hz, 1H), 3.44-3.36 (m, 1H), 2.66 (t, J=7.2 Hz, 2H), 1.64-1.45 (m, 4H), 1.45-1.32 (m, 4H). HRESI-MS calcd for $C_{11}H_{23}NO_5$ $[M+H]^+$ 250.1649; found 250.1644.

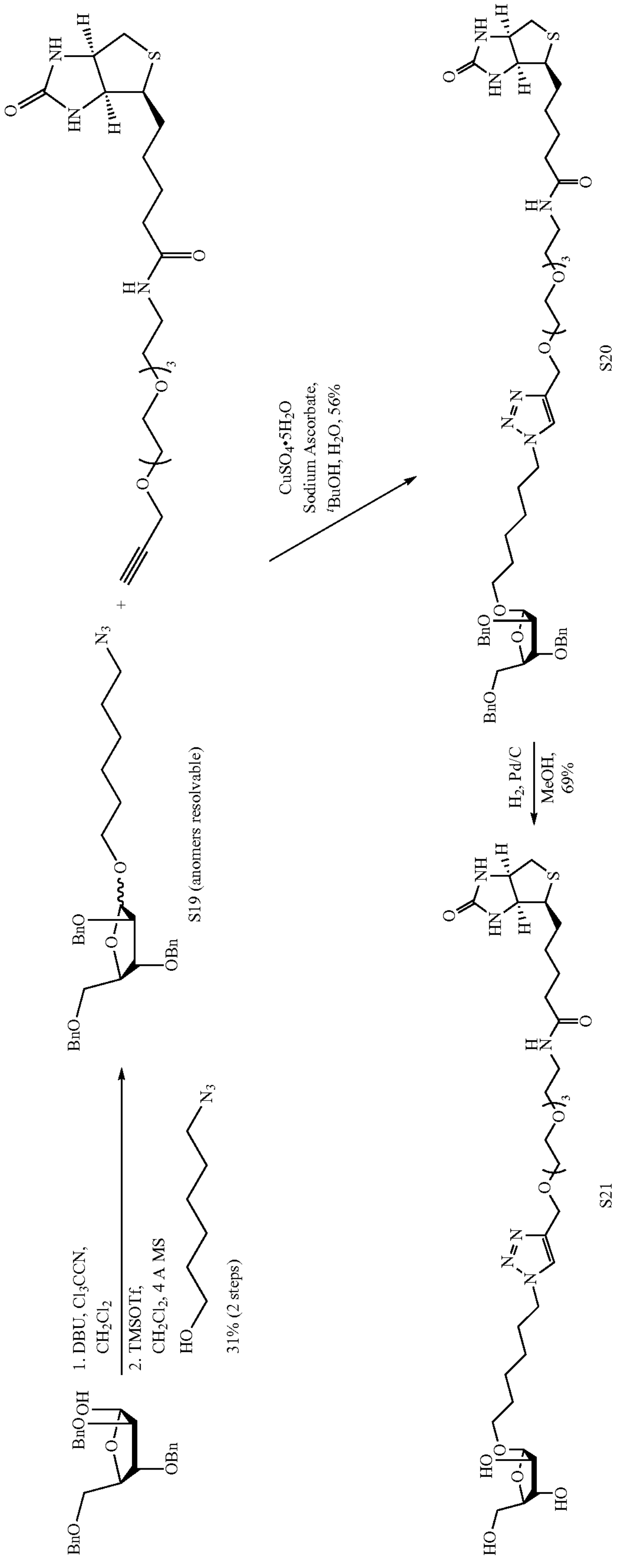
1. DBU, $Cl_3CCN$, $CH_2Cl_2$
2. TMSOTf, $CH_2Cl_2$, 4 A MS
31% (2 steps)
S19 (anomers resolvable)
$CuSO_4$•$5H_2O$
Sodium Ascorbate,
$^tBuOH$, $H_2O$, 56%
S20
$H_2$, Pd/C
MeOH,
69%
S21

6-Azido-hexyl 2,3,5-tri-O-benzyl-β-D-arabinofuranoside (Compound S19)

To a stirring solution of 2,3,5-tri-O-benzyl-β-D-arabinofuranoside (250 mg, 0.594 mmol) in $CH_2Cl_2$ (0.05 M) were added trichloroacetonitrile (298 μL, 2.97 mmol) and DBU (44 μL, concentrated in vacuo and the residue was purified by flash column chromatography (15% EtOAc/hexanes, $R_f$=0.3). The intermediate imidate was isolated as an oil (261 mg, 78%). $^1$H-NMR ($CDCl_3$, 400 MHz): δ 7.40-7.20 (m, 15H), 6.36 (s, 1H), 4.69 (d, J=11.9 Hz, 1H), 4.62-4.53 (m, 4H), 4.50 (d, J=2.0 Hz, 2H), 4.45 (q, J=5.1 Hz, 1H), 4.26 (d, J=2 Hz, 1H), 4.06 (dd, J=5.6, 2.0 Hz, 1H), 3.67 (d, J=4.9 Hz, 1H).

To a stirring solution of the aforementioned imidate (258 mg, 0.457 mmol) and 6-azido-1-hexanol (98 mg, 0.685 mmol) in $CH_2Cl_2$ (0.04 M) at −5° C. were added 4 Å MS and TMSOTf (41 μL, 0.228 mmol). The reaction mixture was stirred for 2 h and DIEA (100 μL) was added. The mixture was filtered through celite with $CH_2Cl_2$ and quenched with saturated $NaHCO_3$ (aq, 20 mL). The phases were separated and the aqueous phase was extracted with $CH_2Cl_2$ (3×20 mL). The combined organic phase was dried over sodium sulfate, filtered, and concentrated. The residue was purified by flash column chromatography (12% EtOAc/hexanes). Both S19α ($R_f$=0.31, 100 mg, 40%) and S19β ($R_f$=0.21, 73 mg, 29%) anomers could be separated. α anomer: $^1$H-NMR ($CDCl_3$, 400 MHz): δ 7.38-7.21 (m, 15H), 5.03 (s, 1H), 4.61-4.52 (m, 4H), 4.48 (dd, J=11.8, 4.2 Hz, 2H), 4.23-4.16 (m, 1H), 4.01 (broad d, J=2.4 Hz, 1H), 3.91 (dd, J=6.8, 3.2 Hz, 1H), 3.77-3.66 (m, 1H), 3.62 (ABX, $J_{AB}$=10.7 Hz, $J_{AX}$=3.7 Hz, $J_{BX}$=5.3 Hz, 2H), 3.45-3.35 (m, 1H), 3.24 (t, J=6.9 Hz, 2H), 1.68-1.51 (m, 4H), 1.42-1.31 (m, 4H). β anomer: $^1$H-NMR ($CDCl_3$, 400 MHz): δ 7.39-7.20 (m, 15H), 4.86 (d, J=4.0 Hz, 1H), 4.70-4.48 (m, 7H), 4.16-4.04 (m, 3H), 3.70-3.62 (m, 1H), 3.53 (broad t, J=2.4H, 1H), 3.35-3.27 (m, 1H), 3.22 (t, J=6.9 Hz, 2H), 1.64-1.50 (m, 4H), 1.41-1.28 (m, 4H). HRESI-MS calcd for $C_{32}H_{39}N_3O_5$ $[M+NH_4]^+$ 563.3228; found 563.3239.

Biotin-(PEG)$_4$-triazole-hexyl 2,3,5-tri-O-benzyl-β-D-arabinofuranoside (Compound S20)

To a stirring solution of S19β (14 mg, 0.025 mmol) and biotin-PEG$_4$-alkyne (11.5 mg, 0.025 mmol) in $^t$BuOH/$H_2O$ (1:1, 0.07 M) were added $CuSO_4.5H_2O$ (0.5 μmol) from a 0.01 M stock solution in $H_2O$ and sodium ascorbate (0.005 mmol) from a 0.01 M stock solution in $H_2O$. THF (~80 μL) was added to solubilize all reaction components. The reaction was stirred at room temperature overnight. The mixture was then concentrated in vacuo. The residue was purified by flash column chromatography (10% MeOH/$CH_2Cl_2$, $R_f$=0.38). S20 was isolated as a white film (14 mg, 56%). $^1$H-NMR ($CDCl_3$, 400 MHz): δ 7.54 (s, 1H), 7.38-7.21 (m, 15H), 6.75 (broad s, 1H), 6.31 (broad s, 1H), 5.40 (broad s, 1H), 5.03 (s, 1H), 4.68 (s, 2H), 4.61-4.41 (m, 7H), 4.31 (t, J=7.2, 3H), 4.21-4.14 (m, 1H), 4.00 (dd, J=3.1, 1.1 Hz, 1H), 3.91 (dd, J=6.8, 3.2 Hz, 1H), 3.73-3.53 (m, 16H), 3.48-3.35 (m, 3H), 3.18-3.07 (m, 1H), 2.88 (dd, J=12.8, 5.0 Hz, 1H), 2.72 (d, J=12.7 Hz, 1H), 2.21 (t, J=7.4 Hz, 2H), 1.89 (pent, J=7.3 Hz, 2H), 1.80-1.51 (m, 6H), 1.51-1.25 (m, 6H). HRESI-MS calcd for $C_{53}H_{74}N_6O_{11}S$ $[M+NH_4]^+$ 1020.5475; found 1020.5458.

Biotin-(PEG)$_4$-triazole-hexyl β-D-arabinofuranoside (Compound S21)

To a stirring solution of S20 (16 mg, 0.016 mmol) in MeOH (0.02 M) was added a drop of glacial acetic acid and palladium (10% on carbon, 17 mg, 0.016 mmol). The vessel was inerted with $N_2$ and equipped with a balloon of $H_2$. The reaction was stirred for 3.5 h at 40° C. then filtered through celite. The filtrate was concentrated in vacuo to provide pure S21 as a colorless film (8.1 mg, 69%). $^1$H-NMR (MeOH-d$_4$, 400 MHz): δ 8.01 (s, 1H), 4.84 (d, J=4.1 Hz, 1H), 4.66 (s, 2H), 4.56-4.46 (broad s, 1H), 4.43 (t, J=7.0 Hz, 2H), 4.35-4.27 (broad s, 1H), 4.02-3.85 (m, 2H), 3.84-3.75 (m, 2H), 3.71-3.53 (m, 16H), 3.47-3.35 (m, 4H), 3.26-3.17 (broad s, 1H), 2.98-2.91 (m, 1H), 2.72 (d, J=2.7 Hz, 1H), 2.23 (broad t, J=7.0 Hz, 2H), 1.94 (pent, J=7.1 Hz, 2H), 1.80-1.55 (m, 6H), 1.50-1.30 (m, 6H). HRESI-MS calcd for $C_{32}H_{56}N_6O_{11}S$ $[M-41]^+$ 733.3801; found 733.3818.

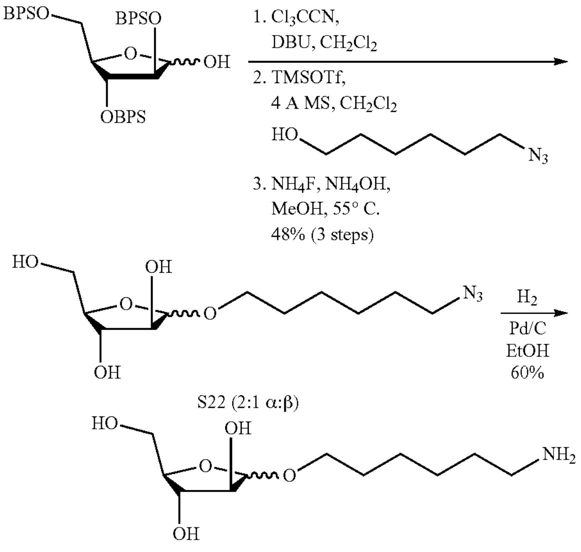

S22 (2:1 α:β)

S23

6-Azido-hexyl D-arabinofuranoside (Compound S22)

To a stirring solution of 2,3,5-tri-O-(tert-butyldiphenylsilyl)-D-arabinofuranoside (48) (19 mg, 0.022 mmol) in $CH_2Cl_2$ (0.05 M) were added trichloroacetonitrile (11 μL, 0.11 mmol) and DBU (2 μL, 0.011 mmol). The reaction was stirred at room temperature overnight, then concentrated in vacuo. The reaction was passed through a plug of silica (5% EtOAc/hexanes) and the filtrate was concentrated to an oil. The crude glycosyl imidate was carried forward immediately without further purification (19 mg).

The aforementioned glycosyl imidate was combined with 6-azido-1-hexanol (4 mg, 0.028 mmol) and dried by evaporation with toluene (3×400 μL). The reagents were taken up in $CH_2Cl_2$ (0.02 M) and 4 Å MS were added. The solution was cooled to −10° C. and a solution of TMSOTf in $CH_2Cl_2$ (0.5 M, 19 μL, 0.0095 mmol) was added. The solution was stirred for 1 h and then filtered through celite into stirring saturated $NaHCO_3$ (aq) with $CH_2Cl_2$. The phases were separated and the aqueous phase was extracted with $CH_2Cl_2$ (3×5 mL). The combined organic phase was dried over sodium sulfate, filtered, and concentrated. The crude residue was carried forward to desilylation without further purification.

The aforementioned glycosylation product was taken up in a solution of concentrated ammonium hydroxide in MeOH (15%, 0.04M, 475 μL). Ammonium fluoride (21 mg, 0.57 mmol) was added and the solution was stirred overnight at 55° C. After cooling to room temperature, $CH_2Cl_2$ (0.5 mL) was added and the precipitated salts were removed by filtration through celite (10% MeOH/$CH_2Cl_2$). The filtrate was concentrated in vacuo. The residue was purified by flash column chromatography (0→8% MeOH/$CH_2Cl_2$, $R_f$=0.55). S22 was isolated as an oil (2.5 mg, 48% over 3 steps, 2:1 α:β). $^1$H-NMR ($CDCl_3$, 400 MHz): δ 5.02 (s, 1H), 4.95 (d, J=4.8 Hz, 0.5 H), 4.22-4.14 (m, 1.5H), 4.05-3.70 (m, 7.5H), 3.70-3.63 (m, 0.5H), 3.57-3.36 (m, 1.5H), 3.27 (t, J=6.8 Hz, 3H), 2.91 (d, J=12.1 Hz, 0.5H), 2.48-2.17 (m, 1.5H), 2.10-1.95 (broad s, 0.5H) 1.67-1.53 (m, 6H), 1.45-1.33 (m, 6H).

6-Amino-hexyl D-arabinofuranoside (Compound S23)

Intermediate S22 (2.2 mg, 0.008 mmol) was taken up in EtOH (0.01 M) and the vessel was inerted with $N_2$. Palladium (10% on carbon, 1 mg, 0.0008 mg) was added and the vessel was re-inerted with $N_2$, then equipped with a balloon of $H_2$. The solution was stirred for 1 h at room temperature. The solution was filtered through celite, then concentrated in vacuo to afford S23 (1.2 mg, 60%). $^1$H-NMR (MeOH-$d_4$, 400 MHz): δ 4.74 (t, J=2.1 Hz, 1H), 3.90-3.77 (m, 2H), 3.74-3.43 (m, 4H), 3.38-3.27 (m, 1H), 2.70-2.51 (m, 1H), 1.67-1.31 (m, 8H). HRESI-MS calcd for $C_{11}H_{23}NO_5$ $[M+H]^+$ 250.1649; found 250.1656.

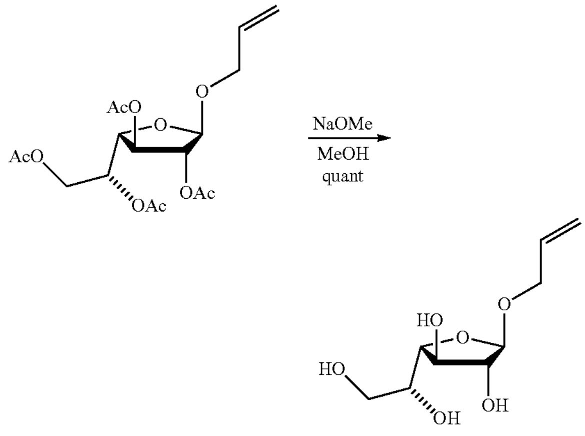

S24

1-Allyl-β-D-galactofuranoside (Compound S24)

To a stirring solution of 1-allyl-2,3,5,6-tetra-O-acetyl-β-D-galactofuranoside (45) (182 mg, 0.469 mmol) in MeOH (0.12 M) was added sodium methoxide (0.5 M in MeOH, 680 μL, 0.234 mmol). The reaction was stirred at room temperature for 2 h and then neutralized by the addition of Amberlite $H^+$ resin. The solution was then filtered and concentrated to afford S24 as an oil (103 mg, quant). $^1$H-NMR (MeOH-$d_4$, 500 MHz): δ 6.00-5.90 (m, 1H), 5.31 (dq, J=17.2, 1.7 Hz, 1H), 5.17 (dq, J=10.5, 1.5 Hz, 1H), 4.92 (d, J=1.8 Hz, 1H), 4.22 (ddt, J=13.1, 5.1, 1.5 Hz, 1H), 4.06-3.98 (m, 3H), 3.95 (dd, J=6.6, 3.3 Hz, 1H), 3.76-3.71 (m, 1H), 3.66-3.61 (m, 2H). HRESI-MS calcd for $C_9H_{16}O_6$ $[M+NH_4]^+$ 238.1286; found 238.1282.

* * *

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VIII. References

The following references, to the extent that they provide exemplary procedural or other details supplementary to those set forth herein, are specifically incorporated herein by reference.

U.S. Pat. No. 5,440,013
U.S. Pat. No. 5,446,128
U.S. Pat. No. 5,475,085
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,840,833
U.S. Pat. No. 5,859,184
U.S. Pat. No. 5,889,155
U.S. Pat. No. 5,929,237
U.S. Pat. No. 7,183,059
U.S. Pat. No. 7,192,713
Bodanszky et al., *J. Antibiot.*, 29(5):549-53, 1976.
Capaldi et al., *Biochem. Biophys. Res. Comm.*, 74(2):425-433, 1977.
Garlatti et al. *EMBO J.*, 26, 623-633, 2007.
Jackson, *Seminars in Oncology*, 24:L164-172, 1997.
Johnson et al., In: *Biotechnology and Pharmacy*, Pezzuto et al., eds., Chapman and Hall, New York, 1993.
Jones et al., *J. Med. Chem.*, 39:904-917, 1996.
Klaassen, In: *The Pharmacological Basis of Therapeutics*, Goodman and Gilman, Eds., Pergamon Press, 8th Ed., 1990.
Krissinel, E. *J. Mol. Biochem.*, 1, 76-85, 2012.
Peptide Synthesis, 1985.
Physicians Desk Reference.
Protective Groups in Organic Chemistry, 1973
Remington's Pharmaceutical Sciences, 15th ed., 1035-1038 and 1570-1580, Mack Publishing Company, P A, 1980.
Robert, X. & Gouet, P. *Nucleic Acids Res.*, 42, W320-W324, 2014.
Schafmeister et al., *J. Amer. Chem. Soc.*, 122(24):5891-5892, 2000.
Solid Phase Peptide Synthelia, 1984
The Merck Index, 11th Edition.
Tsuji et al., *J. Biol. Chem.*, 276, 23456-63, 2001.
Young et al., In: *Handbook of Applied Therapeutics*, 7.1-7.12 and 9.1-9.10, 1989.
Drickamer, K. (1993) *Prog Nucleic Acid Res Mol Biol* 45, 207-232.
Lee et al., (1997) *Glycobiology* 7, 367-372.
Tsuji et al., (2001) *J Biol Chem* 276, 23456-23463.
Thomsen et al., (2011) *Mol Immunol* 48, 369-381.
Pemberton et al., (2004) *Proteomics* 4, 1101-1108.
Datta et al., (2005) *Infect. Immun.* 73, 4025-4033.
Voehringer et al., (2007) *Exp Parasitol* 116, 458-466.

French et al., (2008) *Int. J. Parasitol.* 38, 467-475.
Suzuki et al., (2001) *Biochemistry* 40, 15771-15779.
Pemberton et al., (2008) *J Allergy Clin Immunol* 122, 1033-1034.
Kerr et al., (2014) *Am J Respir Crit Care Med* 189, 1005-1007.
Kuperman et al., (2005) *J Allergy Clin Immunol* 116, 305-311.
Yang et al., (2006) *Am J Physiol Endocrinol Metab* 290, E1253-1261.
Lee et al., (2001) *Glycobiology* 11, 65-73.
Nassau et al., (1996) *J Bacteriol* 178, 1047-1052.
Tefsen et al., (2012) *Glycobiology* 22, 456-469.
Wesener et al., (2013) *Biochemistry* 52, 4391-4398.
Pedersen and Turco, (2003) *Cell Mol Life Sci* 60, 259-266.
Blixt et al., (2004) *Proceedings of the National Academy of Sciences of the United States of America* 101, 17033-17038.
Stowell et al., (2014) *Nature chemical biology* 10, 470-476.
Schnaitman and Klena, (1993) *Microbiological reviews* 57, 655-682.
Vasta et al., (2007) *Advances in experimental medicine and biology* 598, 389-406.

What is claimed is:

1. A method for detecting the presence of a bacterium having glycan epitopes comprising:

(i) contacting a sample comprising human glycans and suspected of containing the bacterium with a human intelectin-1 or -2 molecule, and (ii) detecting selective binding of the human intelectin-1 or -2 molecule to the bacterium.

2. The method of claim 1, wherein the bacterium is *Streptococcus pneumonia, Proteus mirabilis, Proteus vulgaris, Klebsiella pneumonia* or *Yersinia pestis.*

3. The method of claim 1, wherein the bacterium expresses a glycan molecule containing a vicinal 1,2-diol.

4. The method of claim 1, wherein human intelectin binds to a (β-linked D-galactofuranose residue, a glycan containing a heptose, D-glycero-D-talo-oct-2-ulosonic acid (KO) and/or 3-deoxy-D-manno-oct-2-ulosonic acid (KDO) residue, and/or a saccharide residue modified with a phosphoglycerol (Gro-P) substituent.

5. The method of claim 1, wherein the human intelectin is conjugated to a label or reporter.

6. The method of claim 1, wherein the sample comprises a human tissue or body fluid, such as blood or serum.

7. The method of claim 1, wherein the sample comprises a water or waste sample.

8. The method of claim 1, wherein the human intelectin molecule is immobilized on a support.

9. The method of claim 8, wherein the support is a dipstick, bead, chip, microwell, filter, resin, membrane, or quantum dot.

10. A method of detecting a bacterium or mixture of bacteria having glycan epitopes in a sample comprising:

(a) contacting said sample with a human intelectin-1 or -2; and (b) detecting the selective binding of said human intelectin-1 or -2 to a bacterium or mixture of bacteria in said sample.

* * * * *

UNITED STATES PATENT AND TRADEMARK OFFICE

CERTIFICATE OF CORRECTION

PATENT NO. : 10,082,506 B2
APPLICATION NO. : 14/933891
DATED : September 25, 2018
INVENTOR(S) : Laura L. Kiessling et al.

It is certified that error appears in the above-identified patent and that said Letters Patent is hereby corrected as shown below:

In the Claims

In Claim 4, Column 125, Line 49, delete "(β-linked" and insert --β-linked-- therefor.

Signed and Sealed this
Twenty-fifth Day of December, 2018

Andrei Iancu
*Director of the United States Patent and Trademark Office*

SEQUENCE LISTING

```
<160> NUMBER OF SEQ ID NOS: 38

<210> SEQ ID NO 1
<211> LENGTH: 313
<212> TYPE: PRT
<213> ORGANISM: Homo sapiens

<400> SEQUENCE: 1

Met Asn Gln Leu Ser Phe Leu Leu Phe Leu Ile Ala Thr Thr Arg Gly
1               5                   10                  15

Trp Ser Thr Asp Glu Ala Asn Thr Tyr Phe Lys Glu Trp Thr Cys Ser
            20                  25                  30

Ser Ser Pro Ser Leu Pro Arg Ser Cys Lys Glu Ile Lys Asp Glu Cys
        35                  40                  45

Pro Ser Ala Phe Asp Gly Leu Tyr Phe Leu Arg Thr Glu Asn Gly Val
    50                  55                  60

Ile Tyr Gln Thr Phe Cys Asp Met Thr Ser Gly Gly Gly Gly Trp Thr
65                  70                  75                  80

Leu Val Ala Ser Val His Glu Asn Asp Met Arg Gly Lys Cys Thr Val
                85                  90                  95

Gly Asp Arg Trp Ser Ser Gln Gln Gly Ser Lys Ala Val Tyr Pro Glu
            100                 105                 110

Gly Asp Gly Asn Trp Ala Asn Tyr Asn Thr Phe Gly Ser Ala Glu Ala
        115                 120                 125

Ala Thr Ser Asp Asp Tyr Lys Asn Pro Gly Tyr Tyr Asp Ile Gln Ala
    130                 135                 140

Lys Asp Leu Gly Ile Trp His Val Pro Asn Lys Ser Pro Met Gln His
145                 150                 155                 160

Trp Arg Asn Ser Ser Leu Leu Arg Tyr Arg Thr Asp Thr Gly Phe Leu
                165                 170                 175

Gln Thr Leu Gly His Asn Leu Phe Gly Ile Tyr Gln Lys Tyr Pro Val
            180                 185                 190

Lys Tyr Gly Glu Gly Lys Cys Trp Thr Asp Asn Gly Pro Val Ile Pro
        195                 200                 205

Val Val Tyr Asp Phe Gly Asp Ala Gln Lys Thr Ala Ser Tyr Tyr Ser
    210                 215                 220

Pro Tyr Gly Gln Arg Glu Phe Thr Ala Gly Phe Val Gln Phe Arg Val
225                 230                 235                 240

Phe Asn Asn Glu Arg Ala Ala Asn Ala Leu Cys Ala Gly Met Arg Val
                245                 250                 255

Thr Gly Cys Asn Thr Glu His His Cys Ile Gly Gly Gly Gly Tyr Phe
            260                 265                 270

Pro Glu Ala Ser Pro Gln Gln Cys Gly Asp Phe Ser Gly Phe Asp Trp
        275                 280                 285
```

```
Ser Gly Tyr Gly Thr His Val Gly Tyr Ser Ser Ser Arg Glu Ile Thr
    290                 295                 300

Glu Ala Ala Val Leu Leu Phe Tyr Arg
305                 310


<210> SEQ ID NO 2
<211> LENGTH: 325
<212> TYPE: PRT
<213> ORGANISM: Homo sapiens

<400> SEQUENCE: 2

Met Leu Ser Met Leu Arg Thr Met Thr Arg Leu Cys Phe Leu Leu Phe
1               5                   10                  15

Phe Ser Val Ala Thr Ser Gly Cys Ser Ala Ala Ala Ala Ser Ser Leu
            20                  25                  30

Glu Met Leu Ser Arg Glu Phe Glu Thr Cys Ala Phe Ser Phe Ser Ser
        35                  40                  45

Leu Pro Arg Ser Cys Lys Glu Ile Lys Glu Arg Cys His Ser Ala Gly
    50                  55                  60

Asp Gly Leu Tyr Phe Leu Arg Thr Lys Asn Gly Val Val Tyr Gln Thr
65                  70                  75                  80

Phe Cys Asp Met Thr Ser Gly Gly Gly Gly Trp Thr Leu Val Ala Ser
                85                  90                  95

Val His Glu Asn Asp Met Arg Gly Lys Cys Thr Val Gly Asp Arg Trp
            100                 105                 110

Ser Ser Gln Gln Gly Asn Lys Ala Asp Tyr Pro Glu Gly Asp Gly Asn
        115                 120                 125

Trp Ala Asn Tyr Asn Thr Phe Gly Ser Ala Glu Ala Ala Thr Ser Asp
    130                 135                 140

Asp Tyr Lys Asn Pro Gly Tyr Tyr Asp Ile Gln Ala Lys Asp Leu Gly
145                 150                 155                 160

Ile Trp His Val Pro Asn Lys Ser Pro Met Gln His Trp Arg Asn Ser
                165                 170                 175

Ala Leu Leu Arg Tyr Arg Thr Asn Thr Gly Phe Leu Gln Arg Leu Gly
            180                 185                 190

His Asn Leu Phe Gly Ile Tyr Gln Lys Tyr Pro Val Lys Tyr Arg Ser
        195                 200                 205

Gly Lys Cys Trp Asn Asp Asn Gly Pro Ala Ile Pro Val Val Tyr Asp
    210                 215                 220

Phe Gly Asp Ala Lys Lys Thr Ala Ser Tyr Tyr Ser Pro Tyr Gly Gln
225                 230                 235                 240

Arg Glu Phe Val Ala Gly Phe Val Gln Phe Arg Val Phe Asn Asn Glu
                245                 250                 255

Arg Ala Ala Asn Ala Leu Cys Ala Gly Ile Lys Val Thr Gly Cys Asn
            260                 265                 270

Thr Glu His His Cys Ile Gly Gly Gly Gly Phe Phe Pro Gln Gly Lys
        275                 280                 285

Pro Arg Gln Cys Gly Asp Phe Ser Ala Phe Asp Trp Asp Gly Tyr Gly
    290                 295                 300

Thr His Val Lys Ser Ser Cys Ser Arg Glu Ile Thr Glu Ala Ala Val
305                 310                 315                 320

Leu Leu Phe Tyr Arg
                325
```

<210> SEQ ID NO 3
<211> LENGTH: 313
<212> TYPE: PRT
<213> ORGANISM: Mus musculus

<400> SEQUENCE: 3

```
Met Thr Gln Leu Gly Phe Leu Leu Phe Ile Met Val Ala Thr Arg Gly
1               5                   10                  15

Cys Ser Ala Ala Glu Glu Asn Leu Asp Thr Asn Arg Trp Gly Asn Ser
            20                  25                  30

Phe Phe Ser Ser Leu Pro Arg Ser Cys Lys Glu Ile Lys Gln Glu His
        35                  40                  45

Thr Lys Ala Gln Asp Gly Leu Tyr Phe Leu Arg Thr Lys Asn Gly Val
    50                  55                  60

Ile Tyr Gln Thr Phe Cys Asp Met Thr Thr Ala Gly Gly Gly Trp Thr
65                  70                  75                  80

Leu Val Ala Ser Val His Glu Asn Asn Met Arg Gly Lys Cys Thr Val
                85                  90                  95

Gly Asp Arg Trp Ser Ser Gln Gln Gly Asn Arg Ala Asp Tyr Pro Glu
            100                 105                 110

Gly Asp Gly Asn Trp Ala Asn Tyr Asn Thr Phe Gly Ser Ala Glu Ala
        115                 120                 125

Ala Thr Ser Asp Asp Tyr Lys Asn Pro Gly Tyr Phe Asp Ile Gln Ala
    130                 135                 140

Glu Asn Leu Gly Ile Trp His Val Pro Asn Lys Ser Pro Leu His Asn
145                 150                 155                 160

Trp Arg Lys Ser Ser Leu Leu Arg Tyr Arg Thr Phe Thr Gly Phe Leu
                165                 170                 175

Gln His Leu Gly His Asn Leu Phe Gly Leu Tyr Lys Lys Tyr Pro Val
            180                 185                 190

Lys Tyr Gly Glu Gly Lys Cys Trp Thr Asp Asn Gly Pro Ala Leu Pro
        195                 200                 205

Val Val Tyr Asp Phe Gly Asp Ala Arg Lys Thr Ala Ser Tyr Tyr Ser
    210                 215                 220

Pro Ser Gly Gln Arg Glu Phe Thr Ala Gly Tyr Val Gln Phe Arg Val
225                 230                 235                 240

Phe Asn Asn Glu Arg Ala Ala Ser Ala Leu Cys Ala Gly Val Arg Val
                245                 250                 255

Thr Gly Cys Asn Thr Glu His His Cys Ile Gly Gly Gly Gly Phe Phe
            260                 265                 270

Pro Glu Gly Asn Pro Val Gln Cys Gly Asp Phe Ala Ser Phe Asp Trp
        275                 280                 285

Asp Gly Tyr Gly Thr His Asn Gly Tyr Ser Ser Ser Arg Lys Ile Thr
    290                 295                 300

Glu Ala Ala Val Leu Leu Phe Tyr Arg
305                 310
```

<210> SEQ ID NO 4
<211> LENGTH: 313
<212> TYPE: PRT
<213> ORGANISM: Mus musculus

<400> SEQUENCE: 4

```
Met Thr Gln Leu Gly Phe Leu Leu Phe Ile Met Ile Ala Thr Arg Val
1               5                   10                  15

Cys Ser Ala Ala Glu Glu Asn Leu Asp Thr Asn Arg Trp Gly Asn Ser
```

```
            20                  25                  30

Phe Phe Ser Ser Leu Pro Arg Ser Cys Lys Glu Ile Lys Gln Glu Asp
        35                  40                  45

Thr Lys Ala Gln Asp Gly Leu Tyr Phe Leu Arg Thr Glu Asn Gly Val
    50                  55                  60

Ile Tyr Gln Thr Phe Cys Asp Met Thr Thr Ala Gly Gly Gly Trp Thr
65                  70                  75                  80

Leu Val Ala Ser Val His Glu Asn Asn Leu Arg Gly Arg Cys Thr Val
                85                  90                  95

Gly Asp Arg Trp Ser Ser Gln Gln Gly Asn Arg Ala Asp Tyr Pro Glu
            100                 105                 110

Gly Asp Gly Asn Trp Ala Asn Tyr Asn Thr Phe Gly Ser Ala Glu Gly
        115                 120                 125

Ala Thr Ser Asp Asp Tyr Lys Asn Pro Gly Tyr Phe Asp Ile Gln Ala
    130                 135                 140

Glu Asn Leu Gly Ile Trp His Val Pro Asn Asn Ser Pro Leu His Thr
145                 150                 155                 160

Trp Arg Asn Ser Ser Leu Leu Arg Tyr Arg Thr Phe Thr Gly Phe Leu
                165                 170                 175

Gln Arg Leu Gly His Asn Leu Phe Gly Leu Tyr Gln Lys Tyr Pro Val
            180                 185                 190

Lys Tyr Gly Glu Gly Lys Cys Trp Thr Asp Asn Gly Pro Ala Phe Pro
        195                 200                 205

Val Val Tyr Asp Phe Gly Asp Ala Gln Lys Thr Ala Ser Tyr Tyr Ser
    210                 215                 220

Pro Ser Gly Arg Asn Glu Phe Thr Ala Gly Tyr Val Gln Phe Arg Val
225                 230                 235                 240

Phe Asn Asn Glu Arg Ala Ala Ser Ala Leu Cys Ala Gly Val Arg Val
                245                 250                 255

Thr Gly Cys Asn Thr Glu His His Cys Ile Gly Gly Gly Gly Phe Phe
            260                 265                 270

Pro Glu Phe Asp Pro Glu Glu Cys Gly Asp Phe Ala Ala Phe Asp Ala
        275                 280                 285

Asn Gly Tyr Gly Thr His Ile Arg Tyr Ser Asn Ser Arg Glu Ile Thr
    290                 295                 300

Glu Ala Ala Val Leu Leu Phe Tyr Arg
305                 310


<210> SEQ ID NO 5
<211> LENGTH: 322
<212> TYPE: PRT
<213> ORGANISM: Ovis aries

<400> SEQUENCE: 5

Met Pro Ala Gln Gly Pro Gly Val Arg Phe Cys Leu Leu Leu Phe Leu
1               5                   10                  15

Ser Leu Ala Ala Arg Gly Arg Gly Ala Val Thr Pro Ser Val Gly Lys
            20                  25                  30

Phe Trp Gly Asn Glu Ile Cys Ala Pro Phe Leu Ser Phe Leu Pro Arg
        35                  40                  45

Thr Cys Lys Glu Ile Lys Glu Thr Cys His Ser Ala Gly Asp Gly Leu
    50                  55                  60

Tyr His Leu Arg Thr Glu Asn Gly Val Ile Tyr Gln Thr Phe Cys Asp
65                  70                  75                  80
```

```
Met Thr Ser Gly Gly Gly Gly Trp Thr Leu Val Ala Ser Ile His Glu
                85                  90                  95

Asn Asn Met Arg Gly Lys Cys Thr Leu Gly Asp Arg Trp Ser Ser Gln
            100                 105                 110

Gln Gly Asn Arg Ala Asp Tyr Pro Glu Gly Asp Gly Asn Trp Ala Asn
        115                 120                 125

Tyr Asn Thr Phe Gly Ser Ala Glu Ala Ala Thr Ser Asp Asp Tyr Lys
    130                 135                 140

Asn Pro Gly Tyr Tyr Asp Ile Gln Ala Gln Asp Leu Gly Ile Trp His
145                 150                 155                 160

Val Pro Asn Lys Ser Pro Leu Gln His Trp Arg Asn Ser Ser Leu Leu
                165                 170                 175

Arg Tyr His Thr Asn Thr Gly Phe Phe Arg Arg Leu Gly His Asn Leu
            180                 185                 190

Phe Gly Leu Tyr Gln Lys Phe Pro Val Lys Tyr Gly Ala Gly Lys Cys
        195                 200                 205

Trp Thr Asp Asn Gly Pro Ala Ile Pro Val Asp Tyr Asp Phe Gly Asp
    210                 215                 220

Ala Glu Lys Thr Ala Ser Tyr Tyr Ser Pro Asn Gly Gln Arg Glu Phe
225                 230                 235                 240

Val Ala Gly Phe Val Gln Phe Arg Val Phe Asn Asn Glu Gly Ala Ala
                245                 250                 255

Asn Ala Leu Cys Ala Gly Met Arg Val Thr Gly Cys Asn Thr Glu Phe
            260                 265                 270

His Cys Ile Gly Gly Gly Gly Tyr Phe Pro Glu Ser Ser Pro Trp Gln
        275                 280                 285

Cys Gly Asp Phe Ser Ser Phe Asp Trp Asn Gly Tyr Gly Ala His Arg
    290                 295                 300

Gly Tyr Ser Ser Ser Arg Glu Ile Thr Glu Val Ala Val Leu Leu Phe
305                 310                 315                 320

Tyr Arg


<210> SEQ ID NO 6
<211> LENGTH: 339
<212> TYPE: PRT
<213> ORGANISM: Xenopus laevis

<400> SEQUENCE: 6

Met Leu Ser Tyr Ser Leu Leu Leu Leu Ala Leu Ala Phe Pro Ala Gly
1               5                   10                  15

His Ala Gly Ser Cys Glu Gln Ala Ser Ile Ser Glu Lys Lys Glu Lys
            20                  25                  30

Ile Leu Asn Leu Leu Ala Cys Trp Thr Glu Gly Asn Ala Asp Asn Ser
        35                  40                  45

Leu Ser Arg Ser Gly Gly Ser Pro Thr Gly Asp Met Asn Tyr Gly Tyr
    50                  55                  60

Arg Ser Cys Asn Glu Ile Lys Ser Ser Asp Ser Arg Ala Pro Asp Gly
65                  70                  75                  80

Ile Tyr Thr Leu Ala Thr Glu Asp Gly Glu Ser Tyr Gln Thr Phe Cys
                85                  90                  95

Asp Met Thr Thr Asn Gly Gly Gly Trp Thr Leu Val Ala Ser Val His
            100                 105                 110

Glu Asn Asn Met Phe Gly Lys Cys Thr Val Gly Asp Arg Trp Ser Thr
        115                 120                 125
```

-continued

```
Gln Gln Gly Asn Met Leu Gln Asn Pro Glu Gly Asp Gly Asn Trp Ala
    130                 135                 140

Asn Tyr Ala Thr Phe Gly Leu Pro Glu Gly Ala Thr Ser Asp Asp Tyr
145                 150                 155                 160

Lys Asn Pro Gly Tyr Tyr Asp Ile Glu Ala Lys Asn Leu Ala Leu Trp
                165                 170                 175

His Val Pro Asn Lys Thr Pro Met Val Met Trp Arg Asn Ser Ser Ile
            180                 185                 190

Leu Arg Tyr Arg Thr Gln Asn Gly Phe Leu Thr Glu Glu Gly Gly Asn
        195                 200                 205

Leu Phe Glu Leu Tyr Lys Lys Tyr Pro Val Lys Tyr Asp Ile Gly Lys
    210                 215                 220

Cys Leu Ala Asp Asn Gly Pro Ala Val Pro Val Val Tyr Asp Leu Gly
225                 230                 235                 240

Ser Ala Glu Lys Thr Ala Ser Leu Tyr Ser Pro Asn Gly Arg Ser Glu
                245                 250                 255

Phe Thr Pro Gly Phe Val Gln Phe Arg Ala Val Asn Ser Glu Arg Ala
            260                 265                 270

Thr Leu Ala Leu Cys Ala Gly Val Lys Val Lys Gly Cys Asn Val Glu
        275                 280                 285

His His Cys Ile Gly Gly Gly Gly Tyr Ile Pro Glu Gly Ser Pro Arg
    290                 295                 300

Gln Cys Gly Asp Phe Ala Ala Leu Asp Trp Asp Gly Tyr Gly Thr Asn
305                 310                 315                 320

Leu Gly Trp Ser Ala Ser Lys Gln Ile Ile Glu Ala Ala Val Met Leu
                325                 330                 335

Phe Tyr Arg


<210> SEQ ID NO 7
<211> LENGTH: 315
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (54)..(54)
```

```
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid

<400> SEQUENCE: 7

Met Thr Gln Leu Xaa Phe Leu Leu Phe Xaa Xaa Xaa Ala Thr Arg Gly
1               5                   10                  15

Cys Ser Ala Ala Glu Glu Asn Xaa Asp Thr Xaa Xaa Trp Gly Asn Ser
            20                  25                  30

Phe Phe Ser Xaa Xaa Ser Leu Pro Arg Ser Cys Lys Glu Ile Lys Xaa
        35                  40                  45

Glu Cys Xaa Ser Ala Xaa Asp Gly Leu Tyr Phe Leu Arg Thr Glu Asn
    50                  55                  60

Gly Val Ile Tyr Gln Thr Phe Cys Asp Met Thr Xaa Gly Gly Gly Gly
65                  70                  75                  80

Trp Thr Leu Val Ala Ser Val His Glu Asn Asn Met Arg Gly Lys Cys
                85                  90                  95

Thr Val Gly Asp Arg Trp Ser Ser Gln Gln Gly Asn Arg Ala Asp Tyr
            100                 105                 110

Pro Glu Gly Asp Gly Asn Trp Ala Asn Tyr Asn Thr Phe Gly Ser Ala
        115                 120                 125

Glu Ala Ala Thr Ser Asp Asp Tyr Lys Asn Pro Gly Tyr Tyr Asp Ile
    130                 135                 140

Gln Ala Lys Lys Leu Gly Ile Trp His Val Pro Asn Lys Ser Pro Xaa
145                 150                 155                 160

Gln His Trp Arg Asn Ser Ser Leu Leu Arg Tyr Arg Thr Xaa Thr Gly
                165                 170                 175

Phe Leu Gln Arg Leu Gly His Asn Leu Phe Gly Leu Tyr Gln Lys Tyr
            180                 185                 190

Pro Val Lys Tyr Gly Glu Gly Lys Cys Trp Thr Asp Asn Gly Pro Ala
        195                 200                 205

Ile Pro Val Val Tyr Asp Phe Gly Asp Ala Xaa Lys Thr Ala Ser Tyr
    210                 215                 220

Tyr Ser Pro Xaa Gly Gln Arg Glu Phe Thr Ala Gly Phe Val Gln Phe
225                 230                 235                 240

Arg Val Phe Asn Asn Glu Arg Ala Ala Asn Ala Leu Cys Ala Gly Val
                245                 250                 255
```

```
Arg Val Thr Gly Cys Asn Thr Glu His His Cys Ile Gly Gly Gly Gly
            260                 265                 270

Xaa Phe Pro Glu Gly Ser Pro Arg Gln Cys Gly Asp Phe Xaa Ala Phe
        275                 280                 285

Asp Trp Asp Gly Tyr Gly Thr His Val Gly Tyr Ser Ser Ser Arg Glu
    290                 295                 300

Ile Thr Glu Ala Ala Val Leu Leu Phe Tyr Arg
305                 310                 315


<210> SEQ ID NO 8
<211> LENGTH: 299
<212> TYPE: PRT
<213> ORGANISM: Homo sapiens

<400> SEQUENCE: 8

Met Asp Leu Leu Trp Ile Leu Pro Ser Leu Trp Leu Leu Leu Leu Gly
1               5                   10                  15

Gly Pro Ala Cys Leu Lys Thr Gln Glu His Pro Ser Cys Pro Gly Pro
            20                  25                  30

Arg Glu Leu Glu Ala Ser Lys Val Val Leu Leu Pro Ser Cys Pro Gly
        35                  40                  45

Ala Pro Gly Ser Pro Gly Glu Lys Gly Ala Pro Gly Pro Gln Gly Pro
    50                  55                  60

Pro Gly Pro Pro Gly Lys Met Gly Pro Lys Gly Glu Pro Gly Asp Pro
65                  70                  75                  80

Val Asn Leu Leu Arg Cys Gln Glu Gly Pro Arg Asn Cys Arg Glu Leu
                85                  90                  95

Leu Ser Gln Gly Ala Thr Leu Ser Gly Trp Tyr His Leu Cys Leu Pro
            100                 105                 110

Glu Gly Arg Ala Leu Pro Val Phe Cys Asp Met Asp Thr Glu Gly Gly
        115                 120                 125

Gly Trp Leu Val Phe Gln Arg Arg Gln Asp Gly Ser Val Asp Phe Phe
    130                 135                 140

Arg Ser Trp Ser Ser Tyr Arg Ala Gly Phe Gly Asn Gln Glu Ser Glu
145                 150                 155                 160

Phe Trp Leu Gly Asn Glu Asn Leu His Gln Leu Thr Leu Gln Gly Asn
                165                 170                 175

Trp Glu Leu Arg Val Glu Leu Glu Asp Phe Asn Gly Asn Arg Thr Phe
            180                 185                 190

Ala His Tyr Ala Thr Phe Arg Leu Leu Gly Glu Val Asp His Tyr Gln
        195                 200                 205

Leu Ala Leu Gly Lys Phe Ser Glu Gly Thr Ala Gly Asp Ser Leu Ser
    210                 215                 220

Leu His Ser Gly Arg Pro Phe Thr Thr Tyr Asp Ala Asp His Asp Ser
225                 230                 235                 240

Ser Asn Ser Asn Cys Ala Val Ile Val His Gly Ala Trp Trp Tyr Ala
                245                 250                 255

Ser Cys Tyr Arg Ser Asn Leu Asn Gly Arg Tyr Ala Val Ser Glu Ala
            260                 265                 270

Ala Ala His Lys Tyr Gly Ile Asp Trp Ala Ser Gly Arg Gly Val Gly
        275                 280                 285

His Pro Tyr Arg Arg Val Arg Met Met Leu Arg
    290                 295
```

<210> SEQ ID NO 9
<211> LENGTH: 313
<212> TYPE: PRT
<213> ORGANISM: Homo sapiens

<400> SEQUENCE: 9

```
Met Glu Leu Asp Arg Ala Val Gly Val Leu Gly Ala Ala Thr Leu Leu
1               5                   10                  15

Leu Ser Phe Leu Gly Met Ala Trp Ala Leu Gln Ala Ala Asp Thr Cys
            20                  25                  30

Pro Glu Val Lys Met Val Gly Leu Glu Gly Ser Asp Lys Leu Thr Ile
        35                  40                  45

Leu Arg Gly Cys Pro Gly Leu Pro Gly Ala Pro Gly Pro Lys Gly Glu
    50                  55                  60

Ala Gly Thr Asn Gly Lys Arg Gly Glu Arg Gly Pro Pro Gly Pro Pro
65                  70                  75                  80

Gly Lys Ala Gly Pro Pro Gly Pro Asn Gly Ala Pro Gly Glu Pro Gln
                85                  90                  95

Pro Cys Leu Thr Gly Pro Arg Thr Cys Lys Asp Leu Leu Asp Arg Gly
            100                 105                 110

His Phe Leu Ser Gly Trp His Thr Ile Tyr Leu Pro Asp Cys Arg Pro
        115                 120                 125

Leu Thr Val Leu Cys Asp Met Asp Thr Asp Gly Gly Gly Trp Thr Val
    130                 135                 140

Phe Gln Arg Arg Val Asp Gly Ser Val Asp Phe Tyr Arg Asp Trp Ala
145                 150                 155                 160

Thr Tyr Lys Gln Gly Phe Gly Ser Arg Leu Gly Glu Phe Trp Leu Gly
                165                 170                 175

Asn Asp Asn Ile His Ala Leu Thr Ala Gln Gly Thr Ser Glu Leu Arg
            180                 185                 190

Val Asp Leu Val Asp Phe Glu Asp Asn Tyr Gln Phe Ala Lys Tyr Arg
        195                 200                 205

Ser Phe Lys Val Ala Asp Glu Ala Glu Lys Tyr Asn Leu Val Leu Gly
    210                 215                 220

Ala Phe Val Glu Gly Ser Ala Gly Asp Ser Leu Thr Phe His Asn Asn
225                 230                 235                 240

Gln Ser Phe Ser Thr Lys Asp Gln Asp Asn Asp Leu Asn Thr Gly Asn
                245                 250                 255

Cys Ala Val Met Phe Gln Gly Ala Trp Trp Tyr Lys Asn Cys His Val
            260                 265                 270

Ser Asn Leu Asn Gly Arg Tyr Leu Arg Gly Thr His Gly Ser Phe Ala
        275                 280                 285

Asn Gly Ile Asn Trp Lys Ser Gly Lys Gly Tyr Asn Tyr Ser Tyr Lys
    290                 295                 300

Val Ser Glu Met Lys Val Arg Pro Ala
305                 310
```

<210> SEQ ID NO 10
<211> LENGTH: 326
<212> TYPE: PRT
<213> ORGANISM: Homo sapiens

<400> SEQUENCE: 10

```
Met Glu Leu Ser Gly Ala Thr Met Ala Arg Gly Leu Ala Val Leu Leu
1               5                   10                  15

Val Leu Phe Leu His Ile Lys Asn Leu Pro Ala Gln Ala Ala Asp Thr
```

```
            20                  25                  30

Cys Pro Glu Val Lys Val Val Gly Leu Glu Gly Ser Asp Lys Leu Thr
        35                  40                  45

Ile Leu Arg Gly Cys Pro Gly Leu Pro Gly Ala Pro Gly Pro Lys Gly
    50                  55                  60

Glu Ala Gly Val Ile Gly Glu Arg Gly Glu Arg Gly Leu Pro Gly Ala
65                  70                  75                  80

Pro Gly Lys Ala Gly Pro Val Gly Pro Lys Gly Asp Arg Gly Glu Lys
                85                  90                  95

Gly Met Arg Gly Glu Lys Gly Asp Ala Gly Gln Ser Gln Ser Cys Ala
            100                 105                 110

Thr Gly Pro Arg Asn Cys Lys Asp Leu Leu Asp Arg Gly Tyr Phe Leu
        115                 120                 125

Ser Gly Trp His Thr Ile Tyr Leu Pro Asp Cys Arg Pro Leu Thr Val
    130                 135                 140

Leu Cys Asp Met Asp Thr Asp Gly Gly Gly Trp Thr Val Phe Gln Arg
145                 150                 155                 160

Arg Met Asp Gly Ser Val Asp Phe Tyr Arg Asp Trp Ala Ala Tyr Lys
                165                 170                 175

Gln Gly Phe Gly Ser Gln Leu Gly Glu Phe Trp Leu Gly Asn Asp Asn
            180                 185                 190

Ile His Ala Leu Thr Ala Gln Gly Ser Ser Glu Leu Arg Val Asp Leu
        195                 200                 205

Val Asp Phe Glu Gly Asn His Gln Phe Ala Lys Tyr Lys Ser Phe Lys
    210                 215                 220

Val Ala Asp Glu Ala Glu Lys Tyr Lys Leu Val Leu Gly Ala Phe Val
225                 230                 235                 240

Gly Gly Ser Ala Gly Asn Ser Leu Thr Gly His Asn Asn Asn Phe Phe
                245                 250                 255

Ser Thr Lys Asp Gln Asp Asn Asp Val Ser Ser Ser Asn Cys Ala Glu
            260                 265                 270

Lys Phe Gln Gly Ala Trp Trp Tyr Ala Asp Cys His Ala Ser Asn Leu
        275                 280                 285

Asn Gly Leu Tyr Leu Met Gly Pro His Glu Ser Tyr Ala Asn Gly Ile
    290                 295                 300

Asn Trp Ser Ala Ala Lys Gly Tyr Lys Tyr Ser Tyr Lys Val Ser Glu
305                 310                 315                 320

Met Lys Val Arg Pro Ala
                325
```

<210> SEQ ID NO 11
<211> LENGTH: 317
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:

<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(75)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (106)..(107)
<223> OTHER INFORMATION: Xaa can be any naturally occurring amino acid
<220> FEATURE:
<221> NAME/KEY: misc_feature
<222> LOCATION: (109)..(111)
<223> OTHER INFORMATION: Xaa can be any naturally occurring amino acid
<220> FEATURE:
<221> NAME/KEY: misc_feature
<222> LOCATION: (114)..(117)
<223> OTHER INFORMATION: Xaa can be any naturally occurring amino acid
<220> FEATURE:
<221> NAME/KEY: misc_feature
<222> LOCATION: (119)..(126)
<223> OTHER INFORMATION: Xaa can be any naturally occurring amino acid
<220> FEATURE:
<221> NAME/KEY: misc_feature
<222> LOCATION: (133)..(134)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (140)..(144)
<223> OTHER INFORMATION: Xaa can be any naturally occurring amino acid
<220> FEATURE:
<221> NAME/KEY: misc_feature
<222> LOCATION: (147)..(149)
<223> OTHER INFORMATION: Xaa can be any naturally occurring amino acid
<220> FEATURE:
<221> NAME/KEY: misc_feature
<222> LOCATION: (152)..(153)
<223> OTHER INFORMATION: Xaa can be any naturally occurring amino acid
<220> FEATURE:
<221> NAME/KEY: misc_feature
<222> LOCATION: (155)..(158)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (168)..(169)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (174)..(176)
<223> OTHER INFORMATION: Xaa can be any naturally occurring amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (180)..(181)
<223> OTHER INFORMATION: Xaa can be any naturally occurring amino acid
<220> FEATURE:
<221> NAME/KEY: misc_feature
<222> LOCATION: (185)..(186)
<223> OTHER INFORMATION: Xaa can be any naturally occurring amino acid
<220> FEATURE:
<221> NAME/KEY: misc_feature
<222> LOCATION: (189)..(190)
<223> OTHER INFORMATION: Xaa can be any naturally occurring amino acid
<220> FEATURE:
<221> NAME/KEY: misc_feature
<222> LOCATION: (192)..(195)

<223> OTHER INFORMATION: Xaa can be any naturally occurring amino acid
<220> FEATURE:
<221> NAME/KEY: misc_feature
<222> LOCATION: (198)..(199)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (211)..(211)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
<222> LOCATION: (223)..(223)
<223> OTHER INFORMATION: Xaa can be any naturally occurring amino acid
<220> FEATURE:
<221> NAME/KEY: misc_feature
<222> LOCATION: (229)..(229)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (241)..(243)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (252)..(252)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (256)..(257)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid
<220> FEATURE:
<221> NAME/KEY: misc_feature
<222> LOCATION: (271)..(273)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid
<220> FEATURE:
<221> NAME/KEY: misc_feature
<222> LOCATION: (277)..(278)
<223> OTHER INFORMATION: Xaa can be any naturally occurring amino acid
<220> FEATURE:
<221> NAME/KEY: misc_feature
<222> LOCATION: (280)..(280)
<223> OTHER INFORMATION: Xaa can be any naturally occurring amino acid
<220> FEATURE:
<221> NAME/KEY: misc_feature
<222> LOCATION: (282)..(283)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (288)..(289)
<223> OTHER INFORMATION: Xaa can be any naturally occurring amino acid
<220> FEATURE:
<221> NAME/KEY: misc_feature
<222> LOCATION: (304)..(304)
<223> OTHER INFORMATION: Xaa can be any naturally occurring amino acid
<220> FEATURE:
<221> NAME/KEY: misc_feature
<222> LOCATION: (310)..(310)
<223> OTHER INFORMATION: Xaa can be any naturally occurring amino acid
<220> FEATURE:
<221> NAME/KEY: misc_feature
<222> LOCATION: (312)..(312)
<223> OTHER INFORMATION: Xaa can be any naturally occurring amino acid
<220> FEATURE:
<221> NAME/KEY: misc_feature
<222> LOCATION: (315)..(315)
<223> OTHER INFORMATION: Xaa can be any naturally occurring amino acid
<220> FEATURE:
<221> NAME/KEY: misc_feature
<222> LOCATION: (317)..(317)
<223> OTHER INFORMATION: Xaa can be any naturally occurring amino acid

<400> SEQUENCE: 11

```
Xaa Xaa Met Leu Xaa Leu Xaa Phe Leu Leu Leu Leu Xaa Xaa Gly Xaa
1               5                   10                  15

Ala Gly Xaa Xaa Gln Ala Ala Xaa Xaa Cys Pro Glu Val Lys Xaa Trp
            20                  25                  30

Leu Glu Gly Ser Asp Lys Xaa Ser Leu Leu Arg Ser Cys Pro Xaa Ile
        35                  40                  45

Xaa Gly Xaa Xaa Gly Pro Lys Xaa Glu Asp Gly Leu Tyr Xaa Leu Arg
    50                  55                  60

Xaa Glu Xaa Gly Xaa Pro Xaa Gln Xaa Xaa Xaa Asp Xaa Xaa Thr Gly
65                  70                  75                  80

Gly Gly Gly Trp Thr Leu Val Ala Ser Val His Glu Asn Xaa Met Arg
                85                  90                  95

Gly Lys Cys Thr Val Gly Xaa Arg Trp Xaa Xaa Gln Xaa Xaa Xaa Arg
            100                 105                 110

Gly Xaa Xaa Xaa Xaa Gly Xaa Xaa Xaa Xaa Xaa Xaa Xaa Xaa Thr Phe
        115                 120                 125

Gly Leu Pro Glu Xaa Xaa Thr Xaa Asp Xaa Tyr Xaa Xaa Xaa Xaa Xaa
    130                 135                 140

Met Asp Xaa Xaa Xaa Gly Gly Xaa Xaa Val Xaa Xaa Xaa Xaa Asn Xaa
145                 150                 155                 160

Gly Xaa Val Asp Phe Trp Arg Xaa Xaa Ser Leu Xaa Arg Xaa Xaa Xaa
                165                 170                 175

Thr Xaa Gly Xaa Xaa Trp Leu Gly Xaa Xaa Asn Leu Xaa Xaa Leu Xaa
```

```
            180                 185                 190

Xaa Xaa Xaa Pro Val Xaa Xaa Arg Val Gly Xaa Cys Asp Phe Asp Asn
        195                 200                 205

Xaa Pro Xaa Phe Xaa Val Xaa Tyr Asp Phe Gly Xaa Ala Asp Xaa Thr
    210                 215                 220

Ala Ser Tyr Tyr Xaa Pro Leu Gly Glu Phe Thr Xaa Gly Ala Xaa Gln
225                 230                 235                 240

Xaa Xaa Xaa Phe Xaa Asn Glu Arg Ala Phe Ser Xaa Leu Xaa Ala Xaa
                245                 250                 255

Xaa Asp Val Xaa Gly Cys Asn Cys Xaa His His Cys Ile Gly Xaa Xaa
            260                 265                 270

Xaa Tyr Xaa Pro Xaa Xaa Ser Xaa Asn Xaa Xaa Gly Asp Xaa Ala Xaa
        275                 280                 285

Xaa Asp Trp Asp Gly Tyr Gly Thr Gly Ile Gly Trp Ser Ser Ser Xaa
    290                 295                 300

Gly Ile Thr Glu Ala Xaa Val Xaa Leu Phe Xaa Arg Xaa
305                 310                 315


<210> SEQ ID NO 12
<211> LENGTH: 285
<212> TYPE: PRT
<213> ORGANISM: Homo sapiens

<400> SEQUENCE: 12

Trp Thr Cys Ser Ser Ser Pro Ser Leu Pro Arg Ser Cys Lys Glu Ile
1               5                   10                  15

Lys Asp Glu Cys Pro Ser Ala Phe Asp Gly Leu Tyr Phe Leu Arg Thr
            20                  25                  30

Glu Asn Gly Val Ile Tyr Gln Thr Phe Cys Asp Met Thr Ser Gly Gly
        35                  40                  45

Gly Gly Trp Thr Leu Val Ala Ser Val His Glu Asn Asp Met Arg Gly
    50                  55                  60

Lys Cys Thr Val Gly Asp Arg Trp Ser Ser Gln Gln Gly Ser Lys Ala
65                  70                  75                  80

Val Tyr Pro Glu Gly Asp Gly Asn Trp Ala Asn Tyr Asn Thr Phe Gly
                85                  90                  95

Ser Ala Glu Ala Ala Thr Ser Asp Asp Tyr Lys Asn Pro Gly Tyr Tyr
            100                 105                 110

Asp Ile Gln Ala Lys Asp Leu Gly Ile Trp His Val Pro Asn Lys Ser
        115                 120                 125

Pro Met Gln His Trp Arg Asn Ser Ser Leu Leu Arg Tyr Arg Thr Asp
    130                 135                 140

Thr Gly Phe Leu Gln Thr Leu Gly His Asn Leu Phe Gly Ile Tyr Gln
145                 150                 155                 160

Lys Tyr Pro Val Lys Tyr Gly Glu Gly Lys Cys Trp Thr Asp Asn Gly
                165                 170                 175

Pro Val Ile Pro Val Val Tyr Asp Phe Gly Asp Ala Gln Lys Thr Ala
            180                 185                 190

Ser Tyr Tyr Ser Pro Tyr Gly Gln Arg Glu Phe Thr Ala Gly Phe Val
        195                 200                 205

Gln Phe Arg Val Phe Asn Asn Glu Arg Ala Ala Asn Ala Leu Cys Ala
    210                 215                 220

Gly Met Arg Val Thr Gly Cys Asn Thr Glu His His Cys Ile Gly Gly
225                 230                 235                 240
```

-continued

```
Gly Gly Tyr Phe Pro Glu Ala Ser Pro Gln Gln Cys Gly Asp Phe Ser
                245                 250                 255

Gly Phe Asp Trp Ser Gly Tyr Gly Thr His Val Gly Tyr Ser Ser Ser
            260                 265                 270

Arg Glu Ile Thr Glu Ala Ala Val Leu Leu Phe Tyr Arg
        275                 280                 285


<210> SEQ ID NO 13
<211> LENGTH: 217
<212> TYPE: PRT
<213> ORGANISM: Homo sapiens

<400> SEQUENCE: 13

Asn Pro Cys Leu Thr Gly Pro Arg Thr Cys Lys Asp Leu Leu Asp Arg
1               5                   10                  15

Gly His Phe Leu Ser Gly Trp His Thr Ile Tyr Leu Pro Asp Cys Arg
            20                  25                  30

Pro Leu Thr Val Leu Cys Asp Met Asp Thr Asp Gly Gly Gly Trp Thr
        35                  40                  45

Val Phe Gln Arg Arg Val Asp Gly Ser Val Asp Phe Tyr Arg Asp Trp
    50                  55                  60

Ala Thr Tyr Lys Gln Gly Phe Gly Ser Arg Leu Gly Glu Phe Trp Leu
65                  70                  75                  80

Gly Asn Asp Asn Ile His Ala Leu Thr Ala Gln Gly Thr Ser Glu Leu
                85                  90                  95

Arg Thr Asp Leu Val Asp Phe Glu Asp Asn Tyr Gln Phe Ala Lys Tyr
            100                 105                 110

Arg Ser Phe Lys Val Ala Asp Glu Ala Glu Lys Tyr Asn Leu Val Leu
        115                 120                 125

Gly Ala Phe Val Glu Gly Ser Ala Gly Asp Ser Leu Thr Phe His Asn
    130                 135                 140

Asn Gln Ser Phe Ser Thr Lys Asp Gln Asp Asn Asp Leu Asn Thr Gly
145                 150                 155                 160

Asn Cys Ala Val Met Phe Gln Gly Ala Trp Trp Tyr Lys Asn Cys His
                165                 170                 175

Thr Ser Asn Leu Gly Arg Tyr Leu Arg Gly Thr His Gly Ser Phe Ala
            180                 185                 190

Asn Gly Ile Asn Trp Lys Ser Gly Lys Gly Tyr Asn Tyr Ser Tyr Lys
        195                 200                 205

Val Ser Glu Met Lys Val Arg Pro Ala
    210                 215


<210> SEQ ID NO 14
<211> LENGTH: 1689
<212> TYPE: DNA
<213> ORGANISM: Artificial sequence
<220> FEATURE:
<223> OTHER INFORMATION: Synthetic oligonucleotide

<400> SEQUENCE: 14

atgaaccaac tcagcttcct gctgtttctc atagcgacca ccagaggatg gagtacagat      60

gacgtccaac tggtgcagtc aggggctgaa gtgaaaaaac ctggggcctc agtgaaggtg     120

tcctgcaagg cttctggcta cacctttact aggtacacga tgcactgggt aaggcaggca     180

cctggacagg gtctggaatg gattggatac attaatccta gccgtggtta tactaattac     240

gcagacagcg tcaagggccg cttcacaatc actaccgcca aatccaccag cacagcctac     300
```

-continued

```
atggaactga gcagcctgcg ttctgaggac actgcaacct attactgtgc aagatattat    360

gatgatcatt actgccttga ctactggggc caaggcacca cggtcaccgt ctcctcaggc    420

gaaggtacta gtactggttc tggtggaagt ggaggttcag gtggagcaga cgatattgta    480

ctgacccagt ctccagcaac tctgtctctg tctccagggg agcgtgccac cctgagctgc    540

agagccagtc aaagtgtaag ttacatgaac tggtaccagc agaagccggg caaggcaccc    600

aaaagatgga tttatgacac atccaaagtg gcttctggag tccctgctcg cttcagtggc    660

agtgggtctg ggaccgacta ctctctcaca atcaacagct tggaggctga agatgctgcc    720

acttattact gccaacagtg gagtagtaac ccgctcacgt tcggtggcgg gaccaaggtg    780

gagatcaaat ccggaggtgg tggatccgag gctaatactt acttcaagga atggacctgt    840

tcttcgtctc catctctgcc cagaagctgc aaggaaatca aagacgaatg tcctagtgca    900

tttgatggcc tgtattttct ccgcactgag aatggtgtta tctaccagac cttctgtgac    960

atgacctctg gggtggcgg ctggaccctg gtggccagcg tgcacgagaa tgacatgcgt   1020

gggaagtgca cggtgggcga tcgctggtcc agtcagcagg gcagcaaagc agtctaccca   1080

gagggggacg gcaactgggc caactacaac acctttggat ctgcagaggc ggccacgagc   1140

gatgactaca agaaccctgg ctactacgac atccaggcca aggacctggg catctggcac   1200

gtgcccaata agtcccccat gcagcactgg agaaacagct ccctgctgag gtaccgcacg   1260

gacactggct tcctccagac actgggacat aatctgtttg gcatctacca gaaatatcca   1320

gtgaaatatg gagaaggaaa gtgttggact gacaacggcc cggtgatccc tgtggtctat   1380

gattttggcg acgcccagaa aacagcatct tattactcac cctatggcca gcgggaattc   1440

actgcgggat ttgttcagtt cagggtattt aataacgaga gagcagccaa cgccttgtgt   1500

gctggaatga gggtcaccgg atgtaacact gagcaccact gcattggtgg aggaggatac   1560

tttccagagg ccagtcccca gcagtgtgga gatttttctg gttttgattg gagtggatat   1620

ggaactcatg ttggttacag cagcagccgt gagataactg aggcagctgt gcttctattc   1680

tatcgttga                                                           1689
```

<210> SEQ ID NO 15
<211> LENGTH: 562
<212> TYPE: PRT
<213> ORGANISM: Artificial sequence
<220> FEATURE:
<223> OTHER INFORMATION: Synthetic polypeptide

<400> SEQUENCE: 15

```
Met Asn Gln Leu Ser Phe Leu Leu Phe Leu Ile Ala Thr Thr Arg Gly
1               5                   10                  15

Trp Ser Thr Asp Asp Val Gln Leu Val Gln Ser Gly Ala Glu Val Lys
            20                  25                  30

Lys Pro Gly Ala Ser Val Lys Val Ser Cys Lys Ala Ser Gly Tyr Thr
        35                  40                  45

Phe Thr Arg Tyr Thr Met His Trp Val Arg Gln Ala Pro Gly Gln Gly
    50                  55                  60

Leu Glu Trp Ile Gly Tyr Ile Asn Pro Ser Arg Gly Tyr Thr Asn Tyr
65                  70                  75                  80

Ala Asp Ser Val Lys Gly Arg Phe Thr Ile Thr Thr Ala Lys Ser Thr
                85                  90                  95

Ser Thr Ala Tyr Met Glu Leu Ser Ser Leu Arg Ser Glu Asp Thr Ala
            100                 105                 110
```

-continued

```
Thr Tyr Tyr Cys Ala Arg Tyr Tyr Asp Asp His Tyr Cys Leu Asp Tyr
        115                 120                 125

Trp Gly Gln Gly Thr Thr Val Thr Val Ser Ser Gly Glu Gly Thr Ser
    130                 135                 140

Thr Gly Ser Gly Gly Ser Gly Gly Ser Gly Gly Ala Asp Asp Ile Val
145                 150                 155                 160

Leu Thr Gln Ser Pro Ala Thr Leu Ser Leu Ser Pro Gly Glu Arg Ala
                165                 170                 175

Thr Leu Ser Cys Arg Ala Ser Gln Ser Val Ser Tyr Met Asn Trp Tyr
            180                 185                 190

Gln Gln Lys Pro Gly Lys Ala Pro Lys Arg Trp Ile Tyr Asp Thr Ser
        195                 200                 205

Lys Val Ala Ser Gly Val Pro Ala Arg Phe Ser Gly Ser Gly Ser Gly
    210                 215                 220

Thr Asp Tyr Ser Leu Thr Ile Asn Ser Leu Glu Ala Glu Asp Ala Ala
225                 230                 235                 240

Thr Tyr Tyr Cys Gln Gln Trp Ser Ser Asn Pro Leu Thr Phe Gly Gly
                245                 250                 255

Gly Thr Lys Val Glu Ile Lys Ser Gly Gly Gly Gly Ser Glu Ala Asn
            260                 265                 270

Thr Tyr Phe Lys Glu Trp Thr Cys Ser Ser Ser Pro Ser Leu Pro Arg
        275                 280                 285

Ser Cys Lys Glu Ile Lys Asp Glu Cys Pro Ser Ala Phe Asp Gly Leu
    290                 295                 300

Tyr Phe Leu Arg Thr Glu Asn Gly Val Ile Tyr Gln Thr Phe Cys Asp
305                 310                 315                 320

Met Thr Ser Gly Gly Gly Gly Trp Thr Leu Val Ala Ser Val His Glu
                325                 330                 335

Asn Asp Met Arg Gly Lys Cys Thr Val Gly Asp Arg Trp Ser Ser Gln
            340                 345                 350

Gln Gly Ser Lys Ala Val Tyr Pro Glu Gly Asp Gly Asn Trp Ala Asn
        355                 360                 365

Tyr Asn Thr Phe Gly Ser Ala Glu Ala Ala Thr Ser Asp Asp Tyr Lys
    370                 375                 380

Asn Pro Gly Tyr Tyr Asp Ile Gln Ala Lys Asp Leu Gly Ile Trp His
385                 390                 395                 400

Val Pro Asn Lys Ser Pro Met Gln His Trp Arg Asn Ser Ser Leu Leu
                405                 410                 415

Arg Tyr Arg Thr Asp Thr Gly Phe Leu Gln Thr Leu Gly His Asn Leu
            420                 425                 430

Phe Gly Ile Tyr Gln Lys Tyr Pro Val Lys Tyr Gly Glu Gly Lys Cys
        435                 440                 445

Trp Thr Asp Asn Gly Pro Val Ile Pro Val Val Tyr Asp Phe Gly Asp
    450                 455                 460

Ala Gln Lys Thr Ala Ser Tyr Tyr Ser Pro Tyr Gly Gln Arg Glu Phe
465                 470                 475                 480

Thr Ala Gly Phe Val Gln Phe Arg Val Phe Asn Asn Glu Arg Ala Ala
                485                 490                 495

Asn Ala Leu Cys Ala Gly Met Arg Val Thr Gly Cys Asn Thr Glu His
            500                 505                 510

His Cys Ile Gly Gly Gly Gly Tyr Phe Pro Glu Ala Ser Pro Gln Gln
        515                 520                 525

Cys Gly Asp Phe Ser Gly Phe Asp Trp Ser Gly Tyr Gly Thr His Val
```

530 535 540

Gly Tyr Ser Ser Ser Arg Glu Ile Thr Glu Ala Ala Val Leu Leu Phe
545 550 555 560

Tyr Arg

<210> SEQ ID NO 16
<211> LENGTH: 1107
<212> TYPE: DNA
<213> ORGANISM: Artificial sequence
<220> FEATURE:
<223> OTHER INFORMATION: Synthetic oligonucleotide

<400> SEQUENCE: 16
atgaaccaac tcagcttcct gctgtttctc atagcgacca ccagaggatg gagtacagat 60
caggaacacc ccagctgccc aggacccagg gaactggaag ccagcaaagt tgtcctcctg 120
cccagttgtc ccggagctcc aggaagtcct ggggagaagg gagccccagg tcctcaaggg 180
ccacctggac caccaggcaa gatgggcccc aagggtgagc caggcgaggc taatacttac 240
ttcaaggaat ggacctgttc ttcgtctcca tctctgccca gaagctgcaa ggaaatcaaa 300
gacgaatgtc ctagtgcatt tgatggcctg tattttctcc gcactgagaa tggtgttatc 360
taccagacct tctgtgacat gacctctggg ggtggcggct ggaccctggt ggccagcgtg 420
cacgagaatg acatgcgtgg gaagtgcacg gtgggcgatc gctggtccag tcagcagggc 480
agcaaagcag tctacccaga gggggacggc aactgggcca actacaacac ctttggatct 540
gcagaggcgg ccacgagcga tgactacaag aaccctggct actacgacat ccaggccaag 600
gacctgggca tctggcacgt gcccaataag tcccccatgc agcactggag aaacagctcc 660
ctgctgaggt accgcacgga cactggcttc ctccagacac tgggacataa tctgtttggc 720
atctaccaga aatatccagt gaaatatgga gaaggaaagt gttggactga caacggcccg 780
gtgatccctg tggtctatga ttttggcgac gcccagaaaa cagcatctta ttactcaccc 840
tatggccagc gggaattcac tgcgggattt gttcagttca gggtatttaa taacgagaga 900
gcagccaacg ccttgtgtgc tggaatgagg gtcaccggat gtaacactga gcaccactgc 960
attggtggag gaggatactt tccagaggcc agtccccagc agtgtggaga tttttctggt 1020
tttgattgga gtggatatgg aactcatgtt ggttacagca gcagccgtga gataactgag 1080
gcagctgtgc ttctattcta tcgttga 1107

<210> SEQ ID NO 17
<211> LENGTH: 368
<212> TYPE: PRT
<213> ORGANISM: Artificial sequence
<220> FEATURE:
<223> OTHER INFORMATION: Synthetic polypeptide

<400> SEQUENCE: 17

Met Asn Gln Leu Ser Phe Leu Leu Phe Leu Ile Ala Thr Thr Arg Gly
1 5 10 15

Trp Ser Thr Asp Gln Glu His Pro Ser Cys Pro Gly Pro Arg Glu Leu
20 25 30

Glu Ala Ser Lys Val Val Leu Leu Pro Ser Cys Pro Gly Ala Pro Gly
35 40 45

Ser Pro Gly Glu Lys Gly Ala Pro Gly Pro Gln Gly Pro Pro Gly Pro
50 55 60

Pro Gly Lys Met Gly Pro Lys Gly Glu Pro Gly Glu Ala Asn Thr Tyr
65 70 75 80

-continued

```
Phe Lys Glu Trp Thr Cys Ser Ser Ser Pro Ser Leu Pro Arg Ser Cys
                85                  90                  95

Lys Glu Ile Lys Asp Glu Cys Pro Ser Ala Phe Asp Gly Leu Tyr Phe
            100                 105                 110

Leu Arg Thr Glu Asn Gly Val Ile Tyr Gln Thr Phe Cys Asp Met Thr
        115                 120                 125

Ser Gly Gly Gly Gly Trp Thr Leu Val Ala Ser Val His Glu Asn Asp
    130                 135                 140

Met Arg Gly Lys Cys Thr Val Gly Asp Arg Trp Ser Ser Gln Gln Gly
145                 150                 155                 160

Ser Lys Ala Val Tyr Pro Glu Gly Asp Gly Asn Trp Ala Asn Tyr Asn
                165                 170                 175

Thr Phe Gly Ser Ala Glu Ala Ala Thr Ser Asp Asp Tyr Lys Asn Pro
            180                 185                 190

Gly Tyr Tyr Asp Ile Gln Ala Lys Asp Leu Gly Ile Trp His Val Pro
        195                 200                 205

Asn Lys Ser Pro Met Gln His Trp Arg Asn Ser Ser Leu Leu Arg Tyr
    210                 215                 220

Arg Thr Asp Thr Gly Phe Leu Gln Thr Leu Gly His Asn Leu Phe Gly
225                 230                 235                 240

Ile Tyr Gln Lys Tyr Pro Val Lys Tyr Gly Glu Gly Lys Cys Trp Thr
                245                 250                 255

Asp Asn Gly Pro Val Ile Pro Val Val Tyr Asp Phe Gly Asp Ala Gln
            260                 265                 270

Lys Thr Ala Ser Tyr Tyr Ser Pro Tyr Gly Gln Arg Glu Phe Thr Ala
        275                 280                 285

Gly Phe Val Gln Phe Arg Val Phe Asn Asn Glu Arg Ala Ala Asn Ala
    290                 295                 300

Leu Cys Ala Gly Met Arg Val Thr Gly Cys Asn Thr Glu His His Cys
305                 310                 315                 320

Ile Gly Gly Gly Gly Tyr Phe Pro Glu Ala Ser Pro Gln Gln Cys Gly
                325                 330                 335

Asp Phe Ser Gly Phe Asp Trp Ser Gly Tyr Gly Thr His Val Gly Tyr
            340                 345                 350

Ser Ser Ser Arg Glu Ile Thr Glu Ala Ala Val Leu Leu Phe Tyr Arg
        355                 360                 365
```

<210> SEQ ID NO 18
<211> LENGTH: 1293
<212> TYPE: DNA
<213> ORGANISM: Artificial sequence
<220> FEATURE:
<223> OTHER INFORMATION: Synthetic oligonucleotide

<400> SEQUENCE: 18

```
atgaaccaac tcagcttcct gctgtttctc atagcgacca ccagaggatg gagtacagat      60

ctccaggcgg cagacacctg tccagaggtg aagatggtgg gcctggaggg ctctgacaag     120

ctcaccattc tccgaggctg tccggggctg cctggggccc ctgggcccaa gggagaggca     180

ggcaccaatg gaaagagagg agaacgtggc ccccctggac ctcctgggaa gttggggcct     240

ccaggaaatc cagggccttc tgggtcacca ggaccaaagg gccaaaaagg agaccctgga     300

aaaagtccgg atggtgatag tagcctggct gcctcagaaa gaaaagctct gcaaacagaa     360

atggcacgta tcaaaaagtg gctcaccttc tctctgggca aacaagttgg ggaggctaat     420
```

-continued

```
actttacttca aggaatggac ctgttcttcg tctccatctc tgcccagaag ctgcaaggaa    480

atcaaagacg aatgtcctag tgcatttgat ggcctgtatt ttctccgcac tgagaatggt    540

gttatctacc agaccttctg tgacatgacc tctgggggtg gcggctggac cctggtggcc    600

agcgtgcacg agaatgacat gcgtgggaag tgcacggtgg gcgatcgctg gtccagtcag    660

cagggcagca aagcagtcta cccagagggg gacggcaact gggccaacta caacaccttt    720

ggatctgcag aggcggccac gagcgatgac tacaagaacc ctggctacta cgacatccag    780

gccaaggacc tgggcatctg gcacgtgccc aataagtccc ccatgcagca ctggagaaac    840

agctccctgc tgaggtaccg cacggacact ggcttcctcc agacactggg acataatctg    900

tttggcatct accagaaata tccagtgaaa tatggagaag gaaagtgttg gactgacaac    960

ggcccggtga tccctgtggt ctatgatttt ggcgacgccc agaaaacagc atcttattac   1020

tcaccctatg gccagcggga attcactgcg ggatttgttc agttcagggt atttaataac   1080

gagagagcag ccaacgcctt gtgtgctgga atgagggtca ccggatgtaa cactgagcac   1140

cactgcattg gtggaggagg atactttcca gaggccagtc cccagcagtg tggagatttt   1200

tctggttttg attggagtgg atatggaact catgttggtt acagcagcag ccgtgagata   1260

actgaggcag ctgtgcttct attctatcgt tga                                1293


<210> SEQ ID NO 19
<211> LENGTH: 430
<212> TYPE: PRT
<213> ORGANISM: Artificial sequence
<220> FEATURE:
<223> OTHER INFORMATION: Synthetic polypeptide

<400> SEQUENCE: 19

Met Asn Gln Leu Ser Phe Leu Leu Phe Leu Ile Ala Thr Thr Arg Gly
1               5                   10                  15

Trp Ser Thr Asp Leu Gln Ala Ala Asp Thr Cys Pro Glu Val Lys Met
            20                  25                  30

Val Gly Leu Glu Gly Ser Asp Lys Leu Thr Ile Leu Arg Gly Cys Pro
        35                  40                  45

Gly Leu Pro Gly Ala Pro Gly Pro Lys Gly Glu Ala Gly Thr Asn Gly
    50                  55                  60

Lys Arg Gly Glu Arg Gly Pro Pro Gly Pro Pro Gly Lys Leu Gly Pro
65                  70                  75                  80

Pro Gly Asn Pro Gly Pro Ser Gly Ser Pro Gly Pro Lys Gly Gln Lys
                85                  90                  95

Gly Asp Pro Gly Lys Ser Pro Asp Gly Asp Ser Ser Leu Ala Ala Ser
            100                 105                 110

Glu Arg Lys Ala Leu Gln Thr Glu Met Ala Arg Ile Lys Lys Trp Leu
        115                 120                 125

Thr Phe Ser Leu Gly Lys Gln Val Gly Glu Ala Asn Thr Tyr Phe Lys
    130                 135                 140

Glu Trp Thr Cys Ser Ser Ser Pro Ser Leu Pro Arg Ser Cys Lys Glu
145                 150                 155                 160

Ile Lys Asp Glu Cys Pro Ser Ala Phe Asp Gly Leu Tyr Phe Leu Arg
                165                 170                 175

Thr Glu Asn Gly Val Ile Tyr Gln Thr Phe Cys Asp Met Thr Ser Gly
            180                 185                 190

Gly Gly Gly Trp Thr Leu Val Ala Ser Val His Glu Asn Asp Met Arg
        195                 200                 205
```

-continued

```
Gly Lys Cys Thr Val Gly Asp Arg Trp Ser Ser Gln Gln Gly Ser Lys
    210                 215                 220

Ala Val Tyr Pro Glu Gly Asp Gly Asn Trp Ala Asn Tyr Asn Thr Phe
225                 230                 235                 240

Gly Ser Ala Glu Ala Ala Thr Ser Asp Asp Tyr Lys Asn Pro Gly Tyr
                245                 250                 255

Tyr Asp Ile Gln Ala Lys Asp Leu Gly Ile Trp His Val Pro Asn Lys
            260                 265                 270

Ser Pro Met Gln His Trp Arg Asn Ser Ser Leu Leu Arg Tyr Arg Thr
        275                 280                 285

Asp Thr Gly Phe Leu Gln Thr Leu Gly His Asn Leu Phe Gly Ile Tyr
    290                 295                 300

Gln Lys Tyr Pro Val Lys Tyr Gly Glu Gly Lys Cys Trp Thr Asp Asn
305                 310                 315                 320

Gly Pro Val Ile Pro Val Val Tyr Asp Phe Gly Asp Ala Gln Lys Thr
                325                 330                 335

Ala Ser Tyr Tyr Ser Pro Tyr Gly Gln Arg Glu Phe Thr Ala Gly Phe
            340                 345                 350

Val Gln Phe Arg Val Phe Asn Asn Glu Arg Ala Ala Asn Ala Leu Cys
        355                 360                 365

Ala Gly Met Arg Val Thr Gly Cys Asn Thr Glu His His Cys Ile Gly
    370                 375                 380

Gly Gly Gly Tyr Phe Pro Glu Ala Ser Pro Gln Gln Cys Gly Asp Phe
385                 390                 395                 400

Ser Gly Phe Asp Trp Ser Gly Tyr Gly Thr His Val Gly Tyr Ser Ser
                405                 410                 415

Ser Arg Glu Ile Thr Glu Ala Ala Val Leu Leu Phe Tyr Arg
            420                 425                 430
```

```
<210> SEQ ID NO 20
<211> LENGTH: 1146
<212> TYPE: DNA
<213> ORGANISM: Artificial sequence
<220> FEATURE:
<223> OTHER INFORMATION: Synthetic oligonucleotide

<400> SEQUENCE: 20

atgaaccaac tcagcttcct gctgtttctc atagcgacca ccagaggatg gagtacagat      60

ctccaggcgg cagacacctg tccagaggtg aagatggtgg gcctggaggg ctctgacaag     120

ctcaccattc tccgaggctg tccggggctg cctggggccc ctgggcccaa gggagaggca     180

ggcaccaatg gaaagagagg agaacgtggc ccccctggac ctcctgggaa ggcaggacca     240

cctgggccca acggagcacc tggggaggct aatacttact tcaaggaatg gacctgttct     300

tcgtctccat ctctgcccag aagctgcaag gaaatcaaag acgaatgtcc tagtgcattt     360

gatggcctgt attttctccg cactgagaat ggtgttatct accagacctt ctgtgacatg     420

acctctgggg gtggcggctg gaccctggtg gccagcgtgc acgagaatga catgcgtggg     480

aagtgcacgg tgggcgatcg ctggtccagt cagcagggca gcaaagcagt ctacccagag     540

ggggacggca actgggccaa ctacaacacc tttggatctg cagaggcggc cacgagcgat     600

gactacaaga accctggcta ctacgacatc caggccaagg acctgggcat ctggcacgtg     660

cccaataagt cccccatgca gcactggaga aacagctccc tgctgaggta ccgcacggac     720

actggcttcc tccagacact gggacataat ctgtttggca tctaccagaa atatccagtg     780

aaatatggag aaggaaagtg ttggactgac aacggcccgg tgatccctgt ggtctatgat     840
```

```
tttggcgacg cccagaaaac agcatcttat tactcaccct atggccagcg ggaattcact    900

gcgggatttg ttcagttcag ggtatttaat aacgagagag cagccaacgc cttgtgtgct    960

ggaatgaggg tcaccggatg taacactgag caccactgca ttggtggagg aggatacttt   1020

ccagaggcca gtccccagca gtgtggagat ttttctggtt ttgattggag tggatatgga   1080

actcatgttg gttacagcag cagccgtgag ataactgagg cagctgtgct tctattctat   1140

cgttga                                                              1146


<210> SEQ ID NO 21
<211> LENGTH: 381
<212> TYPE: PRT
<213> ORGANISM: Artificial sequence
<220> FEATURE:
<223> OTHER INFORMATION: Synthetic polypeptide

<400> SEQUENCE: 21

Met Asn Gln Leu Ser Phe Leu Leu Phe Leu Ile Ala Thr Thr Arg Gly
1               5                   10                  15

Trp Ser Thr Asp Leu Gln Ala Ala Asp Thr Cys Pro Glu Val Lys Met
            20                  25                  30

Val Gly Leu Glu Gly Ser Asp Lys Leu Thr Ile Leu Arg Gly Cys Pro
        35                  40                  45

Gly Leu Pro Gly Ala Pro Gly Pro Lys Gly Glu Ala Gly Thr Asn Gly
    50                  55                  60

Lys Arg Gly Glu Arg Gly Pro Pro Gly Pro Pro Gly Lys Ala Gly Pro
65                  70                  75                  80

Pro Gly Pro Asn Gly Ala Pro Gly Glu Ala Asn Thr Tyr Phe Lys Glu
                85                  90                  95

Trp Thr Cys Ser Ser Ser Pro Ser Leu Pro Arg Ser Cys Lys Glu Ile
            100                 105                 110

Lys Asp Glu Cys Pro Ser Ala Phe Asp Gly Leu Tyr Phe Leu Arg Thr
        115                 120                 125

Glu Asn Gly Val Ile Tyr Gln Thr Phe Cys Asp Met Thr Ser Gly Gly
    130                 135                 140

Gly Gly Trp Thr Leu Val Ala Ser Val His Glu Asn Asp Met Arg Gly
145                 150                 155                 160

Lys Cys Thr Val Gly Asp Arg Trp Ser Ser Gln Gln Gly Ser Lys Ala
                165                 170                 175

Val Tyr Pro Glu Gly Asp Gly Asn Trp Ala Asn Tyr Asn Thr Phe Gly
            180                 185                 190

Ser Ala Glu Ala Ala Thr Ser Asp Asp Tyr Lys Asn Pro Gly Tyr Tyr
        195                 200                 205

Asp Ile Gln Ala Lys Asp Leu Gly Ile Trp His Val Pro Asn Lys Ser
    210                 215                 220

Pro Met Gln His Trp Arg Asn Ser Ser Leu Leu Arg Tyr Arg Thr Asp
225                 230                 235                 240

Thr Gly Phe Leu Gln Thr Leu Gly His Asn Leu Phe Gly Ile Tyr Gln
                245                 250                 255

Lys Tyr Pro Val Lys Tyr Gly Glu Gly Lys Cys Trp Thr Asp Asn Gly
            260                 265                 270

Pro Val Ile Pro Val Val Tyr Asp Phe Gly Asp Ala Gln Lys Thr Ala
        275                 280                 285

Ser Tyr Tyr Ser Pro Tyr Gly Gln Arg Glu Phe Thr Ala Gly Phe Val
    290                 295                 300
```

-continued

```
Gln Phe Arg Val Phe Asn Asn Glu Arg Ala Ala Asn Ala Leu Cys Ala
305                 310                 315                 320

Gly Met Arg Val Thr Gly Cys Asn Thr Glu His His Cys Ile Gly Gly
                325                 330                 335

Gly Gly Tyr Phe Pro Glu Ala Ser Pro Gln Gln Cys Gly Asp Phe Ser
            340                 345                 350

Gly Phe Asp Trp Ser Gly Tyr Gly Thr His Val Gly Tyr Ser Ser Ser
        355                 360                 365

Arg Glu Ile Thr Glu Ala Ala Val Leu Leu Phe Tyr Arg
    370                 375                 380
```

<210> SEQ ID NO 22
<211> LENGTH: 1275
<212> TYPE: DNA
<213> ORGANISM: Artificial sequence
<220> FEATURE:
<223> OTHER INFORMATION: Synthetic oligonucleotide

<400> SEQUENCE: 22

```
atgaaccaac tcagcttcct gctgtttctc atagcgacca ccagaggatg gagtacagat     60

actgtgacct gtgaggatgc ccaaaagacc tgccctgcag tgattgcctg tagctctcca    120

ggcatcaacg gcttcccagg caaagatggg cgtgatggca ccaagggaga aaagggggaa    180

ccaggccaag ggctcagagg cttacagggc ccccctggaa agttggggcc tccaggaaat    240

ccagggcctt ctgggtcacc aggaccaaag ggccaaaaag gagaccctgg aaaaagtccg    300

gatggtgata gtagcctggc tgcctcagaa agaaaagctc tgcaaacaga aatggcacgt    360

atcaaaaagt ggctcacctt ctctctgggc aaagaggcta atacttactt caaggaatgg    420

acctgttctt cgtctccatc tctgcccaga agctgcaagg aaatcaaaga cgaatgtcct    480

agtgcatttg atggcctgta ttttctccgc actgagaatg gtgttatcta ccagaccttc    540

tgtgacatga cctctggggg tggcggctgg accctggtgg ccagcgtgca cgagaatgac    600

atgcgtggga agtgcacggt gggcgatcgc tggtccagtc agcagggcag caaagcagtc    660

tacccagagg gggacggcaa ctgggccaac tacaacacct ttggatctgc agaggcggcc    720

acgagcgatg actacaagaa ccctggctac tacgacatcc aggccaagga cctgggcatc    780

tggcacgtgc ccaataagtc ccccatgcag cactggagaa acagctccct gctgaggtac    840

cgcacggaca ctggcttcct ccagacactg ggacataatc tgtttggcat ctaccagaaa    900

tatccagtga aatatggaga aggaaagtgt tggactgaca acggcccggt gatccctgtg    960

gtctatgatt ttggcgacgc ccagaaaaca gcatcttatt actcacccta tggccagcgg   1020

gaattcactg cgggatttgt tcagttcagg gtatttaata acgagagagc agccaacgcc   1080

ttgtgtgctg gaatgagggt caccggatgt aacactgagc accactgcat tggtggagga   1140

ggatactttc cagaggccag tccccagcag tgtggagatt tttctggttt tgattggagt   1200

ggatatggaa ctcatgttgg ttacagcagc agccgtgaga taactgaggc agctgtgctt   1260

ctattctatc gttga                                                    1275
```

<210> SEQ ID NO 23
<211> LENGTH: 424
<212> TYPE: PRT
<213> ORGANISM: Artificial sequence
<220> FEATURE:
<223> OTHER INFORMATION: Synthetic polypeptide

<400> SEQUENCE: 23

-continued

```
Met Asn Gln Leu Ser Phe Leu Leu Phe Leu Ile Ala Thr Thr Arg Gly
1               5                   10                  15

Trp Ser Thr Asp Thr Val Thr Cys Glu Asp Ala Gln Lys Thr Cys Pro
            20                  25                  30

Ala Val Ile Ala Cys Ser Ser Pro Gly Ile Asn Gly Phe Pro Gly Lys
        35                  40                  45

Asp Gly Arg Asp Gly Thr Lys Gly Glu Lys Gly Glu Pro Gly Gln Gly
    50                  55                  60

Leu Arg Gly Leu Gln Gly Pro Pro Gly Lys Leu Gly Pro Pro Gly Asn
65                  70                  75                  80

Pro Gly Pro Ser Gly Ser Pro Gly Pro Lys Gly Gln Lys Gly Asp Pro
                85                  90                  95

Gly Lys Ser Pro Asp Gly Asp Ser Ser Leu Ala Ala Ser Glu Arg Lys
            100                 105                 110

Ala Leu Gln Thr Glu Met Ala Arg Ile Lys Lys Trp Leu Thr Phe Ser
        115                 120                 125

Leu Gly Lys Glu Ala Asn Thr Tyr Phe Lys Glu Trp Thr Cys Ser Ser
    130                 135                 140

Ser Pro Ser Leu Pro Arg Ser Cys Lys Glu Ile Lys Asp Glu Cys Pro
145                 150                 155                 160

Ser Ala Phe Asp Gly Leu Tyr Phe Leu Arg Thr Glu Asn Gly Val Ile
                165                 170                 175

Tyr Gln Thr Phe Cys Asp Met Thr Ser Gly Gly Gly Gly Trp Thr Leu
            180                 185                 190

Val Ala Ser Val His Glu Asn Asp Met Arg Gly Lys Cys Thr Val Gly
        195                 200                 205

Asp Arg Trp Ser Ser Gln Gln Gly Ser Lys Ala Val Tyr Pro Glu Gly
    210                 215                 220

Asp Gly Asn Trp Ala Asn Tyr Asn Thr Phe Gly Ser Ala Glu Ala Ala
225                 230                 235                 240

Thr Ser Asp Asp Tyr Lys Asn Pro Gly Tyr Tyr Asp Ile Gln Ala Lys
                245                 250                 255

Asp Leu Gly Ile Trp His Val Pro Asn Lys Ser Pro Met Gln His Trp
            260                 265                 270

Arg Asn Ser Ser Leu Leu Arg Tyr Arg Thr Asp Thr Gly Phe Leu Gln
        275                 280                 285

Thr Leu Gly His Asn Leu Phe Gly Ile Tyr Gln Lys Tyr Pro Val Lys
    290                 295                 300

Tyr Gly Glu Gly Lys Cys Trp Thr Asp Asn Gly Pro Val Ile Pro Val
305                 310                 315                 320

Val Tyr Asp Phe Gly Asp Ala Gln Lys Thr Ala Ser Tyr Tyr Ser Pro
                325                 330                 335

Tyr Gly Gln Arg Glu Phe Thr Ala Gly Phe Val Gln Phe Arg Val Phe
            340                 345                 350

Asn Asn Glu Arg Ala Ala Asn Ala Leu Cys Ala Gly Met Arg Val Thr
        355                 360                 365

Gly Cys Asn Thr Glu His His Cys Ile Gly Gly Gly Gly Tyr Phe Pro
    370                 375                 380

Glu Ala Ser Pro Gln Gln Cys Gly Asp Phe Ser Gly Phe Asp Trp Ser
385                 390                 395                 400

Gly Tyr Gly Thr His Val Gly Tyr Ser Ser Ser Arg Glu Ile Thr Glu
                405                 410                 415
```

Ala Ala Val Leu Leu Phe Tyr Arg
420

<210> SEQ ID NO 24
<211> LENGTH: 1284
<212> TYPE: DNA
<213> ORGANISM: Artificial sequence
<220> FEATURE:
<223> OTHER INFORMATION: Synthetic oligonucleotide

<400> SEQUENCE: 24
atgaaccaac tcagcttcct gctgtttctc atagcgacca ccagaggatg gagtacagat 60
actgtgacct gtgaggatgc ccaaaagacc tgccctgcag tgattgcctg tagctctcca 120
ggcatcaacg gcttcccagg caaagatggg cgtgatggca ccaagggaga aaagggggaa 180
ccaggccaag ggctcagagg cttacagggc ccccctggaa agttggggcc tccaggaaat 240
ccagggcctt ctgggtcacc aggaccaaag ggccaaaaag gagaccctgg aaaaagtccg 300
gatggtgata gtagcctggc tgcctcagaa agaaaagctc tgcaaacaga aatggcacgt 360
atcaaaaagt ggctcacctt ctctctgggc aaacaagttg ggaggctaa tacttacttc 420 aaggaatgga cctgttcttc gtctccatct ctgcccagaa gctgcaagga aatcaaagac 480
gaatgtccta gtgcatttga tggcctgtat tttctccgca ctgagaatgg tgttatctac 540
cagaccttct gtgacatgac ctctgggggt ggcggctgga ccctggtggc cagcgtgcac 600
gagaatgaca tgcgtgggaa gtgcacggtg ggcgatcgct ggtccagtca gcagggcagc 660
aaagcagtct acccagaggg ggacggcaac tgggccaact acaacacctt tggatctgca 720
gaggcggcca cgagcgatga ctacaagaac cctggctact acgacatcca ggccaaggac 780
ctgggcatct ggcacgtgcc caataagtcc ccatgcagc actggagaaa cagctccctg 840
ctgaggtacc gcacggacac tggcttcctc cagacactgg gacataatct gtttggcatc 900
taccagaaat atccagtgaa atatggagaa ggaaagtgtt ggactgacaa cggcccggtg 960
atccctgtgg tctatgattt tggcgacgcc cagaaaacag catcttatta ctcaccctat 1020
ggccagcggg aattcactgc gggatttgtt cagttcaggg tatttaataa cgagagagca 1080
gccaacgcct tgtgtgctgg aatgagggtc accggatgta acactgagca ccactgcatt 1140
ggtggaggag gatactttcc agaggccagt ccccagcagt gtggagattt ttctggtttt 1200
gattggagtg gatatggaac tcatgttggt tacagcagca gccgtgagat aactgaggca 1260
gctgtgcttc tattctatcg ttga 1284

<210> SEQ ID NO 25
<211> LENGTH: 427
<212> TYPE: PRT
<213> ORGANISM: Artificial sequence
<220> FEATURE:
<223> OTHER INFORMATION: Synthetic polypeptide

<400> SEQUENCE: 25

Met Asn Gln Leu Ser Phe Leu Leu Phe Leu Ile Ala Thr Thr Arg Gly
1 5 10 15

Trp Ser Thr Asp Thr Val Thr Cys Glu Asp Ala Gln Lys Thr Cys Pro
20 25 30

Ala Val Ile Ala Cys Ser Ser Pro Gly Ile Asn Gly Phe Pro Gly Lys
35 40 45

Asp Gly Arg Asp Gly Thr Lys Gly Glu Lys Gly Glu Pro Gly Gln Gly
50 55 60

```
Leu Arg Gly Leu Gln Gly Pro Pro Gly Lys Leu Gly Pro Pro Gly Asn
65                  70                  75                  80

Pro Gly Pro Ser Gly Ser Pro Gly Pro Lys Gly Gln Lys Gly Asp Pro
                85                  90                  95

Gly Lys Ser Pro Asp Gly Asp Ser Ser Leu Ala Ala Ser Glu Arg Lys
            100                 105                 110

Ala Leu Gln Thr Glu Met Ala Arg Ile Lys Lys Trp Leu Thr Phe Ser
        115                 120                 125

Leu Gly Lys Gln Val Gly Glu Ala Asn Thr Tyr Phe Lys Glu Trp Thr
    130                 135                 140

Cys Ser Ser Ser Pro Ser Leu Pro Arg Ser Cys Lys Glu Ile Lys Asp
145                 150                 155                 160

Glu Cys Pro Ser Ala Phe Asp Gly Leu Tyr Phe Leu Arg Thr Glu Asn
                165                 170                 175

Gly Val Ile Tyr Gln Thr Phe Cys Asp Met Thr Ser Gly Gly Gly Gly
            180                 185                 190

Trp Thr Leu Val Ala Ser Val His Glu Asn Asp Met Arg Gly Lys Cys
        195                 200                 205

Thr Val Gly Asp Arg Trp Ser Ser Gln Gln Gly Ser Lys Ala Val Tyr
    210                 215                 220

Pro Glu Gly Asp Gly Asn Trp Ala Asn Tyr Asn Thr Phe Gly Ser Ala
225                 230                 235                 240

Glu Ala Ala Thr Ser Asp Asp Tyr Lys Asn Pro Gly Tyr Tyr Asp Ile
                245                 250                 255

Gln Ala Lys Asp Leu Gly Ile Trp His Val Pro Asn Lys Ser Pro Met
            260                 265                 270

Gln His Trp Arg Asn Ser Ser Leu Leu Arg Tyr Arg Thr Asp Thr Gly
        275                 280                 285

Phe Leu Gln Thr Leu Gly His Asn Leu Phe Gly Ile Tyr Gln Lys Tyr
    290                 295                 300

Pro Val Lys Tyr Gly Glu Gly Lys Cys Trp Thr Asp Asn Gly Pro Val
305                 310                 315                 320

Ile Pro Val Val Tyr Asp Phe Gly Asp Ala Gln Lys Thr Ala Ser Tyr
                325                 330                 335

Tyr Ser Pro Tyr Gly Gln Arg Glu Phe Thr Ala Gly Phe Val Gln Phe
            340                 345                 350

Arg Val Phe Asn Asn Glu Arg Ala Ala Asn Ala Leu Cys Ala Gly Met
        355                 360                 365

Arg Val Thr Gly Cys Asn Thr Glu His His Cys Ile Gly Gly Gly Gly
    370                 375                 380

Tyr Phe Pro Glu Ala Ser Pro Gln Gln Cys Gly Asp Phe Ser Gly Phe
385                 390                 395                 400

Asp Trp Ser Gly Tyr Gly Thr His Val Gly Tyr Ser Ser Ser Arg Glu
                405                 410                 415

Ile Thr Glu Ala Ala Val Leu Leu Phe Tyr Arg
            420                 425
```

<210> SEQ ID NO 26
<211> LENGTH: 1137
<212> TYPE: DNA
<213> ORGANISM: Artificial sequence
<220> FEATURE:
<223> OTHER INFORMATION: Synthetic oligonucleotide

<400> SEQUENCE: 26

```
atgaaccaac tcagcttcct gctgtttctc atagcgacca ccagaggatg gagtacagat      60

gcggacacat gtccagaggt gaaggtggtg ggcctggagg gctctgacaa gctcaccatt     120

ctccgaggct gcccggggct gcccggggcc ccagggccaa agggagaggc aggtgtcatt     180

ggagagagag gagaacgcgg tctccctgga gcccctggaa aggcaggacc agtggggccc     240

aaaggagacc gaggagaggc taatacttac ttcaaggaat ggacctgttc ttcgtctcca     300

tctctgccca gaagctgcaa ggaaatcaaa gacgaatgtc ctagtgcatt tgatggcctg     360

tattttctcc gcactgagaa tggtgttatc taccagacct tctgtgacat gacctctggg     420

ggtggcggct ggaccctggt ggccagcgtg cacgagaatg acatgcgtgg gaagtgcacg     480

gtgggcgatc gctggtccag tcagcagggc agcaaagcag tctacccaga gggggacggc     540

aactgggcca actacaacac ctttggatct gcagaggcgg ccacgagcga tgactacaag     600

aaccctggct actacgacat ccaggccaag gacctgggca tctggcacgt gcccaataag     660

tcccccatgc agcactggag aaacagctcc ctgctgaggt accgcacgga cactggcttc     720

ctccagacac tgggacataa tctgtttggc atctaccaga aatatccagt gaaatatgga     780

gaaggaaagt gttggactga caacggcccg gtgatccctg tggtctatga ttttggcgac     840

gcccagaaaa cagcatctta ttactcaccc tatggccagc gggaattcac tgcgggattt     900

gttcagttca gggtatttaa taacgagaga gcagccaacg ccttgtgtgc tggaatgagg     960

gtcaccggat gtaacactga gcaccactgc attggtggag gaggatactt tccagaggcc    1020

agtccccagc agtgtggaga tttttctggt tttgattgga gtggatatgg aactcatgtt    1080

ggttacagca gcagccgtga gataactgag gcagctgtgc ttctattcta tcgttga       1137


<210> SEQ ID NO 27
<211> LENGTH: 378
<212> TYPE: PRT
<213> ORGANISM: Artificial sequence
<220> FEATURE:
<223> OTHER INFORMATION: Synthetic polypeptide

<400> SEQUENCE: 27

Met Asn Gln Leu Ser Phe Leu Leu Phe Leu Ile Ala Thr Thr Arg Gly
1               5                   10                  15

Trp Ser Thr Asp Ala Asp Thr Cys Pro Glu Val Lys Val Val Gly Leu
            20                  25                  30

Glu Gly Ser Asp Lys Leu Thr Ile Leu Arg Gly Cys Pro Gly Leu Pro
        35                  40                  45

Gly Ala Pro Gly Pro Lys Gly Glu Ala Gly Val Ile Gly Glu Arg Gly
    50                  55                  60

Glu Arg Gly Leu Pro Gly Ala Pro Gly Lys Ala Gly Pro Val Gly Pro
65                  70                  75                  80

Lys Gly Asp Arg Gly Glu Ala Asn Thr Tyr Phe Lys Glu Trp Thr Cys
                85                  90                  95

Ser Ser Ser Pro Ser Leu Pro Arg Ser Cys Lys Glu Ile Lys Asp Glu
            100                 105                 110

Cys Pro Ser Ala Phe Asp Gly Leu Tyr Phe Leu Arg Thr Glu Asn Gly
        115                 120                 125

Val Ile Tyr Gln Thr Phe Cys Asp Met Thr Ser Gly Gly Gly Gly Trp
    130                 135                 140

Thr Leu Val Ala Ser Val His Glu Asn Asp Met Arg Gly Lys Cys Thr
145                 150                 155                 160

Val Gly Asp Arg Trp Ser Ser Gln Gln Gly Ser Lys Ala Val Tyr Pro
```

```
                165                 170                 175

Glu Gly Asp Gly Asn Trp Ala Asn Tyr Asn Thr Phe Gly Ser Ala Glu
            180                 185                 190

Ala Ala Thr Ser Asp Asp Tyr Lys Asn Pro Gly Tyr Tyr Asp Ile Gln
        195                 200                 205

Ala Lys Asp Leu Gly Ile Trp His Val Pro Asn Lys Ser Pro Met Gln
    210                 215                 220

His Trp Arg Asn Ser Ser Leu Leu Arg Tyr Arg Thr Asp Thr Gly Phe
225                 230                 235                 240

Leu Gln Thr Leu Gly His Asn Leu Phe Gly Ile Tyr Gln Lys Tyr Pro
                245                 250                 255

Val Lys Tyr Gly Glu Gly Lys Cys Trp Thr Asp Asn Gly Pro Val Ile
            260                 265                 270

Pro Val Val Tyr Asp Phe Gly Asp Ala Gln Lys Thr Ala Ser Tyr Tyr
        275                 280                 285

Ser Pro Tyr Gly Gln Arg Glu Phe Thr Ala Gly Phe Val Gln Phe Arg
    290                 295                 300

Val Phe Asn Asn Glu Arg Ala Ala Asn Ala Leu Cys Ala Gly Met Arg
305                 310                 315                 320

Val Thr Gly Cys Asn Thr Glu His His Cys Ile Gly Gly Gly Gly Tyr
                325                 330                 335

Phe Pro Glu Ala Ser Pro Gln Gln Cys Gly Asp Phe Ser Gly Phe Asp
            340                 345                 350

Trp Ser Gly Tyr Gly Thr His Val Gly Tyr Ser Ser Ser Arg Glu Ile
        355                 360                 365

Thr Glu Ala Ala Val Leu Leu Phe Tyr Arg
    370                 375
```

<210> SEQ ID NO 28
<211> LENGTH: 942
<212> TYPE: DNA
<213> ORGANISM: Homo sapiens

<400> SEQUENCE: 28

```
atgaaccaac tcagcttcct gctgtttctc atagcgacca ccagaggatg gagtacagat     60

gaggctaata cttacttcaa ggaatggacc atgaaccaac tcagcttcct gctgtttctc    120

atagcgacca ccagaggatg gagtacagat gaggctaata cttacttcaa ggaatggacc    180

gagaatggtg ttatctacca gaccttctgt gacatgacct ctgggggtgg cggctggacc    240

ctggtggcca gcgtgcacga gaatgacatg cgtgggaagt gcacggtggg cgatcgctgg    300

tccagtcagc agggcagcaa agcagactac ccagaggggg acggcaactg ggccaactac    360

aacacctttg gatctgcaga ggcggccacg agcgatgact acaagaaccc tggctactac    420

gacatccagg ccaaggacct gggcatctgg cacgtgccca ataagtcccc catgcagcac    480

tggagaaaca gctccctgct gaggtaccgc acggacactg gcttcctcca gacactggga    540

cataatctgt ttggcatcta ccagaaatat ccagtgaaat atggagaagg aaagtgttgg    600

actgacaacg gcccggtgat ccctgtggtc tatgattttg gcgacgccca gaaaacagca    660

tcttattact caccctatgg ccagcgggaa ttcactgcgg gatttgttca gttcagggta    720

tttaataacg agagagcagc caacgccttg tgtgctggaa tgagggtcac cggatgtaac    780

actgagcacc actgcattgg tggaggagga tactttccag aggccagtcc ccagcagtgt    840

ggagattttt ctggttttga ttggagtgga tatggaactc atgttggtta cagcagcagc    900
```

```
cgtgagataa ctgaggcagc tgtgcttcta ttctatcgtt ga                    942


<210> SEQ ID NO 29
<211> LENGTH: 1114
<212> TYPE: DNA
<213> ORGANISM: Homo sapiens

<400> SEQUENCE: 29

gcaggggagc tccgagtgtc cacaggaagg gaactatcag ctcctggcat ctgtaaggat     60

gctgtccatg ctgaggacaa tgaccagact ctgcttcctg ttattcttct ctgtggccac    120

cagtgggtgc agtgcagcag cagcctcttc tcttgagatg ctctcgaggg aattcgaaac    180

ctgtgccttc tccttttctt ccctgcctag aagctgcaaa gaaatcaagg aacgctgcca    240

tagtgcaggt gatggcctgt attttctccg caccaagaat ggtgttgtct accagacctt    300

ctgtgacatg acttctgggg gtggcggctg gaccctggtg gccagcgtgc acgagaatga    360

catgcgtggg aagtgcacgg tgggtgatcg ctggtccagt cagcagggca acaaagcaga    420

ctacccagag gggatggca actgggccaa ctacaacacc tttggatctg cagaggcggc    480

cacgagcgat gactacaaga accctggcta ctacgacatc caggccaagg acctgggcat    540

ctggcatgtg cccaacaagt cccccatgca gcattggaga aacagcgccc tgctgaggta    600

ccgcaccaac actggcttcc tccagagact gggacataat ctgtttggca tctaccagaa    660

atacccagtg aaatacagat cagggaaatg ttggaatgac aatggcccag ccatacctgt    720

ggtctatgac tttggtgatg ctaagaagac tgcatcttat tactcaccgt atggtcaacg    780

ggaatttgtt gcaggattcg ttcagttccg ggtgtttaat aacgagagag cagccaacgc    840

cctttgtgct gggataaaag ttactggctg taacactgag catcactgca tcggtggagg    900

agggttcttc ccacagggca aaccccgtca gtgtggggac ttctccgcct ttgactggga    960

tggatatgga actcacgtta agagcagctg cagtcgggag ataacggagg cggctgtact   1020

cttgttctat agatgagaca gagctctgcg gtgtcagggc gagaacccat cttccaaccc   1080

cggctatttg gagacggaaa aactggaatt ctaa                               1114


<210> SEQ ID NO 30
<211> LENGTH: 369
<212> TYPE: PRT
<213> ORGANISM: Homo sapiens

<400> SEQUENCE: 30

Gln Gly Ser Ser Glu Cys Pro Gln Glu Gly Asn Tyr Gln Leu Leu Ala
1               5                   10                  15

Ser Val Arg Met Leu Ser Met Leu Arg Thr Met Thr Arg Leu Cys Phe
            20                  25                  30

Leu Leu Phe Phe Ser Val Ala Thr Ser Gly Cys Ser Ala Ala Ala Ala
        35                  40                  45

Ser Ser Leu Glu Met Leu Ser Arg Glu Phe Glu Thr Cys Ala Phe Ser
    50                  55                  60

Phe Ser Ser Leu Pro Arg Ser Cys Lys Glu Ile Lys Glu Arg Cys His
65                  70                  75                  80

Ser Ala Gly Asp Gly Leu Tyr Phe Leu Arg Thr Lys Asn Gly Val Val
                85                  90                  95

Tyr Gln Thr Phe Cys Asp Met Thr Ser Gly Gly Gly Gly Trp Thr Leu
            100                 105                 110

Val Ala Ser Val His Glu Asn Asp Met Arg Gly Lys Cys Thr Val Gly
        115                 120                 125
```

```
Asp Arg Trp Ser Ser Gln Gln Gly Asn Lys Ala Asp Tyr Pro Glu Gly
    130                 135                 140

Asp Gly Asn Trp Ala Asn Tyr Asn Thr Phe Gly Ser Ala Glu Ala Ala
145                 150                 155                 160

Thr Ser Asp Asp Tyr Lys Asn Pro Gly Tyr Tyr Asp Ile Gln Ala Lys
                165                 170                 175

Asp Leu Gly Ile Trp His Val Pro Asn Lys Ser Pro Met Gln His Trp
            180                 185                 190

Arg Asn Ser Ala Leu Leu Arg Tyr Arg Thr Asn Thr Gly Phe Leu Gln
        195                 200                 205

Arg Leu Gly His Asn Leu Phe Gly Ile Tyr Gln Lys Tyr Pro Val Lys
    210                 215                 220

Tyr Arg Ser Gly Lys Cys Trp Asn Asp Asn Gly Pro Ala Ile Pro Val
225                 230                 235                 240

Val Tyr Asp Phe Gly Asp Ala Lys Lys Thr Ala Ser Tyr Tyr Ser Pro
                245                 250                 255

Tyr Gly Gln Arg Glu Phe Val Ala Gly Phe Val Gln Phe Arg Val Phe
            260                 265                 270

Asn Asn Glu Arg Ala Ala Asn Ala Leu Cys Ala Gly Ile Lys Val Thr
        275                 280                 285

Gly Cys Asn Thr Glu His His Cys Ile Gly Gly Gly Gly Phe Phe Pro
    290                 295                 300

Gln Gly Lys Pro Arg Gln Cys Gly Asp Phe Ser Ala Phe Asp Trp Asp
305                 310                 315                 320

Gly Tyr Gly Thr His Val Lys Ser Ser Cys Ser Arg Glu Ile Thr Glu
                325                 330                 335

Ala Ala Val Leu Leu Phe Tyr Arg Asp Arg Ala Leu Arg Cys Gln Gly
            340                 345                 350

Glu Asn Pro Ser Ser Asn Pro Gly Tyr Leu Glu Thr Glu Lys Leu Glu
        355                 360                 365

Phe
```

<210> SEQ ID NO 31
<211> LENGTH: 1149
<212> TYPE: DNA
<213> ORGANISM: Mus musculus

<400> SEQUENCE: 31

```
ggagcctcag cagagaaagg ttcctgtcat tactcagcta gcaactctca gctcctgcct      60

ggtgcagagg gaagaccacc atgacccaac tgggattcct gctgtttatc atggtggcta     120

ccagaggttg cagtgcagct gaagagaacc tggacaccaa caggtggggc aattctttct     180

tttcctctct gcccagaagc tgcaaggaaa tcaagcagga gcacacaaag gcacaagatg     240

gtctctattt cctgcgcacg aagaatggtg tcatctacca gaccttctgt gacatgacca     300

ctgcaggtgg tggctggacc ctggtggcta gtgtgcatga gaacaacatg cgtgggaagt     360

gcactgtggg tgatcgatgg tccagtcagc aaggcaacag agctgactac ccagaggggg     420

atggcaactg ggccaactac aacacctttg ggtctgcaga ggctgccaca agtgatgact     480

acaagaaccc tggctacttt gacatccagg ctgagaacct gggcatctgg catgtgccca     540

acaaaagccc cctgcacaac tggaggaaga gctccctgct gaggtaccgc accttcactg     600

gcttcctgca gcacttggga cataatctgt ttggcctcta caagaagtac ccggtgaaat     660

acggagaagg aaagtgttgg actgacaatg gtccagcatt acctgtagtc tatgactttg     720
```

```
gtgatgctcg gaagacagcc tcttattact ccccctctgg ccagagggaa tttactgcag    780

gatatgttca gttcagagtg tttaataatg agagagcggc cagtgccttg tgtgctggcg    840

tgagggtcac tggatgtaat actgaacatc actgcatcgg tggaggagga ttcttcccag    900

aaggtaaccc cgtgcagtgt ggagactttg cttcatttga ttgggatgga tatggaactc    960

acaatgggta cagcagtagc cggaagataa ctgaagcagc cgtgcttctg ttttatcgct   1020

gagaactctg cgggattggc cctgacttct ccattgtggg ctccaaggca tgagaaacac   1080

tgacttagta actggaatgc taatgagcaa taaagcagga taaatcatgt tccttgcaaa   1140

aaaaaaaaa                                                           1149


<210> SEQ ID NO 32
<211> LENGTH: 376
<212> TYPE: PRT
<213> ORGANISM: Mus musculus

<400> SEQUENCE: 32

Arg Ser Leu Ser Arg Glu Arg Phe Leu Pro Leu Leu Ser Gln Leu Ser
1               5                   10                  15

Ala Pro Ala Trp Cys Arg Gly Lys Thr Thr Met Thr Gln Leu Gly Phe
            20                  25                  30

Leu Leu Phe Ile Met Val Ala Thr Arg Gly Cys Ser Ala Ala Glu Glu
        35                  40                  45

Asn Leu Asp Thr Asn Arg Trp Gly Asn Ser Phe Phe Ser Ser Leu Pro
    50                  55                  60

Arg Ser Cys Lys Glu Ile Lys Gln Glu His Thr Lys Ala Gln Asp Gly
65                  70                  75                  80

Leu Tyr Phe Leu Arg Thr Lys Asn Gly Val Ile Tyr Gln Thr Phe Cys
                85                  90                  95

Asp Met Thr Thr Ala Gly Gly Gly Trp Thr Leu Val Ala Ser Val His
            100                 105                 110

Glu Asn Asn Met Arg Gly Lys Cys Thr Val Gly Asp Arg Trp Ser Ser
        115                 120                 125

Gln Gln Gly Asn Arg Ala Asp Tyr Pro Glu Gly Asp Gly Asn Trp Ala
    130                 135                 140

Asn Tyr Asn Thr Phe Gly Ser Ala Glu Ala Ala Thr Ser Asp Asp Tyr
145                 150                 155                 160

Lys Asn Pro Gly Tyr Phe Asp Ile Gln Ala Glu Asn Leu Gly Ile Trp
                165                 170                 175

His Val Pro Asn Lys Ser Pro Leu His Asn Trp Arg Lys Ser Ser Leu
            180                 185                 190

Leu Arg Tyr Arg Thr Phe Thr Gly Phe Leu Gln His Leu Gly His Asn
        195                 200                 205

Leu Phe Gly Leu Tyr Lys Lys Tyr Pro Val Lys Tyr Gly Glu Gly Lys
    210                 215                 220

Cys Trp Thr Asp Asn Gly Pro Ala Leu Pro Val Val Tyr Asp Phe Gly
225                 230                 235                 240

Asp Ala Arg Lys Thr Ala Ser Tyr Tyr Ser Pro Ser Gly Gln Arg Glu
                245                 250                 255

Phe Thr Ala Gly Tyr Val Gln Phe Arg Val Phe Asn Asn Glu Arg Ala
            260                 265                 270

Ala Ser Ala Leu Cys Ala Gly Val Arg Val Thr Gly Cys Asn Thr Glu
        275                 280                 285
```

```
His His Cys Ile Gly Gly Gly Gly Phe Phe Pro Glu Gly Asn Pro Val
    290                 295                 300

Gln Cys Gly Asp Phe Ala Ser Phe Asp Trp Asp Gly Tyr Gly Thr His
305                 310                 315                 320

Asn Gly Tyr Ser Ser Ser Arg Lys Ile Thr Glu Ala Ala Val Leu Leu
                325                 330                 335

Phe Tyr Arg Glu Leu Cys Gly Ile Gly Pro Asp Phe Ser Ile Val Gly
            340                 345                 350

Ser Lys Ala Glu Thr Leu Thr Leu Glu Cys Ala Ile Lys Gln Asp Lys
        355                 360                 365

Ser Cys Ser Leu Gln Lys Lys Lys
    370                 375
```

<210> SEQ ID NO 33
<211> LENGTH: 1136
<212> TYPE: DNA
<213> ORGANISM: Mus musculus

<400> SEQUENCE: 33

```
cagagaaagg ttcctgtcat tactcagcta gcaactctca gctcctgcct ggtccagagg     60

gaagaccacc atgacccaac tgggcttcct gctgtttatc atgattgcca cgagagtgtg    120

cagtgcagct gaagagaacc tggacaccaa cagatggggc aattctttct tttcctctct    180

gcccagaagc tgtaaggaaa tcaagcagga ggacacaaag gcacaagatg gtctctattt    240

cctgcgcacg gagaatggtg tcatctacca gaccttctgt gacatgacca ctgcaggtgg    300

tggctggacc ctggtggcta gtgtgcacga gaacaacctg cgtgggaggt gcactgtggg    360

tgatcgctgg tccagtcagc aaggcaacag agctgattac ccagaggggg atggcaactg    420

ggccaactac aacacctttg ggtctgcaga gggtgccaca agtgatgact acaagaaccc    480

tggctacttc gacatccagg cagagaacct gggcatctgg catgtgccca acaacagccc    540

cctgcacacc tggaggaaca gctccctgct gaggtaccgc accttcactg gcttcctgca    600

gcgcttgggc cataatctgt ttggtctcta ccagaagtat ccggtgaaat atggagaagg    660

aaagtgttgg actgacaatg gcccagcatt tcctgtggtc tatgactttg gtgatgctca    720

gaagacagcc tcttattact ctccctctgg ccggaatgaa ttcactgcag gatatgttca    780

gttcagagtg ttcaataatg agagagcagc cagtgccttg tgtgctggcg tgagggtcac    840

tggatgtaat actgaacatc actgcatcgg tggaggagga ttcttcccag aatttgaccc    900

cgaggagtgt ggagactttg ctgcatttga tgcgaatgga tatggaactc acattcggta    960

cagcaatagc cgggagataa ctgaagcagc tgtgcttctg ttttatcgct gagaactctg   1020

tgggattggc cctgacttct ccaatctatg ggctccaagg catgagaaac tctgacatag   1080

taacttcaat gctaatgagc aataaagcag aataaatcat gttccttgca aaaaaa       1136
```

<210> SEQ ID NO 34
<211> LENGTH: 374
<212> TYPE: PRT
<213> ORGANISM: Mus musculus

<400> SEQUENCE: 34

```
Arg Glu Arg Phe Leu Ser Leu Leu Ser Gln Leu Ser Ala Pro Ala Trp
1               5                   10                  15

Ser Arg Gly Lys Thr Thr Met Thr Gln Leu Gly Phe Leu Leu Phe Ile
            20                  25                  30

Met Ile Ala Thr Arg Val Cys Ser Ala Ala Glu Glu Asn Leu Asp Thr
```

-continued

```
        35                  40                  45

Asn Arg Trp Gly Asn Ser Phe Phe Ser Ser Leu Pro Arg Ser Cys Lys
    50                  55                  60

Glu Ile Lys Gln Glu Asp Thr Lys Ala Gln Asp Gly Leu Tyr Phe Leu
65                  70                  75                  80

Arg Thr Glu Asn Gly Val Ile Tyr Gln Thr Phe Cys Asp Met Thr Thr
                85                  90                  95

Ala Gly Gly Gly Trp Thr Leu Val Ala Ser Val His Glu Asn Asn Leu
            100                 105                 110

Arg Gly Arg Cys Thr Val Gly Asp Arg Trp Ser Ser Gln Gln Gly Asn
        115                 120                 125

Arg Ala Asp Tyr Pro Glu Gly Asp Gly Asn Trp Ala Asn Tyr Asn Thr
    130                 135                 140

Phe Gly Ser Ala Glu Gly Ala Thr Ser Asp Asp Tyr Lys Asn Pro Gly
145                 150                 155                 160

Tyr Phe Asp Ile Gln Ala Glu Asn Leu Gly Ile Trp His Val Pro Asn
                165                 170                 175

Asn Ser Pro Leu His Thr Trp Arg Asn Ser Ser Leu Leu Arg Tyr Arg
            180                 185                 190

Thr Phe Thr Gly Phe Leu Gln Arg Leu Gly His Asn Leu Phe Gly Leu
        195                 200                 205

Tyr Gln Lys Tyr Pro Val Lys Tyr Gly Glu Gly Lys Cys Trp Thr Asp
    210                 215                 220

Asn Gly Pro Ala Phe Pro Val Val Tyr Asp Phe Gly Asp Ala Gln Lys
225                 230                 235                 240

Thr Ala Ser Tyr Tyr Ser Pro Ser Gly Arg Asn Glu Phe Thr Ala Gly
                245                 250                 255

Tyr Val Gln Phe Arg Val Phe Asn Asn Glu Arg Ala Ala Ser Ala Leu
            260                 265                 270

Cys Ala Gly Val Arg Val Thr Gly Cys Asn Thr Glu His His Cys Ile
        275                 280                 285

Gly Gly Gly Gly Phe Phe Pro Glu Phe Asp Pro Glu Glu Cys Gly Asp
    290                 295                 300

Phe Ala Ala Phe Asp Ala Asn Gly Tyr Gly Thr His Ile Arg Tyr Ser
305                 310                 315                 320

Asn Ser Arg Glu Ile Thr Glu Ala Ala Val Leu Leu Phe Tyr Arg Glu
                325                 330                 335

Leu Cys Gly Ile Gly Pro Asp Phe Ser Asn Leu Trp Ala Pro Arg His
            340                 345                 350

Glu Lys Leu His Ser Asn Phe Asn Ala Asn Glu Gln Ser Arg Ile Asn
        355                 360                 365

His Val Pro Cys Lys Lys
    370
```

<210> SEQ ID NO 35
<211> LENGTH: 32
<212> TYPE: DNA
<213> ORGANISM: Artificial sequence
<220> FEATURE:
<223> OTHER INFORMATION: Synthetic primer

<400> SEQUENCE: 35
cgtgggatcc tggagggagg gagtgaagga gc 32

<210> SEQ ID NO 36

-continued

```
<211> LENGTH: 36
<212> TYPE: DNA
<213> ORGANISM: Artificial sequence
<220> FEATURE:
<223> OTHER INFORMATION: Synthetic primer

<400> SEQUENCE: 36

gccagctcga gaccttggga tctcatggtt gggagg                          36


<210> SEQ ID NO 37
<211> LENGTH: 80
<212> TYPE: DNA
<213> ORGANISM: Artificial sequence
<220> FEATURE:
<223> OTHER INFORMATION: Synthetic primer

<400> SEQUENCE: 37

accaccagag gatggagtac agattggagc catccgcagt ttgaaaagtc tacagatgag     60

gctaatactt acttcaagga                                                80


<210> SEQ ID NO 38
<211> LENGTH: 80
<212> TYPE: DNA
<213> ORGANISM: Artificial sequence
<220> FEATURE:
<223> OTHER INFORMATION: Synthetic primer

<400> SEQUENCE: 38

accaccagag gatggagtac agattggagc catccgcagt ttgaaaagtc tacagatgag     60

gctaatactt acttcaagga                                                80
```